(12) United States Patent
Otvos et al.

(10) Patent No.: US 8,778,890 B2
(45) Date of Patent: Jul. 15, 2014

(54) LEPTIN ANTAGONIST AND METHODS OF USE

(75) Inventors: Laszlo Otvos, Audubon, PA (US); Eva Surmacz, Philadelphia, PA (US)

(73) Assignee: Temple University—of the Commonwealth System of Higher Education, Philadelphia, PA (US)

( * ) Notice: Subject to any disclaimer, the term of this patent is extended or adjusted under 35 U.S.C. 154(b) by 257 days.

(21) Appl. No.: 13/262,186

(22) PCT Filed: Mar. 30, 2010

(86) PCT No.: PCT/US2010/029201
§ 371 (c)(1),
(2), (4) Date: Nov. 4, 2011

(87) PCT Pub. No.: WO2010/117785
PCT Pub. Date: Oct. 14, 2010

(65) Prior Publication Data
US 2012/0142585 A1    Jun. 7, 2012

Related U.S. Application Data

(60) Provisional application No. 61/211,527, filed on Mar. 31, 2009.

(51) Int. Cl.
*A61K 38/08*    (2006.01)

(52) U.S. Cl.
USPC ........................................................ 514/21.6

(58) Field of Classification Search
None
See application file for complete search history.

(56) References Cited

U.S. PATENT DOCUMENTS

| | | | |
|---|---|---|---|
| 6,399,745 B1 | 6/2002 | Ertl et al. | 530/350 |
| 7,015,309 B1 | 3/2006 | Otvos | 530/350 |
| 2002/0064856 A1 | 5/2002 | Plowman et al. | 435/226 |
| 2002/0147145 A1 | 10/2002 | Mailand et al. | 514/12 |
| 2004/0176300 A1 | 9/2004 | Subbalakshmi et al. | 514/14 |
| 2005/0244400 A1 | 11/2005 | LeBowitz et al. | 424/94.61 |
| 2006/0014712 A1 | 1/2006 | Neuman | 514/44 |
| 2006/0024820 A1* | 2/2006 | Perkins et al. | 435/320.1 |
| 2006/0046959 A1 | 3/2006 | Tavernier et al. | 514/12 |
| 2006/0154859 A1 | 7/2006 | Gertler et al. | 514/12 |
| 2006/0165683 A1 | 7/2006 | Karsenty et al. | 424/143.1 |
| 2008/0188399 A1 | 8/2008 | Sinko et al. | 514/2 |
| 2008/0207512 A1 | 8/2008 | Roth et al. | 514/12 |

FOREIGN PATENT DOCUMENTS

WO    WO 2008/070049    6/2008    ............ A61K 38/10

OTHER PUBLICATIONS

Balasubramaniam et al ('Structure-activity studies including a (CH2-NH) scan of peptide YY(PYY) active site, PYY(22-36), for interaction with rat intestinal PYY receptors:development of analogues with potent in vivo activity in the intestine' J Med Chem 200 v43 pp. 3420-3427).*

Cassone, et al., "Scope and limitations of the designer proline-rich antibacterial peptide dimmer, A3-APO, alone or in synergy with conventional antibiotics", *Peptides* 29 (2008) 1878-1886.

Garofalo, et al., "Leptin and Cancer", *Journal of Cellular Physiology* 207: 12-22 (2006).

Gonzalez, et al., "A Peptide Derived from the Human Leptin Molecule Is a Potent Inhibitor of the Leptin Receptor Function in Rabbit Endometrial Cells", *Endocrine*, vol. 21, No. 2, 185-195, Jul. 2003.

Lago, et al., "Leptin beyond body weight regulation—Current concepts concerning its role in immune function and inflammation", *Cellular Immunology* 252 (2008) 139-145.

Otvos, et al., "Development of a pharmacologically improved peptide agonist of the leptin receptor", *Biochimica et Biophysica Acta* 1783 (2008) 1745-1754.

Niv-Spector, et al., "Identification of the hydrophobic strand in the A-B loop of leptin as major binding site III: implications for large-scale preparation of potent recombinant human and ovine leptin antagonists", *Biochem J.* (2005) 391, 221-230.

Peelman, et al., "Mapping of the Leptin Binding Sites and Design of a Leptin Antagonist", *The Journal of Biological Chemistry*, vol. 279, No. 39, Issue of Sep. 24, 2004. pp. 41038-41046.

* cited by examiner

*Primary Examiner* — James H Alstrum Acevedo
*Assistant Examiner* — Ronald Niebauer
(74) *Attorney, Agent, or Firm* — Drinker Biddle & Reath LLP

(57) ABSTRACT

This invention provides compounds that are true antagonists of the leptin receptor, in the presence and the absence of native leptin or another leptin receptor binder. These compounds may be used to inhibit leptin receptor activity, promote growth arrest or death of leptin receptor-positive cancer cells, or monitor or detect a leptin receptor-positive cell, in vitro or in vivo. These compounds may also be used to treat a weight-loss nutritional disorder, osteoporosis, rheumatoid arthritis, osteoarthritis, or inflammatory bowel disease. Also included in the invention are methods for detecting leptin receptor-positive cells, for arresting cell growth or killing cancer cells in vivo, for monitoring or detecting a leptin receptor-positive cell in vitro or in vivo, for treating a weight-loss nutritional disorder, for treating osteoporosis, for treating rheumatoid arthritis, for treating osteoarthritis, or for treating inflammatory bowel disease.

22 Claims, 10 Drawing Sheets

Sample Numbers:    1    2    3    4    5    6

LEPTIN ANTAGONIST AND METHODS OF USE

CROSS REFERENCE TO RELATED APPLICATION

This application claims priority under 35 U.S.C. §119(e) to U.S. Provisional Application No. 61/211,527, filed Mar. 31, 2009, which application is incorporated by reference herein in its entirety.

FIELD OF INVENTION

The invention relates to leptin antagonists and their use in treatment of weight-loss nutritional disorders, such as wasting and cachexia, obesity-related cancers, osteoporosis, rheumatoid arthritis, osteoarthritis and inflammatory bowel disease.

BACKGROUND OF INVENTION

Leptin is a neurohormone that acts in the hypothalamus to regulate energy balance and food intake (Wauters et al., 2000, Eur. J. Endocrinol, 143:293-311). Recessive mutations in leptin or the gene for its receptor, ObR, result in profound obesity and type II diabetes mellitus (Zhang et al., 1994, Nature 372:425-432). In addition to its role as a neurohormone, leptin can modulate immune response, fertility, and hematopoiesis, acting as a mitogen, metabolic regulator, or pro-angiogenic factor (Wauters et al., 2000, Eur. J. Endocrinol. 143:293-311).

The amino acid sequence of leptin (SEQ ID NO:1) was described by Masuzaki et al. (Diabetes 1995, 44:855-858). Leptin binds to multiple isoforms of its receptor ObR. For example, the signaling pathways activated by leptin receptor isoform ObR1 upon leptin binding include the classic cytokine JAK2/STAT3 (Janus kinase 2/signal transducer and activator of transcription 3) pathway, the Ras/ERK1/2 (Ras/extracellular signal-regulated kinases 1/2) signaling cascade, and the PI3K/Akt/GSK3 (phosphoinositide 3 kinase/protein kinase B/glycogen synthase kinase 3) growth/anti-apoptotic pathway. In addition, leptin has been found to induce PLC-γ (phospholipase C-gamma), PKC (protein kinase C), p38 kinase, and nitric oxide (NO) production (Bjorbaek et al., 1997, J. Biol. Chem. 272:32686-32695; Sweeney, 2002, Cell. Signal. 14:655-663; Zabeau et al., 2003, FEBS Lett. 546:45-50). Ultimately, induction of ObR1 may activate several genes involved in cell proliferation, including c-fos, c-jun, junB, egr-1, and socs3, and upregulate the expression angiogenic factors, such as VEGF (Sweeney, 2002, Cell. Signal. 14:655-663; Zabeau et al., 2003, FEBS Lett. 546:45-50; Frankenberry et al., 2004, Am. J. Surg. 188:560-565).

The residues around residue 40 of leptin are labeled as site I, those residues at the very N-terminus and in the middle of the protein are labeled as binding site II, and the residues at the C-terminus are labeled as binding site III. Interfering with these binding surfaces may increase or decrease the efficiency of downstream ObR signaling. Full-length leptin and point mutants of full-length leptin have been examined as potential therapeutic agents for obesity, but the results were disappointing, largely due to leptin resistance in obese people as well as difficulties in recombinant leptin delivery to the central nervous system (Montez et al., 2005, Proc. Natl. Acad. Sci. USA 102:2537-2542).

As a first indication of the possibility of growth arrest upon ObR inactivation, the proliferation rate of leptin-sensitive BAF/3 cells stably transfected with the long form of human leptin receptor was measured after treatment of leptin fragments and their mutants (Niv-Spector et al., 2005, Biochem. J. 391:221-230). It was found that single-point mutations in leptin binding site III lower the affinity between the ligand and the receptor, drastically attenuating the agonistic activity and converting those mutants into both partial antagonists and weak agonists.

The multiple roles that leptin plays in various biological processes suggest that it is not straightforward to obtain true agonists or antagonists that do not change the downstream signaling effect upon varying environmental conditions. Indeed, the emergence of both partial antagonists and weak agonists as listed above indicates that, depending upon the cell lines used, as well as the presence or absence of native, unmodified leptin, the same mutant protein or large subunit can trigger different biological responses. The use of such proteins and peptides in human or veterinary therapy may be problematic, as the peptides do not demonstrate pure, controllable agonist or antagonistic activity against the leptin receptor.

In the context of energy balance, leptin plays a key role in regulating energy balance and food intake. Disruption in normal leptin production or activity causes severe obesity cases in affected individuals. It is thus possible that a leptin antagonist could be used to purposefully cause weight gain or stop weight loss in individuals with a severe case of nutrition disorder, such as cachexia or wasting. Cachexia is the term used to define weight loss, muscle atrophy, fatigue, weakness and significant appetite loss in an individual who is not actively trying to lose weight. Cachexia is generally associated with cancer, metabolic acidosis (from decreased protein synthesis and increased protein catabolism), infectious diseases (such as tuberculosis and AIDS), autoimmune disorders or drug addiction. This condition physically weakens patients to a state of immobility stemming from loss of appetite, asthenia and anemia, and response to standard treatment is usually poor. Wasting refers to the process by which a debilitating disease causes muscle and fat tissue to "waste" away. Wasting is sometimes referred to as "acute malnutrition" because it is believed that episodes of wasting have a short duration, in contrast to stunting, which is regarded as chronic malnutrition. Wasting can be caused by an extremely low energy intake (e.g., caused by famine), nutrient losses due to infection, or a combination of low intake and high loss. Infections associated with wasting include tuberculosis, chronic diarrhea, and AIDS. The mechanism may involve cachectin (also called tumor necrosis factor), a macrophage-secreted cytokine. Voluntary weight loss and eating disorders are excluded as causes of wasting. A leptin antagonist that is able to act on the leptin receptors located in the central nervous system should be able to counterbalance or mitigate the negative effects of cachexia or wasting on an individual.

In the context of cancer, it is noteworthy that leptin expression can be induced under hypoxic conditions, which often occur in solid tumors (Ambrosini et al., 2002, J. Biol. Chem. 277(37):34601-34609; Grosfeld et al., 2002, J. Biol. Chem. 277(45):42953-42957). Hypoxia and chemical inducers of cellular hypoxia are able to activate the leptin gene promoter through the hypoxia-induced factor-1 (HIF-1) in human adipocytes and fibroblasts (Ambrosini et al., 2002, J. Biol. Chem. 277(37):34601-34609; Grosfeld et al., 2002, J. Biol. Chem. 277(45):42953-42957). These data suggest that leptin may play a role in vascular remodeling (Stenmark et al., 2002, Chest 122 (6 Suppl):3265-3345). Indeed, leptin has been shown to regulate neo-angiogenesis by itself and in concert with vascular endothelial growth factor (VEGF) and basic fibroblast growth factor (FGF-2) (Bouloumie et al., 1998, Circ. Res. 83(10):1059-1066; Sierra-Honigmann et al., 1998, Science 281(5383):1683-1686; Cao et al., 2001, Proc. Natl. Acad. Sci. USA 98(11):6390-6395). In addition to the pro-angiogenic function, leptin may enhance endothelial cell growth (Bouloumie et al., 1998, Circ. Res. 83(10):1059-1066; Sierra-Honigmann et al., 1998, Science 281(5383): 1683-1686) and suppress apoptosis through a Bcl-2-dependent mechanism (Artwohl et al., 2002, Int. J. Obes. Relat. Metab. Disord. 26(4):577-580). The role of leptin in neovascularization is supported additionally by the observation that the hormone can increase the levels and activity of enzymes involved in angiogenesis, for example, matrix metalloproteinases (MMPs) 2 and 9 (Park et al., 2001, Exp. Mol. Med. 33(2):95-102; Kume et al., 2002, J. Histochem. Cytochem. 50(2):159-169). In addition to its involvement in endothelial cell function, leptin has been shown to act as a mitogen, transforming factor or migration factor for many different cell types, including smooth muscle cells (Oda et al., 2001, Kobe J. Med. Sci. 47(3):141-150), normal and neoplastic colon cells (Hardwick et al., 2001, Gastroenterology 121(1):79-90; Liu et al., 2001, Int. J. Oncol. 19(5):1009-1014), and normal and malignant mammary epithelial cells (Dieudonne et al., 2002, Biochem. Biophys. Res. Commun. 293(1):622-628; Laud et al., 2002, Mol. Cell. Endocrinol. 188(1-2):219-226).

Leptin can act as a mitogen and an angiogenic factor, suggesting that leptin may play a key role in cancer development and progression. In that context, leptin antagonists, acting as inhibitors of the activity associated with the leptin receptors, could find use in treatment of various kinds of cancer (Garofalo & Surmacz, 2006, J. Cell. Phys. 207:12-22, incorporated herein by reference in its entirety), such as glioma, breast cancer, colorectal cancer, prostate cancer, pancreatic cancer, ovarian cancer, endometric cancer and lung cancer. Recent research efforts focused on peptides related to the site III of leptin (Otvos et al., 2008, Biochim. Biophys. Acta 1783:1745-1754). These peptides were not true ObR antagonists, but rather partial agonists/antagonists depending upon the presence or absence of other ObR ligands. A therapeutically useful leptin antagonist should maintain the antagonistic activity in the presence of leptin or other ObR ligands, based on the fact that obese individuals have higher than normal levels of circulating leptin in their bodies (Frederich et al., 1995, J. Clin. Invest. 96(3):1658-1663; Ahima et al., 1996, Nature 382(6588):250-252; Boden et al., 1996, J. Clin. Endocrinol. Metab. 81(9):3419-3423; Sinha et al., 1996, J. Clin. Invest. 97(5):1344-1347; der Merwe et al., 1999, Int. J. Obes. Relat. Metab. Disord. 23(9):909-917; Thomas et al., 2000, Metabolism 49(10):1278-1284).

In the context of osteoporosis, fat metabolism is related to both arteriosclerosis and bone metabolism. Obese patients have higher risk of coronary artery disease and lower risk of osteoporosis. Recent studies by Ricci et al. (Am. J. Clin. Nutr. 2001, 73(2):347-352) showed that even moderate weight loss due to dieting in obese women leads to bone loss. A study from Denmark by Jensen et al. (J. Bone Miner. Res. 2001, 16(1):141-147) found a 4.2% decrease in whole body bone mineral and 4.0% decrease in the hip in women after 6 months of a diet that resulted in 5.5% weight loss (average 94 of 89 kg, or 207 to 196 lbs). The loss in bone density was attenuated by calcium supplementation. On the other hand, a study of 130 young women with anorexia showed a high prevalence of fractures and of low bone density. The bone density was related to weight at all skeletal sites.

Leptin appears to have a profound effect on bone density. Some authors, such as Mundy (Ann. Intern. Med. 2000, 133 (10):828-830), proposed that leptin regulation was responsible for increased body weight as well as increased bone density. Mice who have congenital absence of leptin (ob/ob) are obese and have very high bone density. Leptin makes them lose both fat and bone. Leptin injected into the brain of animals will inhibit bone formation at doses lower than those that cause loss of body weight. Based on this evidence, an antagonist of the leptin receptor would be expected to promote bone formation in an affected individual.

Rheumatoid arthritis (RA) is a chronic, systemic inflammatory disorder that may affect many tissues and organs, but principally attacks the joints producing an inflammatory synovitis that often progresses to destruction of the articular cartilage and ankylosis of the joints. Rheumatoid arthritis can also produce diffuse inflammation in the lungs, pericardium, pleura, and sclera, and also nodular lesions, most common in subcutaneous tissue under the skin. Although the cause of rheumatoid arthritis is unknown, autoimmunity plays a pivotal role in its chronicity and progression. About 1% of the world's population is afflicted by rheumatoid arthritis. Rheumatoid arthritis affects women three times more often than men, and it can first develop at any age. The risk of first developing the disease (the disease incidence) appears to be greatest for women between 40 and 50 years of age, and for men somewhat later. It is a disabling and painful condition, which can lead to substantial loss of functioning and mobility.

Various treatments are available. Non-pharmacological treatment includes physical therapy, orthoses and occupational therapy. Analgesia (painkillers) and anti-inflammatory drugs, including steroids, are used to suppress the symptoms, while disease-modifying antirheumatic drugs (DMARDs) are often required to inhibit or halt the underlying immune process and prevent long-term damage. In recent times, the newer group of biologics has increased treatment options.

While rheumatoid arthritis primarily affects joints, problems involving other organs of the body are known to occur. Extra-articular ("outside the joints") manifestations other than anemia (which is very common) are clinically evident in about 15-25% of individuals with rheumatoid arthritis. It can be difficult to determine whether disease manifestations are directly caused by the rheumatoid process itself, or from side effects of the medications commonly used to treat it—for example, lung fibrosis from methotrexate or osteoporosis from corticosteroids.

The arthritis of joints known as synovitis is inflammation of the synovial membrane that lines joints and tendon sheaths. Joints become swollen, tender and warm, and stiffness limits their movement. With time RA nearly always affects multiple joints, most commonly small joints of the hands, feet and cervical spine, but larger joints like the shoulder and knee can also be involved. Synovitis can lead to tethering of tissue with loss of movement and erosion of the joint surface causing deformity and loss of function.

Rheumatoid arthritis is a form of autoimmunity, the causes of which are still incompletely known. It is a systemic (whole body) disorder principally affecting synovial tissues. There is no known cure for rheumatoid arthritis, but many different types of treatment can alleviate symptoms and/or modify the disease process. Most authorities believe that most RA should be treated by at least one specific anti-rheumatic medication, also named DMARD, to which other medications and non-medical interventions can be added as needed. Cortisone injections can be valuable adjuncts to a long-term treatment plan, and using low dosages of daily cortisone (e.g., prednisone or prednisolone, 5-7.5 mg daily) can also have an important benefit if added to a proper specific anti-rheumatic treatment.

Pharmacological treatment of RA can be divided into disease-modifying antirheumatic drugs (DMARDs), anti-inflammatory agents and analgesics. Examples of chemically synthesised DMARDs are: azathioprine, ciclosporin (cyclosporine A), D-penicillamine, gold salts, hydroxychloroquine, leflunomide, methotrexate (MTX), minocycline and sulfasalazine (SSZ). An example of a cytotoxic drug is cyclophosphamide. Examples of biological agents (biologics) are: tumor necrosis factor alpha (TNFα) blockers (such as etanercept (Enbrel), infliximab (Remicade), adalimumab (Humira), certolizumab pegol (Cimzia), and golimumab (Simponi)), Interleukin 1 (IL-1) blockers (such as anakinra (Kineret)), monoclonal antibodies against B cells (such as rituximab (Rituxan)), T cell costimulation blocker (such as abatacept (Orencia)) and Interleukin 6 (IL-6) blockers (such as tocilizumab (an anti-IL-6 receptor antibody) (RoActemra, Actemra)). Examples of anti-inflammatory agents include glucocorticoids and non-steroidal anti-inflammatory drug (NSAIDs, most also act as analgesics). Examples of analgesics include paracetamol (acetaminophen in US and Canada), opiates, diproqualone and lidocaine topical.

Obesity may aggravate RA (Gomez et al., 2009, J. Mol. Endocrinol. 43:11-18). Although increased joint loading has been proposed to explain these functional links, the positive association between obesity and rheumatoid disease was identified not only in weight-bearing joints, but also in the hand, suggesting an involvement of an obesity-related metabolic factor (Magliano, 2008, Menopause Int. 14:149-154). Leptin might contribute to pathogenesis of RA, as suggested by the observations that leptin levels are higher in individuals with RA then in healthy people and leptin can increase IL-8 production by synovial fibroblasts from RA patients (Gomez et al., 2009, J. Mol. Endocrinol. 43:11-18). However, the molecular mechanism linking leptin to RA is still unclear (Otero et al., 2006, Arthritis Rheum. 48:404-409).

Osteoarthritis (OA, also known as degenerative arthritis or degenerative joint disease) is a group of diseases and mechanical abnormalities involving degradation of joints, including articular cartilage and the subchondral bone next to it. Clinical manifestations of OA may include joint pain, tenderness, stiffness, creaking, locking of joints, and sometimes local inflammation. In OA, a variety of potential forces (hereditary, developmental, metabolic, and mechanical) may initiate processes leading to loss of cartilage (a strong protein matrix that lubricates and cushions the joints). As the body struggles to contain ongoing damage, immune and regrowth processes can accelerate damage (Brandt et al., 2008, Med. Clin. N. Am. 93(1):1-24). When bone surfaces become less well protected by cartilage, subchondral bone may be exposed and damaged, with regrowth leading to a proliferation of ivory-like, dense, reactive bone in central areas of cartilage loss, a process called eburnation. The patient increasingly experiences pain upon weight bearing, including walking and standing. As a result of decreased movement because of the pain, regional muscles may atrophy, and ligaments may become more lax.

OA is the most common form of arthritis and the leading cause of chronic disability in the United States. OA affects nearly 27 million people in the United States, accounting for 25% of visits to primary care physicians, and half of all NSAID (Non-Steroidal Anti-Inflammatory Drugs) prescriptions. It is estimated that 80% of the population will have radiographic evidence of OA by age 65, although only 60% of those will show symptoms. In the United States, hospitalizations for osteoarthritis soared from about 322,000 in 1993 to 735,000 in 2006.

Osteoarthritis is not to be confused with rheumatoid arthritis, an autoimmune disease with joint inflammation as a main feature. A common misconception is that OA is due solely to wear and tear, since OA typically is not present in younger people. However, while age is correlated with OA incidence, this correlation may illustrate that OA is a process that takes time to develop, or that repair and regeneration that may keep pace with damage in the joints of younger people do slow with age. There is sometimes a diagnosable underlying cause for OA, in which case it is described as secondary OA. In the majority of cases no cause can be identified, described as primary OA. "Degenerative arthritis" is often used as a synonym for OA, but the latter involves both degenerative and regenerative changes.

The main symptom of OA is acute pain, causing loss of ability and often stiffness. "Pain" is generally described as a sharp ache, or a burning sensation in the associate muscles and tendons. OA can cause a crackling noise (called "crepitus") when the affected joint is moved or touched, and patients may experience muscle spasm and contractions in the tendons. Occasionally, the joints may also be filled with fluid. Humid and cold weather increases the pain in many patients. OA commonly affects the hands, feet, spine, and the large weight bearing joints, such as the hips and knees, although in theory, any joint in the body can be affected. As OA progresses, the affected joints appear larger, are stiff and painful, and usually feel worse, the more they are used throughout the day, thus distinguishing it from rheumatoid arthritis.

Treatment of OA consists of exercise, manual therapy, lifestyle modification, medication and other interventions to alleviate pain. Medication used to treat OA includes paracetamol (acetaminophen), non-steroidal anti-inflammatory drugs (such as diclofenac, ibuprofen, naproxen, ketoprofen, and COX-2 selective inhibitors, such as celecoxib, rofecoxib and valdecoxib), intra-articular corticosteroids, opioid analgesic (such as morphine or codeine), topical NSAIDs (diclofenac, ibuprofen, and ketoprofen), creams and lotions containing capsaicin, injections of hyaluronic acid or glucocorticoids (such as hydrocortisone).

Both metabolic and biochemical mechanisms contribute to the onset of OA (Pelletier et al., 2004, Bone 34:527-538). OA is strongly correlated with a high body mass index (Felson et al., 1988, Ann. Intern. Med. 109:18-24) and weight loss is associated with decreased disease progression (Christensen et al., 2007, Ann. Rheum. Dis. 66:433-439), suggesting a functional biochemical link between obesity and OA (Sandell, 2009, Arthritis Rheum. 60:2858-2860; Gomez et al., 2009, J. Mol. Endocrinol. 43:11-18). Indeed, recent data point out to leptin as the link between obesity and inflammatory osteoarthritic degeneration (Fantuzzi, 2005, J. Allergy Clin. Immunol. 115:911-919; Gomez et al., 2009, J. Mol. Endocrinol. 43:11-18; Lago et al., 2008, Nat. Clin. Pract. Rheumatol. 3:716-724; Otero et al., 2006, Drug News Perspect. 19:21-26; Vuolteenaho et al., 2009, Mediators Inflamm. 345838).

There is compelling evidence that leptin is implicated in the pathology of OA. Leptin-deficient mice are protected from OA, implying that leptin has a pro-degenerative function in cartilage (Griffin et al., 2009, Arthritis Rheum. 60:2935-2944). Indeed, leptin expression is increased in OA human cartilage compared to normal cartilage. In cultured cartilage explants, leptin can induce the expression of several pro-inflammatory mediators, i.e., iNOS, cyclooxygenase (COX) 2, nitric oxide (NO), prostaglandin E2 (PGE2), interleukin (IL-6 and IL-8) through the activation of nuclear factor (NF)-κB, ERK1/2 and other pathways (Vuolteenaho et al., 2009, Mediators Inflamm. 345838). In cultured human and murine chondrocytes, type 2 NO synthase (NOS2) is synergistically activated by leptin and interferon-γ or IL-1 (Otero et al., 2003, Arthritis Rheum. 48:404-409; Otero et al., 2007, Life Sci. 81:1452-1460). In addition, leptin can induce the synthesis of matrix metalloproteinases (MMP) involved in cartilage damage, such as MMP-9 and MMP-13 (Gomez et al., 2009, J. Mol. Endocrinol. 43:11-18). It is hypothesized that increased OA incidents in females could be due to higher, relative to males, circulating leptin levels (Teichtahl et al., 2005, Med. Hypotheses 65:312-315).

Inflammatory bowel disease (IBD) is a term generally used to refer to conditions such as Crohn's disease (CD) and ulcerative colitis (UC), and, to a lesser extent, indeterminate colitis and infectious colitis. Inflammatory bowel diseases are chronic recurrent inflammatory diseases of unclear etiology (and thus classified as "idiopathic"), affecting the small intestine and colon. IBD may involve either or both the small and large bowel.

Pathologic findings are generally not specific, although they may suggest a particular form of IBD. "Active" IBD is characterized by acute inflammation. "Chronic" IBD is characterized by architectural changes of crypt distortion and scarring. The term "crypt" refers to a deep pit that protrudes down into the connective tissue surrounding the small intestine. Crypt abscesses (active IBD characterized by the presence of neutrophils in crypt lumens) can occur in many forms of IBD, not just UC. Under normal conditions the epithelium at the base of the crypt is the site of stem cell proliferation and the differentiated cells move upwards and are shed 3-5 days later at the tips of the villi. This normal process, necessary for proper bowel function, is interrupted by IBD.

UC involves the colon as a diffuse mucosal disease with distal predominance. The rectum is virtually always involved, and additional portions of colon may be involved extending proximally from the rectum in a continuous pattern. Most often UC occurs in young people 15 to 40 years of age. UC occurs only in the inner lining of the colon (large intestine) or rectum. When it is localized in the rectum, it is called "proctitis."

CD is a chronic inflammatory disease that has periods of remission (time when person feels well) and relapse (when a person feels ill). CD is an inflammation and ulceration process that occurs in the deep layers of the intestinal wall. The most common areas affected are the lower part of the small intestine, called the ileum, and the first part of the colon. This type of CD is called ileocolitis. CD can infrequently affect any part of the upper gastrointestinal tract. Aphthous ulcers, which are similar to cold sores, are common. Ulcers can also occur in the esophagus, stomach and duodenum.

Therapy for IBD has historically included administration of corticosteroids. However drawbacks of long term corticosteroid therapy include masking (or induction) of intestinal perforation, osteonecrosis and metabolic bone disease. Additional problems relate to development of corticosteroid dependency (Habnauer, 1996, New England Journal of Medicine 334(13):841-848). Aminosalicylates such as sulfasalazine and mesalamine have been used to treat mild or moderately active UC and CD, and to maintain remission. Immunomodulatory drugs such as azathioprine and mercaptopurine have been used in long term treatment for patients with IBD. Common complications with both of these drugs include pancreatitis, which occurs with an incidence of 3-15% of patients, and bone marrow suppression, which requires regular monitoring. More potent immunosuppressive drugs such as cyclosporine and methotrexate have been employed, but toxicity of these drugs limits their use to specific situations of refractory disease states. Other therapeutic approaches include antibiotic therapy and nutritional therapy. Often, therapy involves a combination of the above-described drug therapies in addition to surgical resection of the bowel. There is no cure for IBD. Ultimately, the chronic and progressive nature of IBD demands a long-term treatment that maximizes the local anti-inflammatory effect while minimizing the global systemic effect on the immune system.

Chronic inflammatory disorders such as CD typically demonstrate periods of remission between intervals when the inflammatory is active and requires acute treatment. This is an example of a circumstance wherein it is known beforehand that an individual will develop, or is likely to develop an inflammatory disorder.

Irritable bowel syndrome (IBS) is a disorder of the bowel which is distinct from IBD. IBS affects at least 10% to 20% of adults in the U.S. IBS is the most common disorder diagnosed by gastroenterologists and one of the top ten most frequently diagnosed conditions among U.S. physicians. IBS is classified as a "functional gastrointestinal disorder," wherein there is a disturbance in bowel function. IBS is not a considered a disease, but rather a syndrome, i.e., a group of symptoms. The symptoms typically include chronic abdominal pain/discomfort, and irregular bowel function, e.g., diarrhea, constipation, or alternating diarrhea and constipation. Unlike IBD, MS does not cause inflammation. IBS sufferers show no sign of disease or abnormalities on examination of the colon. Thus, though IBD and IBS share some similar symptoms, particularly cramping and diarrhea, the underlying disease process is quite different. MD involves inflammation or destruction of the bowel wall, which can lead to deep ulcerations and narrowing of the intestines. IBS is a disorder of the gastrointestinal (GI) tract for which no apparent cause can be found. An individual can simultaneously have both IBS and an inflammatory disorder such as IBD. When this occurs, imprecise diagnosis may lead to inadequate medical intervention.

Inflammatory bowel disease (IBD) is characterized by anorexia, malnutrition, altered body composition, and development of mesenteric white adipose tissue (WAT) hypertrophy. Increasing evidence suggests that adipokines synthesized either in WAT or in immune cells are involved in these manifestations of IBD (Karmiris et al., 2006, Inflamm Bowel Dis. 12(2):100-5). Among adipokines, leptin holds a fundamental role. Preliminary studies have shown over-expression of leptin in mesenteric WAT of patients with Crohn's disease (CD) and significant alterations of circulating serum levels of this adipokine in IBD. In animal models of intestinal inflammation, existing data suggest that leptin is a pivotal mediator of inflammation. Interesting therapeutic interventions based on these data have been suggested. A specific role for hypertrophic WAT has also been implicated in CD. Further efforts with experimental and clinical studies are needed to better understand the role of leptin in IBD.

There is thus still great need for a leptin-based antagonist that acts as such in the presence or absence of other leptin receptor ligands. The present invention addresses and meets these needs.

SUMMARY OF INVENTION

As described herein, the inventors have surprisingly discovered compounds that act as true antagonists of the leptin receptor, both in the presence and the absence of native leptin. These compounds find use in promoting growth arrest or killing leptin-receptor-positive cancer cells in culture, as well as in the treatment of leptin-receptor-positive cancerous tumors in vivo, and in monitoring or detecting a leptin receptor-positive cell in vitro or in vivo. These compounds also find use in treatment of weight-loss nutritional disorders, such as cachexia and wasting. These compounds also find use in treatment of osteoporosis and related bone-loss diseases. These compounds also find use in treatment of rheumatoid arthritis. These compounds also find use in treatment of osteoarthritis. These compounds also find use in treatment of inflammatory bowel disease.

The invention includes a compound according to Formula (I):

$$X^1\text{-M-SEQ ID NO: 2} \quad (I)$$

or a salt thereof, wherein:
SEQ ID NO:2 represents $Xaa_1$-Glu-Nva-Val-Ala-Leu-Ser-$Xaa_2$-$Xaa_3$, wherein:
$Xaa_1$ is zero amino acid or a hydroxylated acyclic amino acid;
$Xaa_2$ is Arg or N-MeArg;
$Xaa_3$ is an aliphatic amino acid; and,
$X^1$-M represents an optional group comprising a tagging element conjugated to the N-terminus of the amino acid sequence SEQ ID NO:2, wherein:
$X^1$ represents the tagging element, wherein the tagging element is selected from the group consisting of a transduction domain and a detection label; and,
-M- represents a single bond or an optional linking group forming a covalent linkage between the tagging element and the amino acid sequence SEQ ID NO:2.

In one embodiment of the invention, -M- consists of a single bond, an amino acid or a peptide. In another embodiment of the invention, the tagging element is directly linked at its C-terminus to -M-.

According to one embodiment, $Xaa_1$ is zero amino acid. According to another embodiment, $Xaa_1$ is serine. According to yet another embodiment, $Xaa_1$ is (D)-Ser. According to yet another embodiment, $Xaa_1$ is threonine. According to yet another embodiment, $Xaa_1$ is (D)-threonine. According to yet another embodiment, $Xaa_1$ is (L)-allo-threonine. According to yet another embodiment, $Xaa_1$ is (D)-allo-threonine. According to yet another embodiment, $Xaa_1$ is (L)-isoserine. According to yet another embodiment, $Xaa_1$ is (D)-isoserine. According to yet another embodiment, $Xaa_1$ is (L)-β-homoserine. According to yet another embodiment, $Xaa_1$ is (D)-β-homoserine. According to yet another embodiment, $Xaa_1$ is (L)-homoserine. According to yet another embodiment, $Xaa_1$ is (D)-homoserine. According to yet another embodiment, $Xaa_2$ is Arg. According to yet another embodiment, $Xaa_2$ is N-MeArg. According to yet another embodiment, $Xaa_3$ is selected from the group consisting of bAla (also known as beta-alanine), bAlaNH$_2$ (also known as 3-aminopropanamide), Acp (also known as 6-aminocaproic acid) and AcpNH$_2$ (also known as 6-aminocapramide). According to yet another embodiment, $Xaa_3$ is bAla. According to yet another embodiment, $Xaa_3$ is bAlaNH$_2$. According to yet another embodiment, $Xaa_3$ is Acp. According to yet another embodiment, $Xaa_3$ is 6-aminocapramide.

According to one embodiment, the compound of the invention is a compound according to the Formula $X^1$-M-SEQ ID NO:2, or a salt thereof, wherein SEQ ID NO:2 represents $Xaa_1$-Glu-Nva-Val-Ala-Leu-Ser-$Xaa_2$-$Xaa_3$, wherein $Xaa_1$ is zero amino acid or a hydroxylated acyclic amino acid; $Xaa_2$ is Arg or N-MeArg; $Xaa_3$ is selected from the group consisting of bAla, bAlaNH$_2$, Acp and AcpNH$_2$; and, $X^1$-M represents an optional group comprising a tagging element conjugated to the N-terminus of the amino acid sequence SEQ ID NO:2, wherein $X^1$ represents the tagging element, wherein the tagging element is selected from the group consisting of a transduction domain and a detection label; and, -M- represents a single bond or an optional linking group forming a covalent linkage between the tagging element and the amino acid sequence SEQ ID NO:2.

According to another embodiment, the compound of the invention is a compound according to the Formula $X^1$-M-SEQ ID NO:2, or a salt thereof, wherein SEQ ID NO:2 represents $Xaa_1$-Glu-Nva-Val-Ala-Leu-Ser-$Xaa_2$-$Xaa_3$, wherein $Xaa_1$ is selected from the group consisting of zero amino acid, serine, (D)-serine, threonine, (D)-threonine, (L)-allo-threonine, (D)-allo-threonine, (L)-isoserine, (D)-isoserine, (L)-β-homoserine, (D)-β-homoserine, (L)-homoserine, and (D)-homoserine; $Xaa_2$ is Arg or N-MeArg; $Xaa_3$ is selected from the group consisting of bAla, bAlaNH$_2$, Acp and AcpNH$_2$; and, $X^1$-M represents an optional group comprising a tagging element conjugated to the N-terminus of the amino acid sequence SEQ ID NO:2, wherein $X^1$ represents the tagging element, wherein the tagging element is selected from the group consisting of a transduction domain and a detection label; and, -M- represents a single bond or an optional linking group forming a covalent linkage between the tagging element and the amino acid sequence SEQ ID NO:2.

According to yet another embodiment, the compound of the invention is a compound according to the Formula $X^1$-M-SEQ ID NO:2, or a salt thereof, wherein SEQ ID NO:2 represents $Xaa_1$-Glu-Nva-Val-Ala-Leu-Ser-$Xaa_2$-$Xaa_3$, wherein $Xaa_1$ is selected from the group consisting of zero amino acid, serine, (D)-serine, threonine, (D)-threonine, (L)-allo-threonine, and (D)-allo-threonine; $Xaa_2$ is Arg or N-MeArg; $Xaa_3$ is selected from the group consisting of bAla, bAlaNH$_2$, Acp and AcpNH$_2$; and, $X^1$-M represents an optional group comprising a tagging element conjugated to the N-terminus of the amino acid sequence SEQ ID NO:2, wherein $X^1$ represents the tagging element, wherein the tagging element is selected from the group consisting of a transduction domain and a detection label; and, -M- represents a single bond or an optional linking group forming a covalent linkage between the tagging element and the amino acid sequence SEQ ID NO:2.

According to yet another embodiment, the compound of the invention is a compound according to the Formula $X^1$-M-SEQ ID NO:2, or a salt thereof, wherein SEQ ID NO:2 represents $Xaa_1$-Glu-Nva-Val-Ala-Leu-Ser-$Xaa_2$-$Xaa_3$, wherein $Xaa_1$ is selected from the group consisting of zero amino acid, serine, (D)-serine, threonine, (D)-threonine, (L)-allo-threonine, and (D)-allo-threonine; $Xaa_2$ is Arg or N-MeArg; $Xaa_3$ is selected from the group consisting of bAla, bAlaNH$_2$, Acp and AcpNH$_2$; and, $X^1$-M represents an optional group comprising a tagging element conjugated to the N-terminus of the amino acid sequence SEQ ID NO:2, wherein $X^1$ represents the tagging element, wherein the tagging element is selected from the group consisting of a transduction domain and a detection label; and, -M- represents a single bond forming a covalent linkage between the tagging element and the amino acid sequence SEQ ID NO:2.

According to yet another embodiment, the compound of the invention is a compound according to the Formula $X^1$-M-SEQ ID NO:2, or a salt thereof, wherein SEQ ID NO:2 represents a peptide of amino acid sequence selected from the group consisting of Thr-Glu-Nva-Val-Ala-Leu-Ser-Arg-Acp [SEQ ID NO:3], Thr-Glu-Nva-Val-Ala-Leu-Ser-Arg-AcpNH$_2$ [SEQ ID NO:4], (D)-Ser-Glu-Nva-Val-Ala-Leu-Ser-N-MeArg-bAla [SEQ ID NO:5], (D)-Ser-Glu-Nva-Val-Ala-Leu-Ser-N-MeArg-bAlaNH$_2$ [SEQ ID NO:6], Thr-Glu-Nva-Nva-Ala-Leu-Ser-Arg-NvaNH$_2$ [SEQ ID NO:47], alloThr-Glu-Nva-Val-Ala-Leu-Ser-Arg-AcpNH$_2$ [SEQ ID NO:49], Thr-Glu-Nva-Val-Ala-Leu-Ser-Arg-NvaNH$_2$ [SEQ ID NO:50], Glu-Nva-Val-Ala-Leu-Ser-Arg-AcpNH$_2$ [SEQ ID NO:51], and (D)-Ser-Glu-Nva-Val-Ala-Leu-Ser-Arg-AcpNH$_2$ [SEQ ID NO:52]; and, X$^1$-M represents an optional group comprising a tagging element conjugated to the N-terminus of the amino acid sequence SEQ ID NO:2, wherein X$^1$ represents the tagging element, wherein the tagging element is selected from the group consisting of a transduction domain and a detection label; and, -M-represents a single bond forming a covalent linkage between the tagging element and the amino acid sequence SEQ ID NO:2.

According to yet one embodiment, the compound of the invention is the peptide of amino acid sequence Thr-Glu-Nva-Val-Ala-Leu-Ser-Arg-Acp [SEQ ID NO:3], or a salt thereof. According to another embodiment, the compound of the invention is the peptide of amino acid sequence Thr-Glu-Nva-Val-Ala-Leu-Ser-Arg-AcpNH$_2$ [SEQ ID NO:4], or a salt thereof. According to yet another embodiment, the compound of the invention is a peptide of amino acid sequence (D)-Ser-Glu-Nva-Val-Ala-Leu-Ser-N-MeArg-bAla [SEQ ID NO:5], or a salt thereof. According to yet another embodiment, the compound of the invention is the peptide of amino acid sequence (D)-Ser-Glu-Nva-Val-Ala-Leu-Ser-N-MeArg-bAlaNH$_2$ [SEQ ID NO:6], or a salt thereof. According to yet another embodiment, the compound of the invention is the peptide of amino acid sequence Thr-Glu-Nva-Nva-Ala-Leu-Ser-Arg-NvaNH$_2$ [SEQ ID NO:47], or a salt thereof. According to yet another embodiment, the compound of the invention is the peptide of amino acid sequence alloThr-Glu-Nva-Val-Ala-Leu-Ser-Arg-AcpNH$_2$ [SEQ ID NO:49], or a salt thereof. According to yet another embodiment, the compound of the invention is the peptide of amino acid sequence Thr-Glu-Nva-Val-Ala-Leu-Ser-Arg-NvaNH$_2$ [SEQ ID NO:50], or a salt thereof. According to yet another embodiment, the compound of the invention is the peptide of amino acid sequence Glu-Nva-Val-Ala-Leu-Ser-Arg-AcpNH$_2$ [SEQ ID NO:51], or a salt thereof. According to yet another embodiment, the compound of the invention is the peptide of amino acid sequence (D)-Ser-Glu-Nva-Val-Ala-Leu-Ser-Arg-AcpNH$_2$ [SEQ ID NO:52], or a salt thereof.

The invention also includes a pharmaceutical composition comprising a compound according to Formula (I):

$$X^1\text{-M-SEQ ID NO: 2} \quad (I)$$

or a salt thereof, wherein:
SEQ ID NO:2 represents Xaa$_1$-Glu-Nva-Val-Ala-Leu-Ser-Xaa$_2$-Xaa$_3$, wherein:
Xaa$_1$ is zero amino acid or a hydroxylated acyclic amino acid;
Xaa$_2$ is Arg or N-MeArg,
Xaa$_3$ is an aliphatic amino acid; and,
X$^1$-M represents an optional group comprising a tagging element conjugated to the N-terminus of the amino acid sequence SEQ ID NO:2, wherein:
X$^1$ represents the tagging element, wherein the tagging element is selected from the group consisting of a transduction domain and a detection label;
-M- represents a single bond or an optional linking group forming a covalent linkage between the tagging element and the amino acid sequence SEQ ID NO:2;
and a pharmaceutically acceptable carrier.

According to one embodiment, Xaa$_1$ is zero amino acid. According to another embodiment, Xaa$_1$ is a hydroxylated acyclic amino acid selected from the group consisting of serine, (D)-serine, threonine, (D)-threonine, (L)-allo-threonine, (D)-allo-threonine, (L)-isoserine, (D)-isoserine, (L)-β-homoserine, (D)-β-homoserine, (L)-homoserine, and (D)-homoserine. According to yet another embodiment, Xaa$_2$ is Arg. According to yet another embodiment, Xaa$_2$ is N-MeArg. According to yet another embodiment, Xaa$_3$ is bAla. According to yet another embodiment, Xaa$_3$ is bAlaNH$_2$. According to yet another embodiment, Xaa$_3$ is Acp. According to yet another embodiment, Xaa$_3$ is 6-aminocapramide. According to one embodiment, the compound is the peptide of amino acid sequence SEQ ID NO:3, or a salt thereof. According to another embodiment, the compound is the peptide of amino acid sequence SEQ ID NO:4, or a salt thereof. According to yet another embodiment, the compound is the peptide of amino acid sequence SEQ ID NO:5, or a salt thereof. According to yet another embodiment, the compound is the peptide of amino acid sequence SEQ ID NO:6, or a salt thereof. According to yet another embodiment, the compound is the peptide of amino acid sequence SEQ ID NO:47, or a salt thereof. According to yet another embodiment, the compound is the peptide of amino acid sequence SEQ ID NO:49, or a salt thereof. According to yet another embodiment, the compound is the peptide of amino acid sequence SEQ ID NO:50, or a salt thereof. According to yet another embodiment, the compound is the peptide of amino acid sequence SEQ ID NO:51, or a salt thereof. According to yet another embodiment, the compound is the peptide of amino acid sequence SEQ ID NO:52, or a salt thereof.

The invention further includes a method of promoting growth arrest or killing of a leptin-receptor-positive cancer cell in vitro, wherein the method comprises treating the leptin-receptor-positive cancer cell with an effective amount of a pharmaceutical composition comprising a compound according to Formula (I):

$$X^1\text{-M-SEQ ID NO: 2} \quad (I)$$

or a salt thereof, wherein:
SEQ ID NO:2 represents Xaa$_1$-Glu-Nva-Val-Ala-Leu-Ser-Xaa$_2$-Xaa$_3$, wherein:
Xaa$_1$ is zero amino acid or a hydroxylated acyclic amino acid;
Xaa$_2$ is Arg or N-MeArg;
Xaa$_3$ is an aliphatic amino acid; and,
X$^1$-M represents an optional group comprising a tagging element conjugated to the N-terminus of the amino acid sequence SEQ ID NO:2, wherein:
X$^1$ represents the tagging element, wherein the tagging element is selected from the group consisting of a transduction domain and a detection label;
-M- represents a single bond or an optional linking group forming a covalent linkage between the tagging element and the amino acid sequence SEQ ID NO:2;
and a pharmaceutically acceptable carrier.

According to one embodiment, the compound of the invention is the peptide of amino acid sequence SEQ ID NO:3, or a salt thereof. According to another embodiment, the compound of the invention is the peptide of amino acid sequence SEQ ID NO:4, or a salt thereof. According to yet another embodiment, the compound of the invention is the peptide of amino acid sequence SEQ ID NO:5, or a salt thereof. According to yet another embodiment, the compound of the invention is the peptide of amino acid sequence SEQ ID NO:6, or a salt thereof. According to yet another embodiment, the compound is the peptide of amino acid sequence SEQ ID NO:47, or a salt thereof. According to yet another embodiment, the compound is the peptide of amino acid sequence SEQ ID NO:49, or a salt thereof. According to yet another embodiment, the compound is the peptide of amino acid sequence SEQ ID NO:50, or a salt thereof. According to yet another embodiment, the compound is the peptide of amino acid sequence SEQ ID NO:51, or a salt thereof. According to yet another embodiment, the compound is the peptide of amino acid sequence SEQ ID NO:52, or a salt thereof.

The invention also includes a method of promoting growth arrest or killing of leptin receptor-positive cancer cells in a subject in need thereof, wherein the method comprises administering to the subject an effective amount of a pharmaceutical composition comprising a compound according to Formula (I):

$$X^1\text{-M-SEQ ID NO: 2} \quad (I)$$

or a salt thereof, wherein:
SEQ ID NO:2 represents $Xaa_1$-Glu-Nva-Val-Ala-Leu-Ser-$Xaa_2$-$Xaa_3$, wherein:
$Xaa_1$ is zero amino acid or a hydroxylated acyclic amino acid;
$Xaa_2$ is Arg or N-MeArg;
$Xaa_3$ is an aliphatic amino acid; and,
$X^1$-M represents an optional group comprising a tagging element conjugated to the N-terminus of the amino acid sequence SEQ ID NO:2, wherein:
$X^1$ represents the tagging element, wherein the tagging element is selected from the group consisting of a transduction domain and a detection label;
-M- represents a single bond or an optional linking group forming a covalent linkage between the tagging element and the amino acid sequence SEQ ID NO:2;
and a pharmaceutically acceptable carrier.

According to one embodiment, the compound of the invention is the peptide of amino acid sequence SEQ ID NO:3, or a salt thereof. According to another embodiment, the compound of the invention is the peptide of amino acid sequence SEQ ID NO:4, or a salt thereof. According to yet another embodiment, the compound of the invention is the peptide of amino acid sequence SEQ ID NO:5, or a salt thereof. According to yet another embodiment, the compound of the invention is the peptide of amino acid sequence SEQ ID NO:6, or a salt thereof. According to yet another embodiment, the compound is the peptide of amino acid sequence SEQ ID NO:47, or a salt thereof. According to yet another embodiment, the compound is the peptide of amino acid sequence SEQ ID NO:49, or a salt thereof. According to yet another embodiment, the compound is the peptide of amino acid sequence SEQ ID NO:50, or a salt thereof. According to yet another embodiment, the compound is the peptide of amino acid sequence SEQ ID NO:51, or a salt thereof. According to yet another embodiment, the compound is the peptide of amino acid sequence SEQ ID NO:52, or a salt thereof.

According to one embodiment of the invention, the leptin receptor-positive cells are associated with a cancer selected from the group consisting of glioma, breast cancer, colorectal cancer, prostate cancer, pancreatic cancer, ovarian cancer, endometric cancer and lung cancer. According to another embodiment, the composition is administered parenterally. According to yet another embodiment, the composition is administered orally. According to yet another embodiment, the composition is administered intranasally. According to yet another embodiment, the subject is human.

The invention also includes a method of monitoring or detecting a leptin receptor-positive cell in vitro or in vivo, comprising the steps of:
contacting said leptin-receptor-positive cancer cell with an effective amount of a pharmaceutical composition comprising a compound according to Formula (II):

$$X^1\text{-M-SEQ ID NO: 2} \quad (I)$$

or a salt thereof, wherein:
SEQ ID NO:2 represents $Xaa_1$-Glu-Nva-Val-Ala-Leu-Ser-$Xaa_2$-$Xaa_3$, wherein:
$Xaa_1$ is zero amino acid or a hydroxylated acyclic amino acid;
$Xaa_2$ is Arg or N-MeArg;
$Xaa_3$ is an aliphatic amino acid; and,
$X^1$-M represents an optional group comprising a tagging element conjugated to the N-terminus of the amino acid sequence SEQ ID NO:2, wherein:
$X^1$ represents the tagging element, wherein the tagging element is selected from the group consisting of a transduction domain and a detection label;
-M- represents a single bond or an optional linking group forming a covalent linkage between the tagging element and the amino acid sequence SEQ ID NO:2;
and a pharmaceutically acceptable carrier; and
evaluating binding of the compound of Formula (I) to the leptin-receptor-positive cancer cell.

According to one embodiment of the invention, said binding is evaluated by fluorescence.

The invention also includes a method of treating a weight-loss nutritional disorder in a subject in need thereof, wherein the method comprises administering to the subject an effective amount of a pharmaceutical composition comprising a compound according to Formula (I):

$$X^1\text{-M-SEQ ID NO: 2} \quad (I)$$

or a salt thereof, wherein:
SEQ ID NO:2 represents $Xaa_1$-Glu-Nva-Val-Ala-Leu-Ser-$Xaa_2$-$Xaa_3$, wherein:
$Xaa_1$ is zero amino acid or a hydroxylated acyclic amino acid;
$Xaa_2$ is Arg or N-MeArg;
$Xaa_3$ is an aliphatic amino acid; and,
$X^1$-M represents an optional group comprising a tagging element conjugated to the N-terminus of the amino acid sequence SEQ ID NO:2, wherein:
$X^1$ represents the tagging element, wherein the tagging element is selected from the group consisting of a transduction domain and a detection label;
-M- represents a single bond or an optional linking group forming a covalent linkage between the tagging element and the amino acid sequence SEQ ID NO:2;
and a pharmaceutically acceptable carrier.

According to one embodiment of the invention, the weight-loss nutritional disorder is cachexia. According to another embodiment of the invention, the weight-loss nutritional disorder is wasting. According to another embodiment, the composition is administered parenterally. According to yet another embodiment, the composition is administered orally. According to yet another embodiment, the composition is administered intranasally. According to yet another embodiment, the subject is human.

The invention also includes a method of treating osteoporosis in a subject in need thereof, wherein the method comprises administering to the subject an effective amount of a pharmaceutical composition comprising a compound according to Formula (I):

$$X^1\text{-M-SEQ ID NO: 2} \qquad (I)$$

or a salt thereof, wherein:
SEQ ID NO:2 represents $Xaa_1$-Glu-Nva-Val-Ala-Leu-Ser-$Xaa_2$-$Xaa_3$, wherein:
$Xaa_1$ is zero amino acid or a hydroxylated acyclic amino acid;
$Xaa_2$ is Arg or N-MeArg;
$Xaa_3$ is an aliphatic amino acid; and,
$X^1$-M represents an optional group comprising a tagging element conjugated to the N-terminus of the amino acid sequence SEQ ID NO:2, wherein:
$X^1$ represents the tagging element, wherein the tagging element is selected from the group consisting of a transduction domain and a detection label;
-M- represents a single bond or an optional linking group forming a covalent linkage between the tagging element and the amino acid sequence SEQ ID NO:2;
and a pharmaceutically acceptable carrier.

The invention also includes a method of treating rheumatoid arthritis in a subject in need thereof, wherein the method comprises administering to the subject an effective amount of a pharmaceutical composition comprising a compound according to Formula (I):

$$X^1\text{-M-SEQ ID NO: 2} \qquad (I)$$

or a salt thereof, wherein:
SEQ ID NO:2 represents $Xaa_1$-Glu-Nva-Val-Ala-Leu-Ser-$Xaa_2$-$Xaa_3$, wherein:
$Xaa_1$ is zero amino acid or a hydroxylated acyclic amino acid;
$Xaa_2$ is Arg or N-MeArg,
$Xaa_3$ is an aliphatic amino acid; and,
$X^1$-M represents an optional group comprising a tagging element conjugated to the N-terminus of the amino acid sequence SEQ ID NO:2, wherein:
$X^1$ represents the tagging element, wherein the tagging element is selected from the group consisting of a transduction domain and a detection label;
-M- represents a single bond or an optional linking group forming a covalent linkage between the tagging element and the amino acid sequence SEQ ID NO:2;
and a pharmaceutically acceptable carrier.

The invention also includes a method of treating osteoarthritis in a subject in need thereof, wherein the method comprises administering to the subject an effective amount of a pharmaceutical composition comprising a compound according to Formula (I):

$$X^1\text{-M-SEQ ID NO: 2} \qquad (I)$$

or a salt thereof, wherein:
SEQ ID NO:2 represents $Xaa_1$-Glu-Nva-Val-Ala-Leu-Ser-$Xaa_2$-$Xaa_3$, wherein:
$Xaa_1$ is zero amino acid or a hydroxylated acyclic amino acid;
$Xaa_2$ is Arg or N-MeArg;
$Xaa_3$ is an aliphatic amino acid; and,
$X^1$-M represents an optional group comprising a tagging element conjugated to the N-terminus of the amino acid sequence SEQ ID NO:2, wherein:
$X^1$ represents the tagging element, wherein the tagging element is selected from the group consisting of a transduction domain and a detection label;
-M- represents a single bond or an optional linking group forming a covalent linkage between the tagging element and the amino acid sequence SEQ ID NO:2;
and a pharmaceutically acceptable carrier.

The invention also includes a method of treating inflammatory bowel disease in a subject in need thereof, wherein the method comprises administering to the subject an effective amount of a pharmaceutical composition comprising a compound according to Formula (I):

$$X^1\text{-M-SEQ ID NO: 2} \qquad (I)$$

or a salt thereof, wherein:
SEQ ID NO:2 represents $Xaa_1$-Glu-Nva-Val-Ala-Leu-Ser-$Xaa_2$-$Xaa_3$, wherein:
$Xaa_1$ is zero amino acid or a hydroxylated acyclic amino acid;
$Xaa_2$ is Arg or N-MeArg;
$Xaa_3$ is an aliphatic amino acid; and,
$X^1$-M represents an optional group comprising a tagging element conjugated to the N-terminus of the amino acid sequence SEQ ID NO:2, wherein:
$X^1$ represents the tagging element, wherein the tagging element is selected from the group consisting of a transduction domain and a detection label;
-M- represents a single bond or an optional linking group forming a covalent linkage between the tagging element and the amino acid sequence SEQ ID NO:2;
and a pharmaceutically acceptable carrier.

According to one embodiment, the inflammatory bowel disease is selected from the group consisting of Crohn's disease (CD), ulcerative colitis (UC), indeterminate colitis and infectious colitis.

According to another embodiment, the composition is administered parenterally. According to yet another embodiment, the composition is administered orally. According to yet another embodiment, the composition is administered intranasally. According to yet another embodiment, the subject is human.

The invention further relates to a compound according to Formula (I):

$$X^1\text{-M-SEQ ID NO: 2} \qquad (I)$$

or a salt thereof, wherein:
SEQ ID NO:2 represents $Xaa_1$-Glu-Nva-Val-Ala-Leu-Ser-$Xaa_2$-$Xaa_3$, wherein:
$Xaa_1$ is zero amino acid or a hydroxylated acyclic amino acid;
$Xaa_2$ is Arg or N-MeArg;
$Xaa_3$ is an aliphatic amino acid; and,
$X^1$-M represents an optional group comprising a tagging element conjugated to the N-terminus of the amino acid sequence SEQ ID NO:2, wherein:
$X^1$ represents the tagging element, wherein the tagging element is selected from the group consisting of a transduction domain and a detection label;

-M- represents a single bond or an optional linking group forming a covalent linkage between the tagging element and the amino acid sequence SEQ ID NO:2;

for use in the treatment of osteoporosis, a weight-loss nutritional disorder, a leptin receptor-positive cancer, rheumatoid arthritis, osteoarthritis or inflammatory bowel disease.

In another embodiment, the aforementioned peptide is used for preparation of a medicament for the treatment of osteoporosis, a weight-loss nutritional disorder, a leptin receptor-positive cancer, rheumatoid arthritis, osteoarthritis or inflammatory bowel disease.

As envisioned in the present invention with respect to the disclosed compositions of matter and methods, in one aspect the embodiments of the invention comprise the components and/or steps disclosed therein. In another aspect, the embodiments of the invention consist essentially of the components and/or steps disclosed therein. In yet another aspect, the embodiments of the invention consist of the components and/or steps disclosed therein.

DESCRIPTION OF FIGURES

FIGS. 6A-6D, shows the in vivo properties of the peptide of amino acid sequence SEQ ID NO:49. FIG. 6A shows the biodistribution of Alexa 680-labeled peptide of amino acid sequence SEQ ID NO:49 in Balb/c mice at 70 min following intraperitoneal administration. FIGS. 6B-6D show reduction of MCF-7 human breast cancer xenograft growth in scid mice. FIG. 6B shows tumor volume on day 51 (38 days after treatment initiation). FIG. 6C shows mice bearing tumor xenografts on day 52 and left untreated. FIG. 6D shows mice on day 52 (39 days after treatment initiation) treated with 0.1 mg/kg/day peptide subcutaneously between the two lesions.

FIGS. 7A-7C, shows the effects of peptides of the invention on the central nervous system, as represented by accelerated weight gain of growing animals. FIG. 7A shows the comparison of a partial agonist (peptide of amino acid sequence SEQ ID NO:54) and full antagonist (peptide of amino acid sequence SEQ ID NO:4) on the weight gain of mice. FIG. 7B shows the percentage of body weight increase (relative to that of untreated animals) following various administration routes of the peptide of amino acid sequence NO:4 into mice. FIG. 7C shows body mass increase in rats upon intranasal (in) peptide addition. The treated animals are shown as solid symbols, and untreated controls are shown as open symbols.

DEFINITIONS

Figure 1:
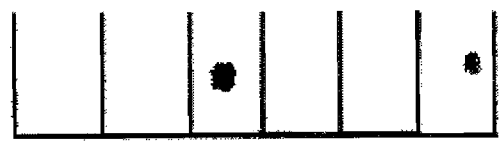
FIG. 1 shows the binding of leptin fragments and derivatives to the extracellular domain of the leptin receptor (ObR), as assessed by dot-blot. Samples 1-4 are representative members of a peptide library. Sample 3 corresponds to the peptide of amino acid sequence SEQ ID NO:4. Sample 5 is a negative control antibacterial peptide (A3-APO) [SEQ ID NO:7]. Sample 6 is the positive control peptide to this screening assay [SEQ ID NO:8].

The definitions used in this application are for illustrative purposes and do not limit the scope used in the practice of the invention.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, protein chemistry and nucleic acid chemistry and hybridization are those well known and commonly employed in the art.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

As used herein, the terms "peptide," "polypeptide," or "protein" are used interchangeably, and refer to a compound comprised of amino acid residues covalently linked by peptide bonds. A protein or peptide must contain at least two amino acids, and no limitation is placed on the maximum number of amino acids that can comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs and fusion proteins, among others. The polypeptides include natural peptides, recombinant peptides, synthetic peptides or a combination thereof. A peptide that is not cyclic will have an N-terminus and a C-terminus. The N-terminus will have an amino group, which may be free (i.e., as a NH$_2$ group) or appropriately protected (for example, with a BOC or a Fmoc group). The C-terminus will have a carboxylic group, which may be free (i.e., as a COOH group) or appropriately protected (for example, as a benzyl or a methyl ester). A cyclic peptide does not necessarily have free N- or C-termini, since they are covalently bonded through an amide bond to form the cyclic structure. The term "peptide bond" means a covalent amide linkage formed by loss of a molecule of water between the carboxyl group of one amino acid and the amino group of a second amino acid.

As used herein, the term "fragment," as applied to a protein or peptide, refers to a subsequence of a larger protein or peptide. A "fragment" of a protein or peptide can be at least about 10 amino acids in length; for example, at least about 50 amino acids in length; more preferably, at least about 100 amino acids in length; even more preferably, at least about 200 amino acids in length; particularly preferably, at least about 300 amino acids in length; and most preferably, at least about 400 amino acids in length.

As used herein, amino acids are represented by the full name thereof, by the three-letter code, as well as the one-letter code corresponding thereto, as shown in the table below. The structure of amino acids and their abbreviations can be found in the chemical literature, such as in Stryer, 1988, "Biochemistry", $3^{rd}$ Ed., W. H. Freeman & Co., NY, N.Y.

| Full Name | Three-Letter Code | One-Letter Code |
|---|---|---|
| Alanine | Ala | A |
| Arginine | Arg | R |
| Asparagine | Asn | N |
| Aspartic Acid | Asp | D |
| Cysteine | Cys | C |
| Cystine | Cys-Cys | C-C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Nva corresponds to the non-natural amino acid norvaline, also known as 2(L)-aminopentanoic acid. $NvaNH_2$ corresponds to 2(L)-aminopentanamide. Acp corresponds to the non-natural amino acid 6-aminocaproic acid, also known as 6-amino-hexanoic acid. $AcpNH_2$ corresponds to 6-aminocapramide, also known as 6-amino-hexanamide. Dpr(Ac) corresponds to N2(3)-acetyl-diaminopropionic acid. Dbu corresponds to 2,4-diaminobutyric acid. Glc corresponds to glucose. βGlc corresponds to beta-glucose. Serβ(Glc) corresponds to serine glycosylated with a beta-glucosyl residue on the alcohol hydroxyl group. Thr(NAcGal) corresponds to threonine glycosylated with an N-acetyl galactosaminyl residue on the alcohol hydroxyl group. $Tyr(I_2)$ corresponds to 3,5-diiodotyrosine. N-MeArg corresponds to N-methyl-arginine. bAla corresponds to beta-alanine, also known as 3-aminopropanoic acid. $bAlaNH_2$ corresponds to the amide derivative of beta-alanine, also known as 3-aminopropanamide. (D)-Ser corresponds to D-serine. Apa corresponds to aminopentanoic acid. AlloThr corresponds to allo-threonine, also known as (2S,3S)-2-amino-3-hydroxybutanoic acid. 3Hyp corresponds to 3-hydroxyproline. 4Hyp corresponds to 4-hydroxyproline.

As used herein, the term "hydroxylated acyclic amino acid" refers to an acyclic amino acid that contains at least one alcohol hydroxyl group in its structure. Preferred, but non-limiting, examples of hydroxylated acyclic amino acid are serine, (D)-serine, threonine, (D)-threonine, (L)-allo-threonine, (D)-allo-threonine, (L)-isoserine, (D)-isoserine, (L)-β-homoserine, (D)-β-homoserine, (L)-homoserine, and (D)-homoserine.

As used herein, the term "aliphatic amino acid" refers to an amino acid which carbon chain is aliphatic in nature. Non-limiting examples of aliphatic amino acids are alanine, arginine, asparagine, aspartic acid, cysteine, glutamic acid, glutamine, glycine, isoleucine, leucine, lysine, methionine, proline, serine, threonine, valine, Nva, $NvaNH_2$, Acp, $AcpNH_2$, Dpr(Ac), Dbu, N-MeArg, bAla, $bAlaNH_2$, Apa, and AlloThr. Preferred aliphatic amino acids within the present application are bAla, $bAlaNH_2$, Acp and $AcpNH_2$.

As used herein, the term "ObR" refers to a leptin receptor, also known as LEPR and CD295 (cluster of differentiation 295). The human transmembrane receptor has at least four different isoforms with different C-terminus cytoplasmatic domains (Barr et al., 1999, J. Biol. Chem. 274 (30): 21416-21424). The full form of ObR (ObR1) is 1,165 amino acids long and contains extracellular, transmembrane and intracellular domains (SEQ ID NO:56, from mRNA). The extracellular domain binds ligand, whereas the intracellular tail recruits and activates signaling substrates. ObR1 has full signaling potential, as opposed to the shorter ObR isoforms.

As used herein, the term "leptin receptor-positive cell" refers to a cell that expresses on its surface an isoform of the leptin receptor, which is able to bind leptin or any leptin receptor binder.

As used herein, the term "translocation domain" refers to a peptide, or derivative thereof, that is capable of crossing cell membranes and of directing the transport of a peptide, protein, or molecule associated with the protein transduction domain, from the outside of a cell into the cytoplasm of the cell through the cytoplasmic membrane of the cell.

As used herein, the term "detection label" refers to a chemical moiety that, once attached to a peptide of the invention, allows for the detection and/or quantitation of the peptide based on an intrinsic and detectable property of the moiety. Non-limiting examples of intrinsic and detectable property within the invention are fluorescence, radioactivity, emission of radiowaves, and magnetism. The preferred example of intrinsic and detectable property within the invention is fluorescence.

As used herein, the term "conjugated" referring to the linking of two molecules means that the two molecules are covalently linked to one another through the formation of an amide bond between the carboxyl group of one molecules and an amino group of the other molecule, or by means of a linking group wherein the linking group has covalent bonds to each of the molecules. For example, the linking group may be a peptide chain, an amino acid, or any group having at least two functional groups and capable of forming covalent bond to each of the two molecules.

As used herein, the term "obesity" is defined as excess body mass. The World Health Organization (WHO) classifies body mass (Kopelman, 2000, Nature 404: 635-643) according body mass index (BMI, weight kg/height $m^2$) as follows: BMI less than 18.5, underweight; BMI of 18.5-24.9, normal; BMI of 25.0-29.9, overweight (grade 1); BMI of 30-39.9, obese (grade 2); BMI equal to or greater than 40, morbidly obese (grade 3). As used herein, "obesity" refers to both obesity and morbid obesity as defined by the WHO.

As used herein, the term "weight-loss nutritional disorder" as applied to an individual refers to a nutritional disorder where the individual is incapable of maintaining the ideal body weight (for example, BMI less than 18.5, or any another BMI range defined by a medical specialist) or loses considerable amount of body weight, without actually attempting to reduce body weight. In a preferred embodiment of the invention, the weight-loss nutritional disorder is cachexia. In another preferred embodiment of the invention, the weight-loss nutritional disorder is wasting.

As used herein, the term "osteoporosis" refers to a disease of bone that leads to an increased risk of fracture. In osteoporosis, the bone mineral density (BMD) is reduced, bone micro-architecture is disrupted, and the amount and variety of non-collagenous proteins in bone is altered. Osteoporosis is defined by the World Health Organization (WHO) in women as a bone mineral density 2.5 standard deviations below peak bone mass (20-year-old healthy female average) as measured by dual energy X-ray absorptiometry. Osteoporosis is most common in women after menopause (postmenopausal osteoporosis) but may also develop in men, and may occur in anyone in the presence of particular hormonal disorders and other chronic diseases or as a result of medications, specifically glucocorticoids, when the disease is called steroid- or glucocorticoid-induced osteoporosis (SIOP or GIOP).

As used herein, the term "rheumatoid arthritis" or RA refers to a chronic, systemic inflammatory disorder that may affect many tissues and organs, but principally attacks the joints producing an inflammatory synovitis that often progresses to destruction of the articular cartilage and ankylosis of the joints.

As used herein, the term "osteoarthritis," "OA," "degenerative arthritis," or "degenerative joint disease" is a group of diseases and mechanical abnormalities involving degradation of joints, including articular cartilage and the subchondral bone next to it.

As used herein, the term "inflammatory bowel disease" or "IBS" refers to chronic recurrent inflammatory diseases of unclear etiology (and thus classified as "idiopathic"), affecting the small intestine and colon. In one embodiment, the inflammatory bowel disease is Crohn's disease, ulcerative colitis, indeterminate colitis or infectious colitis.

As used herein, "isolated" means altered or removed from the natural state through the actions of a human being. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as a host cell for example.

"Biologically active," as used herein with respect to a peptide of the invention, means that the peptide of the invention have the ability to bind and act as an antagonist to a leptin receptor. The term "inhibit," as used herein, means to suppress or block an activity or function by at least about ten percent relative to a control value. Preferably, the activity is suppressed or blocked by 50% compared to a control value, more preferably by 75%, and even more preferably by 95%.

"Treating", as used herein, means ameliorating the effects of, or delaying, halting or reversing the progress of a disease or disorder. The word encompasses reducing the severity of a symptom of a disease or disorder and/or the frequency of a symptom of a disease or disorder.

"Medical intervention", as used herein, means a set of one or more medical procedures or treatments that are required for ameliorating the effects of, delaying, halting or reversing a disease or disorder of a subject. A medical intervention may involve surgical procedures or not, depending on the disease or disorder in question. A medical intervention may be wholly or partially performed by a medical specialist, or may be wholly or partially performed by the subject himself or herself, if capable, under the supervision of a medical specialist or according to literature or protocols provided by the medical specialist.

A "subject", as used therein, can be a human or non-human animal. Non-human animals include, for example, livestock and pets, such as ovine, bovine, porcine, canine, feline and murine mammals, as well as reptiles, birds and fish. Preferably, the subject is human.

The language "effective amount" or "therapeutically effective amount" refers to a nontoxic but sufficient amount of the composition used in the practice of the invention that is effective to promote the required growth arrest or killing of cancer cells in a subject, or is effective to treat a weight-loss nutritional disorder in a subject, or is effective to treat osteoporosis in a subject. The desired treatment may be prophylactic and/or therapeutic. That result can be reduction and/or alleviation of the signs, symptoms, or causes of a disease or disorder, or any other desired alteration of a biological system. An appropriate therapeutic amount in any individual case may be determined by one of ordinary skill in the art using routine experimentation.

A "prophylactic" or "preventive" treatment is a treatment administered to a subject who does not exhibit signs of a disease or disorder, or exhibits only early signs of the disease or disorder, for the purpose of decreasing the risk of developing pathology associated with the disease or disorder.

A "therapeutic" treatment is a treatment administered to a subject who exhibits signs of pathology of a disease or disorder for the purpose of diminishing or eliminating those signs.

"Pharmaceutically acceptable carrier" refers herein to a composition suitable for delivering an active pharmaceutical ingredient, such as a compound of the present invention, to a subject without excessive toxicity or other complications while maintaining the biological activity of the active pharmaceutical ingredient. Protein-stabilizing excipients, such as mannitol, sucrose, polysorbate-80 and phosphate buffers, are typically found in such carriers, although the carriers should not be construed as being limited only to these compounds.

As used herein with respect to formulations, the term "additional ingredients" includes, but is not limited to, one or more of the following: excipients, surface active agents, dispersing agents, inert diluents, granulating and disintegrating agents, binding agents, lubricating agents, sweetening agents, flavoring agents, coloring agents, preservatives, physiologically degradable compositions such as gelatin, aqueous vehicles and solvents, oily vehicles and solvents, suspending agents, dispersing or wetting agents, emulsifying agents, demulcents, buffers, salts, thickening agents, fillers, emulsifying agents, antioxidants, antibiotics, antifungal agents, stabilizing agents and pharmaceutically acceptable polymeric or hydrophobic materials. Other "additional ingredients" that may be included in the pharmaceutical compositions used in the practice of the invention are known in the art and described, for example in Remington's Pharmaceutical Sciences (Genaro, ed. Mack Publishing Co., 1985, Easton, Pa.), which is incorporated herein by reference.

"Container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions can contain information pertaining to the compound's ability to perform its intended function, e.g., causing growth arrest or death of cancerous cells in a subject.

"Applicator," as the term is used herein, is used to identify any device including, but not limited to, a hypodermic syringe, a pipette, and the like, for administering the compounds and compositions used in the practice of the invention.

DETAILED DESCRIPTION OF INVENTION

The present invention is based on the unexpected discovery that certain leptin-based peptides act as pure antagonists of the leptin receptor (ObR), both in the presence and absence of external leptin protein or other leptin receptor binders. The peptides of the invention bind to the leptin receptor and inhibit downstream signaling. The binding of the peptides of the invention to the leptin receptor has the effect of inhibiting leptin's role as a food intake regulator, mitogen, metabolic regulator and/or pro-angiogenic factor. Therefore, the peptides of the invention may find use in promoting growth arrest or killing of leptin-receptor-positive cancerous cells in vitro or in vivo. The peptides of the invention may also find use in monitoring or detecting a leptin receptor-positive cell in vitro or in vivo. The peptides may also find use in treating a weight-loss nutritional disorder in vivo. The peptides may also find use in treating osteoporosis in vivo. The peptides may also find use in treating rheumatoid arthritis in vivo. The peptides may also find use in treating osteoarthritis in vivo. The peptides may also find use in treating inflammatory bowel disease in vivo.

According to the experiments discussed herein, peptides of the invention bind tightly to the leptin receptor. The peptides of the invention antagonize leptin action in ObR-positive cell lines, while not affecting the growth of ObR-negative cells.

Compounds of the Invention

As one aspect of the invention, there is provided a compound according to Formula (I):

$$X^1\text{-M-SEQ ID NO: 2} \quad (I)$$

or a salt thereof, wherein:
SEQ ID NO:2 represents $Xaa_1$-Glu-Nva-Val-Ala-Leu-Ser-$Xaa_2$-$Xaa_3$, wherein:
  $Xaa_1$ is zero amino acid or a hydroxylated acyclic amino acid;
  $Xaa_2$ is Arg or N-MeArg;
  $Xaa_3$ is an aliphatic amino acid; and,
$X^1$-M represents an optional group comprising a tagging element conjugated to the N-terminus of the amino acid sequence SEQ ID NO:2, wherein:
  $X^1$ represents the tagging element, wherein the tagging element is selected from the group consisting of a transduction domain and a detection label;
  -M- represents a single bond or an optional linking group forming a covalent linkage between the tagging element and the amino acid sequence SEQ ID NO:2.

In a preferred embodiment, the compound of the invention is the peptide of amino acid sequence Thr-Glu-Nva-Val-Ala-Leu-Ser-Arg-Acp [SEQ ID NO:3], or a salt thereof. In another preferred embodiment, the compound of the invention is the peptide of amino acid sequence Thr-Glu-Nva-Val-Ala-Leu-Ser-Arg-AcpNH$_2$ [SEQ ID NO:4], or a salt thereof. In yet another preferred embodiment, the compound of the invention is the peptide of amino acid sequence (D)-Ser-Glu-Nva-Val-Ala-Leu-Ser-N-MeArg-bAla [SEQ ID NO:5], or a salt thereof. In yet another preferred embodiment, the compound of the invention is the peptide of amino acid sequence (D)-Ser-Glu-Nva-Val-Ala-Leu-Ser-N-MeArg-bAlaNH$_2$ [SEQ ID NO:6], or a salt thereof. According to yet another embodiment, the compound of the invention is the peptide of amino acid sequence Thr-Glu-Nva-Nva-Ala-Leu-Ser-Arg-NvaNH$_2$ [SEQ ID NO:47]. According to yet another embodiment, the compound of the invention is the peptide of amino acid sequence alloThr-Glu-Nva-Val-Ala-Leu-Ser-Arg-AcpNH$_2$ [SEQ ID NO:49]. According to yet another embodiment, the compound of the invention is the peptide of amino acid sequence Thr-Glu-Nva-Val-Ala-Leu-Ser-Arg-NvaNH$_2$ [SEQ ID NO:50]. According to yet another embodiment, the compound of the invention is the peptide of amino acid sequence Glu-Nva-Val-Ala-Leu-Ser-Arg-AcpNH$_2$ [SEQ ID NO:51]. According to yet another embodiment, the compound of the invention is the peptide of amino acid sequence (D)-Ser-Glu-Nva-Val-Ala-Leu-Ser-Arg-AcpNH$_2$ [SEQ ID NO:52].

When it is stated that "$X^1$-M- represents an optional group", it is meant that the formula (I) is intended to encompass both a compound of the formula $X^1$-M- SEQ ID NO:2 or a salt thereof, where the amino acid sequence SEQ ID NO:2 is conjugated to a tagging element, as well as the peptide consisting of the amino acid sequence SEQ ID NO:2 or a salt thereof, which is not conjugated to a tagging element.

Synthesis of the Compounds of the Invention.

The compounds of the invention may be prepared by methods known to the person skilled in the art of peptide and organic synthesis. Peptides of the present invention may be natural peptides, recombinant peptides or synthetic peptides. They may also be chemically synthesized, using, for example, solid phase synthesis methods. Transduction domains appended to peptides of the invention may be natural or synthetic peptides, may be non-peptidic moieties, and may be either prepared by isolation from natural sources or may be synthesized.

The peptides of the present invention may be synthesized de novo using peptide synthesis methods. In such methods, the peptide chain is prepared by a series of coupling reactions in which the constituent amino acids are added to the growing peptide chain in the desired sequence. The use of various N-protecting groups, e.g., the carbobenzoxy group or the t-butoxycarbonyl group; various coupling reagents e.g., dicyclohexylcarbodiimide or carbonyldiimidazole; various active esters, e.g., esters of N-hydroxyphthalimide or N-hydroxysuccinimide; and the various cleavage reagents, e.g., trifluoroacetic acid (TFA), HCl in dioxane, boron tris(trifluoroacetate) and cyanogen bromide; and reaction in solution with isolation and purification of intermediates are methods well-known to those of ordinary skill in the art. The reaction may be carried out with the peptide either in solution or attached to a solid phase support. In the solid phase method, the peptide is released from the solid phase support following completion of the synthesis.

In an embodiment, peptide synthesis method may follow Merrifield solid-phase procedures. See Merrifield, 1963, J. Am. Chem. Soc. 85: 2149-54 and Merrifield, 1965, Science 50: 178-85. Additional information about the-solid phase synthetic procedure can be obtained from the treatises: Atherton & Sheppard, 1989, "Solid Phase Peptide Synthesis: A Practical Approach", Oxford University Press, NY, N.Y.;

Stewart & Young, 1984, "Solid phase peptide synthesis", 2nd edition, Pierce Chemical Company, Rockford, Ill.; and the review chapters by R. Merrifield, 1969, Adv. Enzymol. 32: 221-296, and by B. W. Erickson and R. Merrifield, 1976, in "The Proteins", Vol. 2, pp. 255 et seq., edited by Neurath and Hill, Academic Press, NYC, N.Y. Peptide synthesis may follow synthetic techniques such as those set forth in Fields et al., 2008, "Introduction to Peptide Synthesis", in "Current Protocols in Molecular Biology", Chapter 11, Unit 11.15, John Wiley and Sons, Hoboken, N.J., and Amblard et al., 2006, Molecular Biotechnology 33: 239-254.

The synthesis of peptides by solution methods is described in "The Proteins", $3^{rd}$ Edition, Vol. 11, Neurath et al., Eds., Academic Press, St. Louis, Mo., 1976). Other general references to the synthesis of peptides include: "Peptide Synthesis Protocols", 1994, edited by M. W. Pennington and Ben M. Dunn, Humana Press, Totowa, N.J.; Bodanszky, 1993, "Principles of Peptide Synthesis", 2" edition, Springer-Verlag, NYC, N.Y.; Lloyd-Williams et al., 1997, "Chemical Approaches to the Synthesis of Peptides and Proteins", CRC Press, Boca Raton, Fla.; and "Synthetic Peptides: A User's Guide", G. Grant, Ed., Oxford University Press, NY, N.Y., 2002.

Compounds of Formula (I) wherein the linker -M- is other than a peptide chain may be prepared, for example, by coupling the tagging element and the suitable linking molecule using methods that will vary according to the exact nature of the compound but will be apparent to the person skilled in the art. Suitable protecting group strategies may be employed in order to achieve the desired selectivity of the site of coupling, as described, for example, in "Protective Groups in Organic Synthesis", by T. W. Greene and P. G. M. Wuts (3rd Edition, Wiley, 1999).

Linking Groups and Tagging Elements.

The compounds of the invention may or may not have the ability to cross the blood brain barrier, depending on their intrinsic properties. Determination of ability of the compounds of the invention to penetrate the blood brain barrier may be easily performed using standard techniques such as those cited in Bernacki et al., 2008, Pharmacol. Rep. 60 (5): 600-22.

In the case that the compound of the invention has low or nearly inexistent ability to penetrate the blood brain barrier, the activity of the compound of the invention may not be felt in receptors located in various parts of the brain. This may limit the action of the compound to those receptors located outside of the central nervous system. In that case, the compound of the invention finds use in the treatment of cancers that occur in peripheral systems, such as breast cancer, colorectal cancer, prostate cancer, pancreatic cancer, ovarian cancer, endometric cancer and lung cancer.

In the case that the compound of the invention has significant ability to penetrate the blood brain barrier, the activity of the compound may be felt in receptors located in various parts of the brain. In this case, the compound may be active against receptors located both inside and outside the central nervous system. In that case, the compound of the invention finds use in the treatment of weight-loss nutritional disorders, such as cachexia and wasting, and cancers, such as glioma, breast cancer, colorectal cancer, prostate cancer, pancreatic cancer, ovarian cancer, endometric cancer and lung cancer.

The ability of the compound of the invention to cross the blood brain barrier may be enhanced when it comprises a transduction domain as the tagging element ($X^1$). The transduction domain improves the ability of the construct to cross the cell membrane (see PCT Application WO 2008/070049, incorporated by reference herein in its entirety). Such transduction domain may be a peptide selected for its known membrane-crossing properties.

The compounds of the invention may also benefit from the property of being easily monitored or detected in vitro or in vivo. In vitro, the monitoring or detection of the compounds of the invention would allow one skilled in the art to identify whether and/or which cells under observation contain leptin receptors, and to follow the binding of the compounds of the invention to such leptin receptor-positive cells. In vivo, the monitoring or detection of the compounds of the invention would allow one skilled in the art to determine whether/or which the tissues under observation contain leptin-receptor positive cells and to evaluate the biodistribution of the peptides dose in an individual. In one embodiment, the compound of the invention binds to the leptin receptor-positive cell and the binding is evaluated by measuring the change in a specified physical property of the compound of the invention once it binds to the cell. Non-limiting physical properties contemplated within the invention include UV-vis absorption; IR absorption; $^1H$, $^{13}C$ or $^{15}N$ NMR signals or relaxation; fluorescence; and magnetic properties.

The ability of detecting a compound of the invention, in either an unbound or a bound form, may be enhanced when the compound of the invention comprises a detection label as the tagging element ($X^1$). In this case, cells that present leptin receptors on their surfaces may bind the peptide of the invention and the detection label may be used to monitor the binding or identify the position of the leptin receptor-containing cells. The method used to monitor such phenomena is dependent on the specific nature of the detection label. In the case that the detection label is a fluorescent label, fluorescent detection would be favored. In one embodiment, the compound of the invention binds to the leptin receptor-positive cell and the binding is evaluated by measuring the change in fluorescence of the compound of the invention upon binding to the cell.

In the case where the peptide of amino acid sequence SEQ ID NO:2 is conjugated to a tagging element, the link between the peptide of amino acid sequence SEQ ID NO:2 and the tagging element is formed via a single bond or an optional linking group (the link is represented by -M-). Since the purpose of the linking group is merely to covalently join the tagging element and the peptide of amino acid sequence SEQ ID NO:2, the person skilled in the art will be able to use a large number of ways in which to achieve such linkage. In essence, the linking group may be any moiety that is at least bifunctional, provided that the resulting link between the tagging element and the peptide of amino acid sequence SEQ ID NO:2 is stable. Suitable linking moieties include bi- and multi-functional alkyl, aryl, aralkyl or peptidic moieties, alkyl, aryl or aralkyl aldehydes acids esters and anhydrides, sulfhydryl or carboxyl groups, such as maleimido benzoic acid derivatives, maleimido propionic acid derivatives and succinimido derivatives, or may be derived from cyanuric bromide or chloride, carbonyldiimidazole, succinimidyl esters or sulphonic halides and the like (U.S. Pat. No. 6,472,507, the entire disclosure of which is incorporated herein by reference). The functional groups on the linker moiety may include amino, hydrazino, hydroxyl, thiol, maleimido, carbonyl, and carboxyl groups. Optionally the linker group is selected so as to be sufficiently labile (e.g., to undergo enzymatic cleavage by an enzyme present in the targeted tissue) so that it is cleaved following achievement of the intended function of the working element (such as, in the case where the tagging element is a transduction domain, transport of the peptide of the amino acid sequence SEQ ID NO:2) thereby releasing the peptide. Exemplary labile linkages are described in U.S. Pat. No. 5,108,921, the entire disclosure of which is incorporated herein by reference. The peptide-active agent delivery system may also dissociate by way of chemical cleavage between the active agent and peptide of the invention. Within the embodiments wherein the linker moiety includes amino acid residues, such cleavage may occur within the linker moiety itself.

The examples provided below are intended to be illustrative and not comprehensive. Thus, the examples below illustrate the case where the bonds between the -M- group and the peptides are amide bonds, but the person skilled in the art would appreciate that the link may be formed by means of any functional groups capable of forming bonds between the terminal —NH— group of the peptide of amino acid sequence SEQ ID NO:2 and a —C(=O)— group of the terminal (or other) carboxyl group (or the terminal, or other —NH— group, or any other functional group of the transduction domain).

If the link formed by the linking group is between the N-terminus of the peptide of amino acid sequence SEQ ID NO:2 and a carboxyl group of the tagging element (for example the terminal carboxyl group of a peptidic tagging element of the terminal carboxyl group of a molecule), any amino acid (including, but not restricted to, α-amino acids including, but not restricted to, the proteinogenic amino acids) or peptide chain may form the link between the peptide of amino acid sequence SEQ ID NO:2 and the working element.

Examples of suitable linking groups -M- for linking the N-terminus of the amino acid sequence SEQ ID NO:2 and a carboxyl group of the working element include:
—NH—CH(R)—C(=O)—, wherein R is a side chain of a proteinogenic amino acid;
a peptide chain; and
—NH—X$_m$C(=O)—, wherein:
m is one or greater, preferably one to three,
each —X— is selected from the group consisting of:
a linear, branched, or cyclic aliphatic hydrocarbon, wherein one or more methylene groups are optionally replaced by —O— or —S— and one or more methine groups are optionally replaced by N;
—CH$_2$CH$_2$(OCH$_2$CH$_2$)$_n$—; wherein "n" is one or greater; and,
an aromatic or heteroaromatic ring.

If the link formed by the linking group is between the amino acid terminus of the peptide of amino acid sequence SEQ ID NO:2 and an amino group of the working element (for example the terminal amino group of a peptidic working element or the terminal amino group of a molecule), the link between the two peptide groups could be for example be a urea (where -M- is —C(=O)—) or any dicarboxylic acid residue (e.g. -M- is —C(=O)—(C$_1$-C$_6$)alkylene-C(=O)—).

Examples of suitable linking group -M- for linking the N-terminus of the amino acid sequence SEQ ID NO:2 and an amino group of the working element include:
—C(=O)— (i.e. a urea);
—C(=O)—Pep$^1$-NH—C(=O)—NH-Pep$^2$-C(=O)—, wherein —NH-Pep$^1$-C(=O)— and —NH-Pep$^2$-C(=O)— each represent either an amino acid or a peptide chain, linked via their amino termini (or the α-amino group in the case of an amino acid) by the urea linkage —NH—C(=O)—NH—; and
—C(=O)—X$_n$—C(=O)—, wherein:
m is one or greater, preferably one to three;
each —X— is selected from the group consisting of:
a linear, branched, or cyclic aliphatic hydrocarbon, wherein one or more methylene groups are optionally replaced by —O— or —S— and one or more methine groups are optionally replaced by N;
—CH$_2$CH$_2$(OCH$_2$CH$_2$)$_n$—; wherein "n" is one or greater; and,
an aromatic or heteroaromatic ring.

Although the -M- group is referred to as "linking" the working element and the peptide of amino acid sequence SEQ ID NO:2, the use of this term is not intended to imply any limitation as to the process by which the compound of formula (I) is synthesized. Thus it is not necessary that the working element and a peptide of amino acid sequence SEQ ID NO:2 be separately synthesized and then linked together. Rather, the term merely describes the structural connection between the working element, the peptide of amino acid sequence SEQ ID NO:2, and the linking group -M- in the compound of formula (I).

The tagging element is selected from the group consisting of a transduction domain and a detection label.

Non-limiting examples of transduction domains are peptides derived from the HIV Tat-derived peptide. The HIV Tat-derived peptide is a small basic peptide that has been successfully shown to deliver a large variety of cargoes, from small particles to proteins, peptides and nucleic acids, to the interior of a cell. The transduction domain appears to be confined to a small (9 amino acids) stretch of basic amino acids, with the sequence Arg-Lys-Lys-Arg-Arg-Gln-Arg-Arg-Arg [SEQ ID NO:11] (Ruben et al., 1989, J. Virol. 63: 1-8; Fawell et al., 1994, Proc. Natl. Acad. Sci. U.S.A. 91: 664-668; Vives et al., 1997, J. Biol. Chem. 272: 16010-16017; Futaki et al., 2001, J. Biol. Chem. 276: 5836-5840). The preferred Tat-derived peptides to be used within the present invention are: Tyr-Gly-Arg-Lys-Lys-Arg-Arg-Gln-Arg-Arg-Arg [SEQ ID NO:10], Arg-Lys-Lys-Arg-Arg-Gln-Arg-Arg-Arg [SEQ ID NO:11], Gly-Arg-Lys-Lys-Arg-Arg-Gln-Arg-Arg-Arg-Gly-Tyr-Lys-Cys [SEQ ID NO:12], Tyr-Gly-Arg-Lys-Lys-Arg-Arg-Gln-Arg-Arg-Arg-Gly [SEQ ID NO:13], Gly-Arg-Lys-Lys-Arg-Arg-Gln-Arg-Arg-Arg-Pro-Pro-Gln-Cys [SEQ ID NO:14], Gly-Arg-Lys-Lys-Arg-Arg-Gln-Arg-Arg-Arg-Pro-Pro-Gln [SEQ ID NO:15], Tyr-Ala-Arg-Lys-Ala-Arg-Arg-Gln-Ala-Arg-Arg [SEQ ID NO:16], Tyr-Ala-Arg-Ala-Ala-Ala-Arg-Gln-Ala-Arg-Ala [SEQ ID NO:17], Tyr-Ala-Arg-Ala-Ala-Arg-Arg-Ala-Ala-Arg-Arg [SEQ ID NO:18] and Tyr-Ala-Arg-Ala-Ala-Arg-Arg-Ala-Ala-Arg-Ala [SEQ ID NO:19].

Other non-limiting examples of transduction domains are peptides derived from Drosophila Antennapedia transcription factor (ANTP), as described in Mann and Frankel, 1991, EMBO J. 10: 1733-1739; and Vives et al., 1997, J. Biol. Chem. 272: 16010-16017. The preferred ANTP derived peptides to be used within this invention are Arg-Gln-Ile-Lys-Ile-Trp-Phe-Gln-Asn-Arg-Arg-Met-Lys-Trp-Lys-Lys [SEQ ID NO:20], Arg-Gln-Ile-Lys-Ile-Trp-Phe-Pro-Asn-Arg-Arg-Met-Lys-Trp-Lys-Lys [SEQ ID NO:21], Lys-Lys-Trp-Lys-Met-Arg-Arg-Asn-Gln-Phe-Trp-Val-Lys-Val-Gln-Arg [SEQ ID NO:22], Arg-Arg-Trp-Arg-Arg-Trp-Trp-Arg-Arg-Trp-Trp-Arg-Arg-Trp-Arg-Arg [SEQ ID NO:23], Arg-Arg-Met-Lys-Trp-Lys-Lys [SEQ ID NO:24], Apa-Arg-Gln-Ile-Lys-Ile-Trp-Phe-Gln-Asn-Arg-Arg-Met-Lys-Trp-Lys-Lys [SEQ ID NO:25], and Apa-Arg-Gln-Ile-Lys-Ile-Trp-Phe-Pro-Asn-Arg-Arg-Met-Lys-Trp-Lys-Lys [SEQ ID NO:26], wherein Apa is aminopentanoic acid.

Other non-limiting examples of transduction domains are the following peptides: Arg-Arg-Arg-Arg-Arg-Arg-Arg [SEQ ID NO:27, arginine 7-mer], Arg-Arg-Arg-Arg-Arg-Arg-Arg-Arg-Arg [SEQ ID NO:28, arginine 9-mer], Asp-Ala-Ala-Thr-Arg-Ser-Ala-Ala-Ser-Arg-Pro-Thr-Glu-Arg-Pro-Arg-Ala-Pro-Ala-Arg-Ser-Ala-Ser-Arg-Pro-Arg-Arg-Pro-Val-Glu [SEQ ID NO:29, VP22 transduction domain (Herpes Simplex Virus 1)], Gly-Ala-Leu-Phe-Leu-Gly-Trp- Leu-Gly-Ala-Ala-Gly-Ser-Thr-Met-Gly [SEQ ID NO:30, GP41 fusion sequence], Gly-Ala-Leu-Phe-Leu-Gly-Phe-Leu-Gly-Ala-Ala-Gly-Ser-Thr-Met-Gly-Ala-Trp-Ser-Gln-Pro-Lys-Ser-Lys-Arg-Lys-Val [SEQ ID NO:31, GP41 fusion sequence], Met-Gly-Leu-Gly-Leu-His-Leu-Leu-Val-Leu-Ala-Ala-Ala-Leu-Gln-Gly-Ala-Trp-Ser-Gln-Pro-Lys-Lys-Lys-Arg-Lys-Val [SEQ ID NO:32, Caiman crocodylus Ig(v) light chain-SN40NLS], Pro-Leu-Ser-Ser-Ile-Phe-Ser-Arg-Ile-Gly-Asp-Pro [SEQ ID NO:33, hepatitis B virus PreS2 antigen consisting of the translocation motif from residues 41-52], Phe-Trp-Arg-Gly-Asp-Leu-Val-Phe-Asp-Phe-Gln-Val [SEQ ID NO:34, hepatitis A virus VP3 core protein], Lys-Phe-Thr-Ile-Val-Phe-Pro-His-Asn-Gln-Lys-Gly-Asn-Trp-Lys-Asn-Val-Pro-Ser-Asn-Tyr-His-Tyr-Cys-Pro [SEQ ID NO:35, vesicular stomatitis virus VSV-G peptide], Ala-Lys-Arg-Ala-Arg-Leu-Ser-Thr-Ser-Phe-Asn-Pro-Val-Tyr-Pro-Tyr-Glu-Asp-Glu-Ser [SEQ ID NO:36, adenovirus fiber], Gly-Trp-Thr-Leu-Asn-Ser-Ala-Gly-Tyr-Leu-Leu-Gly-Lys-Ile-Asn-Leu-Lys-Ala-Leu-Ala-Ala-Leu-Ala-Lys-Lys-Ile-Leu [SEQ ID NO:37, transportan], Arg-Gly-Gly-Arg-Leu-Ser-Tyr-Ser-Arg-Arg-Arg-Phe-Ser-Thr-Ser-Thr-Gly-Arg [SEQ ID NO:38, SynB1], Ala-Ala-Val-Ala-Leu-Leu-Pro-Ala-Val-Leu-Leu-Ala-Leu-Leu-Ala-Pro [SEQ ID NO:39, Kaposi's sarcoma-associated herpesvirus, Kaposi FGF signal sequence], Ala-Ala-Val-Leu-Leu-Pro-Val-Leu-Leu-Ala-Ala-Pro [SEQ ID NO:40, Kaposi's sarcoma-associated herpesvirus, Kaposi FGF signal sequence], Val-Thr-Val-Leu-Ala-Leu-Gly-Ala-Leu-Ala-Gly-Val-Gly-Val-Gly [SEQ ID NO:41, human integrin beta3 signal sequence], Val-Ala-Tyr-Ile-Ser-Arg-Gly-Gly-Val-Ser-Thr-Tyr-Tyr-Ser-Asp-Thr-Val-Lys-Gly-Arg-Phe-Thr-Arg-Gln-Lys-Tyr-Asn-Lys-Arg-Ala [SEQ ID NO:42, P3 membrane fusion sequence], Lys-Leu-Ala-Leu-Lys-Leu-Ala-Leu-Lys-Ala-Leu-Lys-Ala-Ala-Leu-Lys-Leu-Ala [SEQ ID NO:43, model ambiphilic peptide], Trp-Glu-Ala-Lys-Leu-Ala-Lys-Ala-Leu-Ala-Lys-Ala-Leu-Ala-Lys-His-Leu-Ala-Lys-Ala-Leu-Ala-Lys-Ala-Leu-Lys-Ala-Cys-Glu-Ala [SEQ ID NO:44, KALA], Arg-Arg-Gln-Arg-Arg-Thr-Ser-Lys-Leu-Met-Lys-Arg [SEQ ID NO:45, disclosed in U.S. Pat. No. 6,881,825, incorporated by reference herein in its entirety] and Val-Asp-Lys-Gly-Ser-Tyr-Leu-Pro-Arg-Pro-Thr(NAcGal)-Pro-Pro-Arg-Pro-Ile-Tyr-Asn-Arg-Asn [SEQ ID NO. 46, disclosed in U.S. Pat. No. 7,015,309, incorporated by reference herein in its entirety].

Non-limiting examples of detection labels are fluorescent labels, such as cyanin derivatives (Bioconj. Chem. 1993, 4, 105-111), coumarin derivatives such as aminomethylcoumarin (Histochem. J. 1986, 8(9): 497-9), Lucifer Yellow (Invitrogen, Carlsbad, Calif.), dansyl chloride and derivatives (Methods Mol. Biol. 1994, 32: 329-34), phycobiliproteins (such as B-phycoerythrin, R-phycoerythrin and allophycocyanin; Biochem, J. 1980, 187 (2): 303-9), Oregon Green 488 (J. Lipid Res. 2003, 44 (5): 1033-1041), rhodamine derivatives (such as Rhodamine B, Rhodamine 6G, Rhodamine 123, tetramethylrhodamine, Sulforhodamine 101, and Rhodamine Red; Invitrogen, Carlsbad, Calif.), Texas Red (sulfonyl chloride version of sulforhodamine 101; Immunol. Methods 1982, 50 (2): 193-204), fluorescein (Pract. Synth. Proced. 2004, 31 (15): 2591-2593), BODIPY derivatives (FL, TR, and TMR; Chem. Rev. 2007, 107 (11): 4891-4932), carboxy SNARF-1 (Invitrogen, Carlsbad, Calif.), Cascade Blue (Invitrogen, Carlsbad, Calif.), and the family of Alexa Fluor dyes (such as Alexa Fluor 350, Alexa Fluor 488, Alexa Fluor 647, Alexa Fluor 546, Alexa Fluor 594, Alexa Fluor 660, and Alexa Fluor 680; Molecular Probes, Invitrogen, Carlsbad, Calif.).

Salts of the Compounds of the Invention.

The compounds of the invention may form salts with acids or bases, and such salts are included in the present invention. The preferred salts are pharmaceutically-acceptable salts. The term "salts" embraces addition salts of free acids or free bases that are compounds of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. All of these salts may be prepared from the corresponding compound by reacting, for example, the appropriate acid or base with the compound.

Medical and Therapeutic Use and Pharmaceutical Compositions

The compounds of the invention find utility in the promotion of growth arrest or death of leptin receptor-positive cancer cells in vitro. The compounds of the invention also find utility in the promotion of growth arrest or death of leptin-receptor-positive cancer cells in vivo. The compounds of the invention also find utility in the treatment of a weight-loss nutritional disorder, such as cachexia and wasting, in vivo. The compounds of the invention also find utility in the treatment of osteoporosis in vivo. The compounds of the invention also find utility in the treatment of rheumatoid arthritis. The compounds of the invention also find utility in the treatment of osteoarthritis in vivo. The compounds of the invention also find utility in the treatment of inflammatory bowel disease.

The ability of the compounds of the invention to inhibit growth or kill a specific type of cancer cell or a specific group of types of cancer cells is conferred by the presence of a leptin receptor on the surface of the cancer cell or group of cancer cells in question. Identification of a cancer cell as ObR-positive or ObR-negative should indicate whether or not the compounds of the invention may be able to promote growth arrest or death of the cell.

When used to promote the growth arrest or killing of cancer cells in vitro, one skilled in the art should be able to vary the contact time and the concentration of the compound of the invention to optimize the degree of growth arrest or killing of cancer cells. Other experimental parameters may be varied to achieve these effects, depending on the specific experiment conducted, and identification of such parameters should involve minimal experimentation by those skilled in the art.

When used in vivo, the compound of the invention is preferably administered as a pharmaceutical composition, comprising a mixture of a compound of the invention and a pharmaceutically acceptable carrier. The compound of the invention may be present in a pharmaceutical composition in an amount from 0.001 to 99.9 wt %, more preferably from about 0.01 to 99 wt %, and even more preferably from 0.1 to 95 wt %.

It should be appreciated that all the preceding and following therapeutic applications may also be performed in an "ex vivo" manner. In this case, a tissue or organ in which promotion of growth arrest or killing of cancer cells is desired may be removed from an organism, under conditions which allows the tissue or organ to remain viable and with minimal alteration of the natural conditions of the tissue or organism. The procedure should usually be conducted under sterile conditions to minimize possibility of contamination. The tissue or organ may be exposed to the composition of the invention for a variable amount of time, from minutes to days. The composition of the invention may be provided as suspensions, powders, pastes or other suitable presentations, and the mode of contact between the composition of the invention and the tissue or organ should be such that growth arrest or killing of cancer cells is achieved. Those skilled in the art should be able to determine the optimal contact time without undue experimentation. Once the desired detection or killing of cancer cells is achieved, the tissue or organ may be returned to the original organism or to another organism in need to such tissue or organ. Transplantations should proceed following the procedures known by those skilled in the art.

As to the use of a compounds of the invention for treatment of cancers, one skilled in the art may readily determine an effective amount of the compound of the invention to be administered to a given subject, by taking into account factors such as the size and weight of the subject; the size and shape of the cancerous growth; the location and accessibility of the cancerous growth; the age, health and sex of the subject; the route of administration; and whether the administration is local or systemic. As to the use of a compound of the invention for treatment of a weight-loss nutritional disorder, one skilled in the art can readily determine an effective amount of the compound of the invention to be administered to a given subject, by taking into account factors such as the size and weight of the subject; the degree of severity of the weight-loss nutritional disorder; the age, health and sex of the subject; the route of administration; and whether the administration is local or systemic. As to the use of a compound of the invention for treatment of osteoporosis, one skilled in the art can readily determine an effective amount of the compound of the invention to be administered to a given subject, by taking into account factors such as the size and weight of the subject; the degree of severity of bone loss; the age, health and sex of the subject; the route of administration; and whether the administration is local or systemic. Those skilled in the art may derive appropriate dosages and schedules of administration to suit the specific circumstances and needs of the subject. For example, suitable doses of the compound of the invention may be estimated from the volume of cancer cells to be killed or the degree of severity of the weight-loss nutritional disorder. Typically, dosages of the compound of the invention, in terms of mass of the peptide of the invention, are between about 0.001 mg/kg and about 100 mg/kg body weight. In some embodiments, dosages are between about 0.01 mg/kg and about 60 mg/kg body weight.

It is understood that the effective dosage will depend on the age, sex, health, and weight of the recipient, kind of concurrent treatment, if any, frequency of treatment, and the nature of the effect desired. The most preferred dosage will be tailored to the individual subject, as is understood and determinable by one of skill in the art, without undue experimentation.

A mixture of compounds of the invention can be administered in equimolar concentrations to a subject in need of such treatment. The mixture may comprise, for example, different compounds corresponding to Formula (I). In an instance, the compounds of the invention are administered in concentrations that are equimolar. In another instance, the compounds of the invention are administered in concentrations that are not equimolar. In yet another instance, the compounds of the invention are administered as equal amounts of compound, by weight, per kilogram of body weight. In another instance, the compounds of the invention are administered in unequal amounts. In yet other instances, the amount of each compound of the invention to be administered is based on its ability to promote growth arrest or killing of cancer cells or its ability to treat weight-loss nutritional disorders.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

A pharmaceutical composition used in the practice of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The pharmaceutical compositions may be administered in a variety of unit dosage forms depending upon the method of administration.

The relative amounts of the active ingredient, the pharmaceutically acceptable carrier, and any additional ingredients in a pharmaceutical composition used in the practice of the invention will vary, depending upon the identity, size, and condition of the subject treated and further depending upon the route by which the composition is to be administered. By way of example, the composition may comprise between 0.01% and 99.9% (w/w) active ingredient.

The compounds of the present invention are useful for prophylactic and/or therapeutic treatment. In therapeutic applications, preferred pharmaceutical compositions are administered in a dosage sufficient to kill or stop growth of leptin-receptor-positive cancer cells; or minimize, stop or revert cachexia or wasting; or minimize, stop or revert osteoporosis, rheumatoid arthritis, osteoarthritis or inflammatory bowel disease. An amount adequate to accomplish this is defined as a "therapeutically effective dose." Amounts effective for this use will depend upon the severity of the disease and the general state of the subject's health.

Administration of the Compounds of the Invention

In general, the schedule or timing of administration of a composition of the invention is according to the accepted practice for the procedure being performed.

All of the various compounds of the invention to be administered need not be administered together in a single formulation. The different compounds can be administered in separate formulations. For example, if three different compounds are to be administered, the three different compounds can be delivered in three separate formulations. In addition, each compound can be delivered at the same time, or the compounds can be delivered consecutively with respect to one another. Thus, the mixture of the compounds can be administered in a single formulation, or in multiple formulations comprising one or more compounds.

In view of the disclosure contained herein, those skilled in the art will appreciate that the present compounds of the invention may have a beneficial effect in treatment of osteoporosis, rheumatoid arthritis, osteoarthritis, inflammatory bowel disease, a weight-loss nutritional disorder or many kinds of cancer, such as, but not limited to, glioma, breast cancer, colorectal cancer, prostate cancer, pancreatic cancer, ovarian cancer, endometric cancer and lung cancer. It is therefore contemplated that the compositions of this invention may take numerous and varied forms, depending upon the particular circumstance of each application. For example, the composition used in the practice of the invention may be incorporated into a solid pill or may in the form of a liquid dispersion or suspension. In general, therefore, the formulation of the present invention preferably comprises the compound of Formula (I) and a suitable, non-toxic, physiologically acceptable carrier. As the term is used herein, "carrier" refers broadly to materials that facilitate administration or use of the present compounds for treating osteoporosis, a weight-loss nutritional disorder in vivo or promoting growth arrest or killing of cancer cell in vitro or in vivo. A variety of non-toxic physiologically acceptable carriers may be used in forming these formulations, and it is generally preferred that these formulations be of physiologic salinity.

For some applications involving osteoporosis treatment, rheumatoid arthritis treatment, osteoarthritis treatment, inflammatory bowel disease treatment, weight-loss nutritional disorder treatment or cancer treatment, it may be desirable to have available a physically applicable or implantable predetermined solid form of material containing the composition of the invention. Accordingly, it is contemplated that the compositions of this invention may be incorporated in solid forms, such as capsules. They may thus be introduced at or near the sites of cancer growth, for example. In such embodiments, the compositions of the present invention are preferably combined with a solid carrier that itself is bioacceptable and suitably shaped for its use. For many applications, it is preferred that the compositions of the present invention be prepared in the form of an aqueous dispersion, suspension or paste that can be directly applied to the site of cancer growth.

The compound and pharmaceutical composition comprising the compound may be administered by any method designed to allow compounds to have a physiological effect. Pharmaceutical compositions that are useful in the methods used in the practice of the invention may be prepared, packaged, or sold in formulations suitable for intravenous, oral, rectal, subcutaneous, intranasal, intracisternal, intravaginal, intraperitoneal or local, or another route of administration. Other contemplated formulations include projected nanoparticles, liposomal preparations, resealed erythrocytes containing the active ingredient, and immunologically-based formulations.

Single or multiple administrations of the compositions may be administered depending on the dosage and frequency as required and tolerated by the subject. In any event, the administration regime should provide a sufficient quantity of the composition of this invention to effectively treat the subject.

Administration may occur enterally or parenterally; for example intravenously, orally, rectally, intracistemally, intravaginally, intraperitoneally, intranasally, subcutaneously or locally.

One preferred mode of administration is parenteral administration. As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like.

Particularly preferred parenteral administration methods include intravascular administration (e.g., intravenous bolus injection, intravenous infusion, intra-arterial bolus injection, intra-arterial infusion and catheter instillation into the vasculature), peri- and intra-target tissue injection, subcutaneous injection or deposition including subcutaneous infusion (such as by osmotic pumps), intramuscular injection, intrasternal injection, kidney dialytic infusion techniques, intraperitoneal injection, and direct application to the target area, for example by a catheter or other placement device.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (e.g. powder or granular) form for reconstitution with a suitable vehicle (e.g. sterile pyrogen free water) prior to parenteral administration of the reconstituted composition.

A typical pharmaceutical composition for intravenous administration would be about 0.1 to 100 mg per subject per day. Dosages from 0.1 up to about 300 mg per subject per day may be used, particularly when the drug is administered to a secluded site and not into the blood stream, such as into a body cavity or into a lumen of an organ. Methods for preparing parenterally administrable compositions will be known or apparent to those skilled in the art and are described in more detail in such publications as Remington's Pharmaceutical Science, 15th ed., 1980, Mack Publishing Company, Easton, Pa.

Another preferred mode of administration is oral administration. A formulation of a pharmaceutical composition used in the practice of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion. As used herein, an "oily" liquid comprises a carbon-containing liquid molecule that exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture.

Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Powdered and granular formulations of a pharmaceutical preparation used in the practice of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition used in the practice of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (e.g. such as with a physiologically degradable material), and methods of absorbing an aqueous or oily solution or suspension into an absorbent material, with or without subsequent drying.

Controlled- or sustained-release formulations of a pharmaceutical composition used in the practice of the invention may be made using conventional technology. The pharmaceutical compositions of the present invention developed for slow or controlled release of the active ingredient may include hydroxypropylmethyl cellulose in varying proportions to provide the desired release profile, other polymer matrices, gels, permeable membranes, osmotic systems, multilayer coatings, microparticles, liposomes and/or microspheres.

In general, a controlled-release preparation is a pharmaceutical composition capable of releasing the active ingredient at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations. In an embodiment of the invention, a controlled release composition of the invention provides continuous release of an active agent over a fourteen day period of time. For references on controlled-release methods, see U.S. Pat. Nos. 5,674,533; 5,059,595; 5,591,767; 5,120,548; 5,073,543; 5,639,476; 5,354,566; and 5,733,566.

The controlled-release of the active ingredient may be stimulated by various inducers, for example pH, temperature, enzymes, water, or other physiological conditions or compounds. Various mechanisms of drug release exist. For example, in one embodiment, the controlled-release component may swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the active ingredient in the pharmaceutical composition. In another embodiment, the controlled-release component is biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

Another preferred mode of administration is pulmonary administration. A pharmaceutical composition of the invention may be prepared, packaged or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self propelling solvent/powder dispensing container, such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent, such as sugar, and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

Another preferred mode of administration is intranasal delivery. The formulations described herein as being useful for pulmonary delivery are also useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

The pharmaceutical compositions of the invention may be dispensed to the subject under medical intervention with the help of an applicator. The applicator to be used may depend on the specific medical condition being treated, amount and physical status of the pharmaceutical composition, and choice of those skilled in the art.

The pharmaceutical composition of the invention may be provided to the subject or the medical professional in charge of dispensing the composition to the subject, along with instructional material. The instructional material includes a publication, a recording, a diagram, or any other medium of expression, which can be used to communicate the usefulness of the composition and/or compound used in the practice of the invention in a kit. The instructional material of the kit may, for example, be affixed to a container that contains the compound and/or composition used in the practice of the invention or may be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

EXAMPLES

The invention is described hereafter with reference to the following examples. The examples are provided for the purpose of illustration only and the invention should in no way be construed as being limited to these examples, but rather should be construed to encompass any and all variations that become evident as a result of the teaching provided herein.

Methods

Peptide Synthesis.

All peptide synthesis materials were obtained from commercial sources, and the peptides were synthesized by solid-phase methods. The peptide chain assembly was made on a CEM Liberty microwave-assisted automated synthesizer (CEM Gmbh, Kamp-Lintfort, Germany). Standard Fmoc-chemistry was used throughout with a 4-molar excess of the acylating amino acids. Non-natural amino acids were coupled manually to ensure completion. Peptides were cleaved from the solid support with trifluoroacetic acid (TFA) in the presence of thioanisole (5%) and water (5%) as scavengers. After cleavage, the peptides were purified by reversed-phase high performance liquid chromatography (RP-HPLC). The final products were characterized by RP-HPLC and matrix-assisted laser desorption/ionization mass spectrometry (MALDI-MS).

Cell Proliferation and Viability Assay.

The XTT assay was used for the non-radioactive quantification of cell proliferation and viability. This colorimetric assay uses XTT (2,3-bis[2-methoxy-4-nitro-5-sulfophenyl]-2H-tetrazolium-5-carboxyanilide), a tetrazolium salt cleaved to a formazan by the succinate dehydrogenase system, which belongs to the mitochondrial respiratory chain and is only active in viable cells (Gerlier & Thomasset, 1986, J. Immunol. Methods 94:57-63). The formazan dye may thus only be formed by metabolically active and viable cells. The formazan dye formed is soluble in aqueous solutions and is directly quantified using a scanning multiwell spectrophotometer (ELISA reader) measured at 480 nm (optimum) or at 450 nm.

ObR Binding Activity of Designer Peptides.

For dot-blot assays, the leptin fragments were dissolved in electroblot transfer buffer (25 mM Tris and 192 M glycine buffer containing 20% methanol) and were applied to a nitrocellulose membrane (Otvos and Szendrei, 1996, "Enzyme-linked immunosorbent assay of peptides", pp. 269-275, in: "Neuropeptide Protocols", G. B. Irvine and C. H. Williams, eds., Humana Press, Totowa, N.J.). The solid surfaces were blocked with 5% BSA in a PBS-0.5% Tween 20 buffer (PBST) for 3 hours at room temperature and were subsequently incubated with 10 m/mL solution of human IgG Fc-conjugated ObR extracellular domain (R&D Systems, Minneapolis, Minn.) dissolved in Tris-buffered saline-0.1% Tween 20 buffer (TBST) containing 1% bovine serum albumin (BSA) for 1 hour. A monoclonal goat antibody (Santa Cruz Biotechnology, Santa Cruz, Calif.), specific for the N-terminus of human ObR, was added to the assay mixture, followed by addition of a horseradish peroxidase(HRP)-conjugated anti-goat IgG donkey antibody for the dot-blot assay. Between reagents, the solid surfaces were washed extensively with PBST. After washing with PBST, the membrane was treated with a chemiluminescence luminol oxidizer (NEN, Waltham, Mass.) for 1 min. The resultant chemiluminescence was exposed to a X-Omat blue XB-1 film (Kodak, Rochester, N.Y.) for 10 seconds, and the exposed film was developed.

Antagonistic Ligand Assay.

Human leptin was purchased from R&D Systems (Minneapolis, Minn.) and used at the concentration of 100 ng/mL (approximately 6 nM). MCF-7, LN18 and LN229 cells, naturally expressing ObR, were grown in a standard medium DMEM:F12 [1:1 mixture of Dulbecco's Modified Eagle Medium (DMEM) and Ham's F12 nutrient mixture, GIBCO™, Invitrogen, Carlsbad, Calif.] plus 5% fetal bovine serum. ObR-negative MCF-10 human mammary epithelial cells were grown in mammalian epithelial growth serum-free medium (SFM) supplemented with 100 ng/mL cholera toxin.

Seventy percent confluent cultures were synchronized in SFM (DMEM, 10 µM $FeSO_4$, 0.5% bovine serum albumin) for 24 h and then treated with leptin and/or peptides (different doses) for 5 days. Cell numbers before and after treatment were determined by counting the cells with trypan blue exclusion. All assays were done in triplicate and repeated 3-6 times. The changes in cell number versus control SFM were determined as percentage decrease/increase and expressed as means±standard error (SE). The results were statistically evaluated by Student's t-test and analysis of variance (ANOVA). Values of $p<0.05$ were considered statistically significant.

Example 1

Identification of an Initial Leptin-Based Antagonist

With the objective of identifying a peptide that is antagonistic against the leptin receptor, novel peptides based on the binding site III of leptin were designed. The starting point for the design was the truncated site III peptide Ser-Thr-Glu-Val-Val-Ala-Leu-Ser-Arg-Leu-$NH_2$ [SEQ ID NO:58]. A particularly interesting peptide, Thr-Glu-Nva-Nva-Ala-Leu-Ser-Arg-Nva$NH_2$ [SEQ ID NO:47] was identified in this effort.

The peptide of amino acid sequence SEQ ID NO:47 bound to the extracellular domain of ObR in a medium-throughput solid-phase assay. In this assay, the leptin fragments were dissolved in electroblot transfer buffer (25 mM Tris and 192 mM glycine buffer containing 20% methanol) and 1-50 µg of the peptides were dried down to ELISA plates at 37° C. The wells were blocked with 5% bovine serum albumin (BSA) in a phosphate-buffered saline/0.5% Tween 20 buffer (PBST) overnight at room temperature. The plates were washed 3 times with PBST, and then incubated with 50 µL of 1-100 nM solutions of human IgG Fc-conjugated ObR extracellular domain (R&D Systems, Minneapolis, Minn.) dissolved in Tris-buffered saline/0.1% Tween 20 buffer (TBST) containing 1% BSA for 2 h at 37° C. The plates were washed 3 times with PBST. Fifty microliters of a goat monoclonal antibody (Ab), recognizing the N-terminus of human ObR (Santa Cruz Biotechnology, Santa Cruz, Calif.) was added as a primary antibody at 1:100 dilution overnight at 4° C. and the plates were washed 3 times with PBST. Then the wells were incubated with 50 µL of horseradish peroxidase (HRP)-conjugated anti-goat Fc mouse antibody in 1:100 dilution for 2 h at room temperature and washed 5 times with PBST. The ELISA was developed with 100 µL/well of an HRP ELISA kit featuring tetramethylbenzidine as substrate and sulfuric acid as stop solution. Absorbance values were determined at 405 and 595 nm (respectively before and after adding the stop solution) on a BioTek Instruments EL311 microplate reader. The binding assays were done in triplicate and the experiments repeated at least 4 times, except in cases when very high peptide concentrations were used.

The peptide interfered with leptin-induced proliferation of the ObR-expressing MCF-7 breast cancer cells in a concentration-dependent manner. The peptide of amino acid sequence SEQ ID NO:47 was found to be a full antagonist of ObR at 1 µM but had no agonistic activity. Determination of the half-life in mouse serum showed that this peptide has a short half-life of only 8 minutes. Acetylation of the N-terminus of the peptide of amino acid sequence SEQ ID NO:47 afforded the peptide of amino acid sequence SEQ ID NO:48 [AcNH-Thr-Glu-Nva-Nva-Ala-Leu-Ser-Arg-Nva$NH_2$], which had an increased half-life in mouse serum of 14 min but no change in the cell viability profile presented by the unprotected variant.

Example 2

Identification and Characterization of True Leptin-Based Antagonists

Based on the discovery of the peptide of amino acid sequence SEQ ID NO:47, an analog library was designed, using non-natural amino acids as replacements for the natural amino acid residues of the peptide of amino acid sequence SEQ ID NO:47. The binding of the library members to the extracellular domain of ObR was evaluated by dot-blot (FIG. 1).

In carrying out the binding assay, the peptides were loaded to the paper between 10 and 20 pg quantities. The sensitivity of the assay was considered to lie at 2 pg of leptin-based peptide, based on the assumption that the cellular $IC_{50}$ value was around 100-200 nM. The negative control used in the screen was the antibacterial peptide dimer A3-APO [(Chex-Arg-Pro-Asp-Lys-Pro-Arg-Pro-Tyr-Leu-Pro-Arg-Pro-Arg-Pro-Pro-Arg-Pro-Val-Arg)$_2$ Dbu; SEQ ID NO:7; Cassone et al., 2008, Peptides 29: 1878-1886] and the positive control was 2 pg of the peptide of amino acid sequence Tyr($I_2$)-Serβ(Glc)-Thr-Glu-Val-Val-Ala-Leu-Ser-Arg-Leu-Dpr(Ac) [SEQ ID NO:8].

Among the analogs analyzed, the peptide with the amino acid sequence Thr-Glu-Nva-Val-Ala-Leu-Ser-Arg-Acp$NH_2$ [SEQ ID NO:4] bound to the ObR receptor on solid phase in a clearly visible manner. The tight binding of this peptide to the receptor was reflected in the $IC_{50}$ value to ObR expressing cells.

Figure 2:
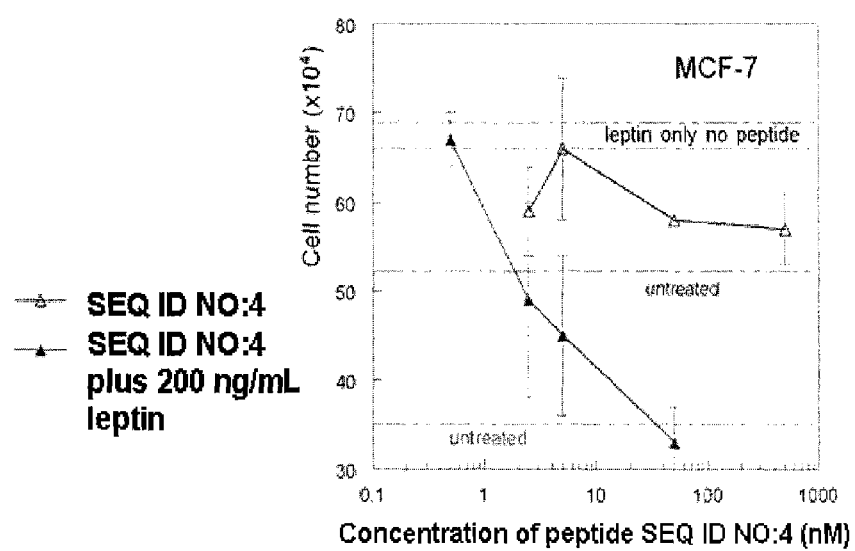
FIG. 2 shows the effect of the peptide of amino acid sequence SEQ ID NO:4 on the proliferation of MCF-7 breast cancer cells (ObR-positive). Similar results were obtained with LN229 glioma cells (not shown). Both cell lines express the leptin receptor and proliferate upon stimulation with leptin.

As assessed by both classic proliferation assays and XTT metabolic activity assays, the peptide of amino acid sequence SEQ ID NO:4 antagonized leptin action in two ObR-positive cell lines, LN229 (glioma) and MCF-7 (breast cancer), with an approximate $IC_{50}$ of 2-3 nM, with full inhibition at 50 nM (FIG. 2). The peptide did not influence the cell growth when added alone (broken line).

Figure 3:
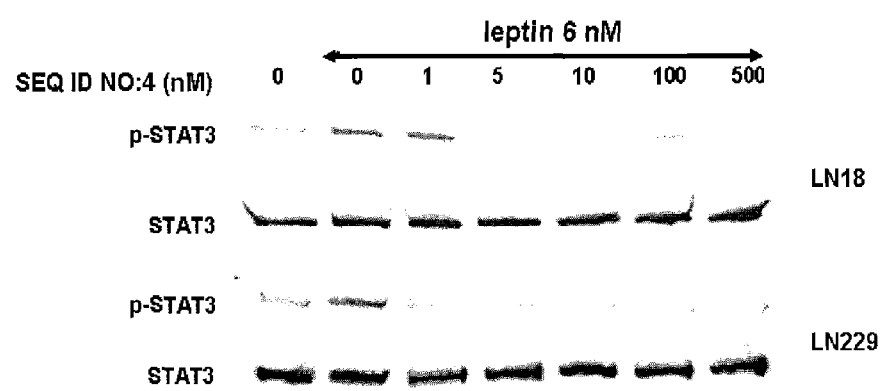
FIG. 3 shows the activation of STAT3 in the presence of leptin and varying concentrations of the peptide of amino acid sequence SEQ ID NO:4, as detected by Western blotting.

FIG. 3 illustrates the activation of STAT3 in the presence of leptin (6 nM; lanes 2-6) and varying concentrations of the peptide of amino acid sequence SEQ ID NO:4 in LN18 and LN228 glioblastoma cells. The phosphorylation of STAT3 on Tyr705 (p-STAT3, upper panels) and total STAT3 were detected by Western blotting. The peptide of amino acid sequence SEQ ID NO:4 completely inhibited leptin-induced STAT3 phosphorylation stating at 1-5 nM concentrations.

Figure 4:
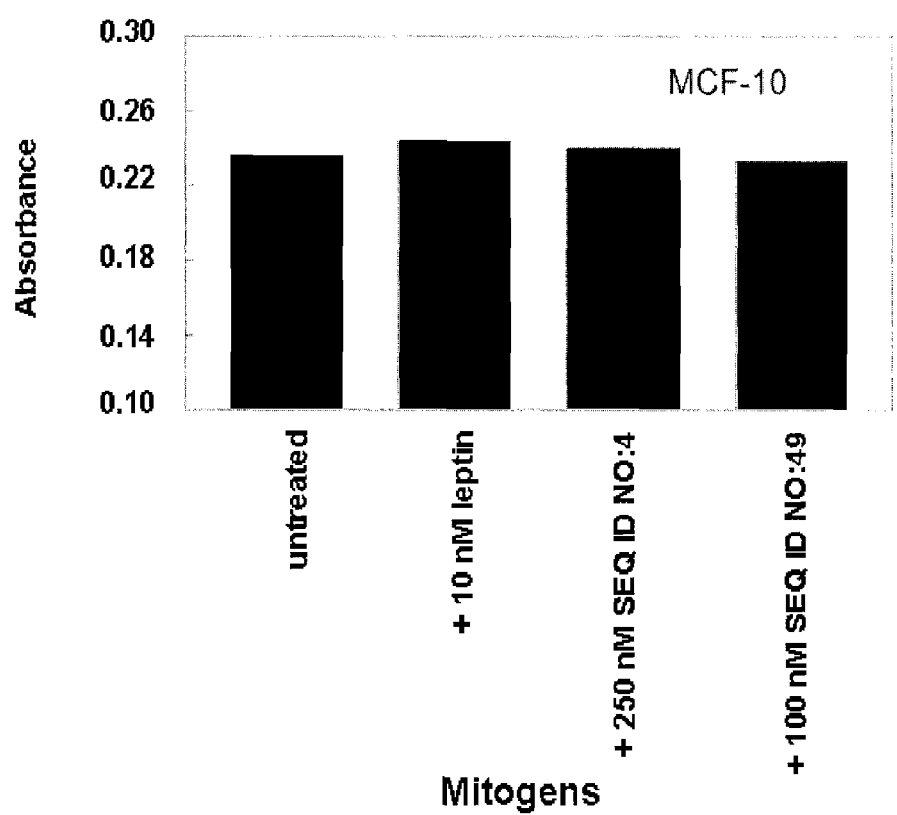
FIG. 4 shows the effect of the peptide of amino acid sequence SEQ ID NO:4 and its N-terminal acetylated derivative peptide of amino acid sequence SEQ ID NO:9 on ObR-negative MCF-10 cells, as measured by the XXT assay.

The growth of ObR-negative MCF-10 cells was not influenced by the peptide of amino acid sequence SEQ ID NO:4 up to the highest concentration studied at 250 nM, representing an in vitro therapeutic index of at least 100 (FIG. 4). This peptide did not significantly interfere with MCF-7 growth when the cells are not stimulated with exogenous leptin. The peptide of amino acid sequence SEQ ID NO:4 was thus shown to be a highly selective, non-toxic inhibitor of leptin-dependent cancer cell proliferation.

Another compound that showed activity as a leptin antagonist was the peptide of amino acid sequence (D)-Ser-Glu-Nva-Val-Ala-Leu-Ser-N-MeArg-bAlaNH$_2$ [SEQ ID NO:6]. This peptide demonstrate antagonistic activity against the leptin receptor ($IC_{100}$=10-100 pM) in two brain tumor cell lines in vitro. The peptide has no agonistic activity and does not influence cell growth without stimulation with leptin protein.

The effect of the peptides of the invention on the proliferation of ObR-positive cancer cells (brain and breast) in the presence ($IC_{50}$) or absence ($EC_{50}$) of exogenous leptin protein (6 nM) is summarized in Table 1. Selective nanomolar efficacious peptides were designated full antagonists, and peptides with picomolar activity were designated super antagonists.

TABLE 1

| Sequence Identifier | $IC_{50}$ | $IC_{100}$ | $EC_{50}$ | pharmacology |
|---|---|---|---|---|
| SEQ ID NO: 4 | 5 nM | 50 nM | >1 µM | full antagonist; no effect on ObR-negative cells |
| SEQ ID NO: 6 | 200 pM | <1 nM | >1 µM | super antagonist |
| SEQ ID NO: 47 | 1 µM | | >1 µM | weak antagonist |
| SEQ ID NO: 49 | 200 pM | 5 nM | >1 µM | super antagonist |
| SEQ ID NO: 51 | 50 nM | 100 nM | >500 nM | weak full antagonist |
| SEQ ID NO: 53 | >1 µM | | | inactive |

Example 3

Modifications of the Antagonist Peptide

N-terminal acetylation of the peptide of amino acid sequence SEQ ID NO:4 produced the peptide of amino acid sequence SEQ ID NO:9, which was shown to be a partial agonist. Nevertheless, the peptide of amino acid sequence SEQ ID NO:9 did not influence the growth profile of the ObR-negative MCF-10 cell line (FIG. 4), indicating that the change in the anti-tumor pharmacological profile was not accompanied by toxic alterations.

Example 4

Biological Activity of an Antagonist Peptide

The peptide of amino acid sequence SEQ ID NO:4 showed efficacy in a rat model of weight gain after intranasal administration.

Six weeks old Black/6 mice (mixed race) and F344 female rats were grown on regular lab chow and had access to food and water ad libidum. Treatment started at day 0, with four mice (2 males and 2 females) and 4 rats per group. The animals received the peptide of amino acid sequence SEQ ID NO:4 or physiological salt solution once daily. The mice and rats were dosed according to the following schedule:

Group 1: Mice, salt solution intraperitoneally;
Groups 2 and 3: Mice 0.1 mg/kg/day or 0.01 mg/kg/day peptide of amino acid sequence SEQ ID NO:4 intraperitoneally in 100 microliter salt solution;
Groups 4 and 5: Mice 1 mg/kg/day or 0.1 mg/kg/day peptide of amino acid sequence SEQ ID NO:4 subcutaneously (under the shoulder blade) in 100 microliter salt solution;
Groups 6 and 7: Mice 10 mg/kg/day or 1 mg/kg/day peptide of amino acid sequence SEQ ID NO:4 orally in 100 microliter salt solution;
Group 8: Rats, 10 microliter salt solution, intranasally;
Group 9: Rats. 0.1 mg/kg/day peptide of amino acid sequence SEQ ID NO:4 intranasally in 10 microliter salt solution.

The weights of the animals and the consumed food amounts were recorded daily. The weight gain was 2% total after 10 days of treatment at a dose of 0.1 mg/kg daily.

After 14 days the animals were sacrificed and their liver, brain, kidneys and spleen were submitted for toxicity testing. No obvious toxic effects were observed in any conditions.

Example 5

Chronic and Acute Toxicity Studies

The peptide of amino acid sequence SEQ ID NO:4 was evaluated for chronic and acute toxicity in mice. Three female Black/6 mice received intraperitoneally either bolus 0.5 mg/kg or 2 mg/kg or 30 mg/kg peptide SEQ ID NO:4, or 0.5 mg/kg/day or 2 mg/kg/day peptide SEQ ID NO:4 over a 10 day period. Two days after termination of the experiments, the mice were weighed and sacrificed, and the livers, brains, spleens and kidneys were weighed. Gross necropsy showed no alteration between treated and non-treated animals, and all four organ weights were identical between treated and non-treated groups. In conclusion, the peptide of amino acid sequence SEQ ID NO:4 was found not to be toxic to mice up to the highest intraperitoneal studied dose of 30 mg/kg bolus (acute toxicity) and 2 mg/kg/day for 10 days (chronic administration).

Example 6

Serum Stability Studies

The stabilities of the peptides of amino acid sequence SEQ ID NO:4 and SEQ ID NO:49 were determined in 25% serum, and 100% serum, in terms of their half-lives. For serum stability studies, 2504 of an aqueous peptide stock solution, containing about 0.8 mg/mL peptide, were added to 2.5 mL of 25% or 100% aqueous pooled mouse serum. The peptide-serum mixture was thermostated at 37° C. After 0 min, 45 min, 60 min, 90 min, 2 h, 4 h, and 8 h, three 210 μL of the samples of peptides were taken and precipitated by the addition of 40 μL of 15% aqueous trichloroacetic acid. The samples were stored at 4° C. for 20 min and centrifuged. The supernatants were immediately frozen in dry-ice, and 220 μl, of each were analyzed on RP-HPLC and/or MALDI-MS. The results of this experiment are shown in Table 2.

TABLE 2

| Sequence Identifier | half-life in 25% serum | half-life in 100% serum |
|---|---|---|
| SEQ ID NO: 4 | 20 minutes | 5 minutes |
| SEQ ID NO: 49 | 40 minutes | 10 minutes |

Example 7

Weight Gain Studies in Mice

Figure 5:
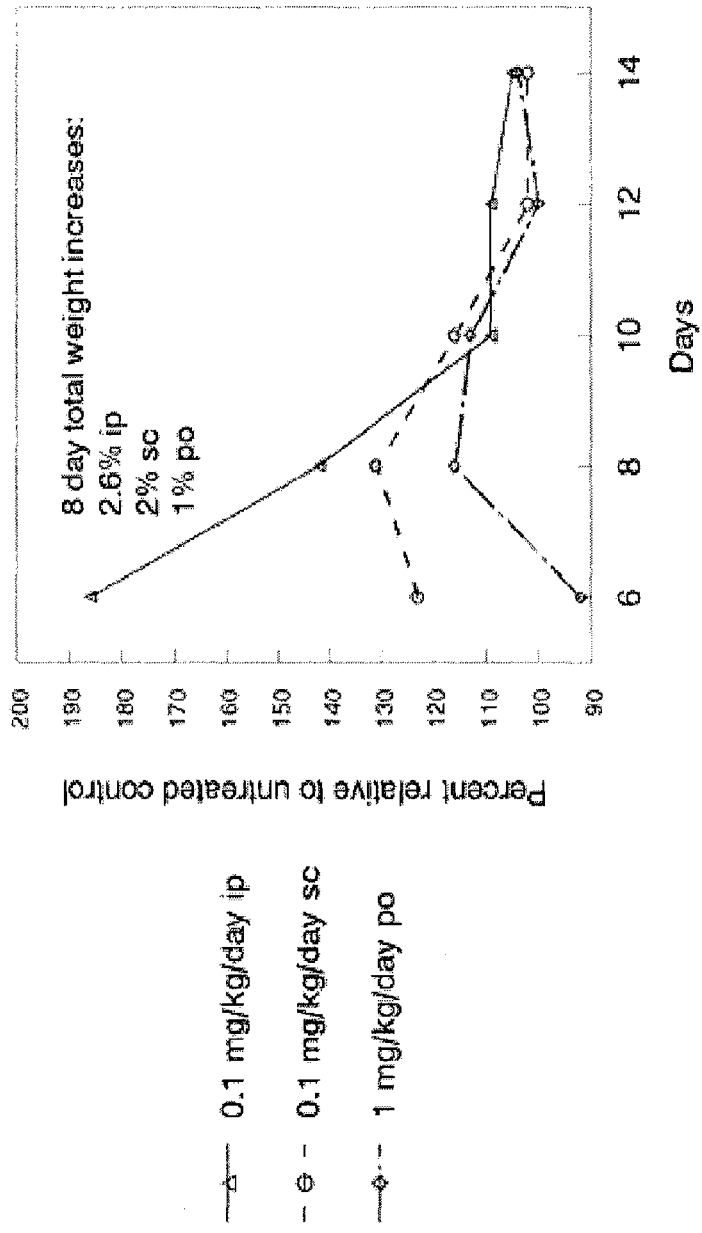
FIG. 5 shows the weight increase for BL/6 mice upon daily treatment with the peptide of amino acid sequence SEQ ID NO:4, wherein the compound was given 0.1 mg/kg/day ip (Δ), 0.1 mg/kg/day sc (○) and 1 mg/kg/day po (◇).

The peptide of amino acid sequence SEQ ID NO:4 was tested for its ability to cause weight gain in animals. BL/6 mice were treated with the peptide with daily administrations of 0.1 mg/kg/day ip, 0.1 mg/kg/day subcutaneous (sc) or 1 mg/kg/day oral (po). FIG. 5 records weight increase observed for the mice upon treatment. As shown, all three forms of administration cause increase in weight gain for the first 10 days of treatment, as compared to the untreated control.

Example 8

In Vivo Effects in a Mouse Model of Human Breast Cancer

Figure 6:
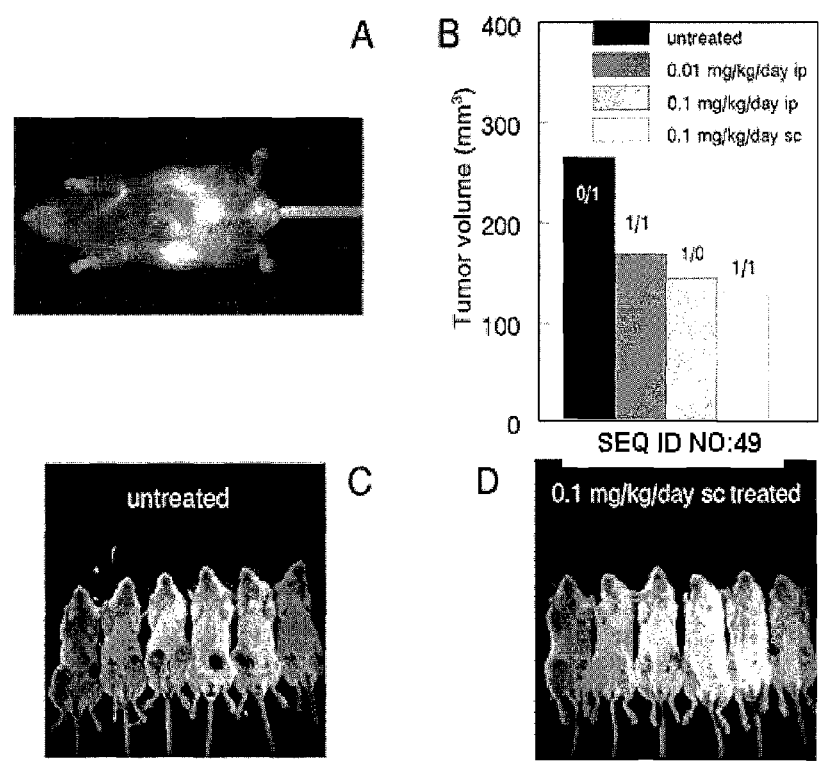
FIG. 6, comprising

The therapeutic potential of the new ObR antagonists was assessed by their in vivo effects in a mouse model of human breast cancer. The peptide of amino acid sequence SEQ ID NO:49 was used for studying the ObR-inhibitory activity in the CNS. Upon intraperitoneal administration to Balb/c mice, at 70 minutes after the administration the Alexa 680-labeled peptide of amino acid sequence SEQ ID NO:49 was distributed into the usual peptide elimination organs: the kidneys, the urinary bladder, the liver and the rectum (FIG. 6A). In addition, the peptide migrated into the tail, limbs and the brain (suggesting penetration across the blood-brain barrier).

In an experiment to determine the effects of the peptides of the invention on human breast cancer progression, $5 \times 10^6$ MCF-7 cells were transplanted under the skin of nu/nu Swiss nude mice (omitting the leptin administration taught by Mauro et al., 2007, Cancer Res. 67:3412). The tumors (injected into both sides of 6 mice per group) were readily established reaching 2-3 mm in diameter in 2 weeks. Intraperitoneal treatment with the peptide of amino acid sequence SEQ ID NO:49 reduced the tumor volume and weight in a dose-dependent manner. FIG. 6B shows the tumor volume on day 51 (38 days after treatment initiation, wherein the volume is calculated as $a^2 \times b \times 0.52$ (mm$^2$). The numbers above the bars indicate the number of disappeared/immeasurable lesions (calculated as 2 mm in each direction). After 5.5 weeks of treatment with a daily dose of 0.1 mg/kg of the peptide of amino acid sequence SEQ ID NO:49, the average tumor volume was reduced to 55% of that measured in untreated, control mice. Even greater tumor growth inhibition was obtained when the same dose of the peptide of amino acid sequence SEQ ID NO:49 was injected subcutaneously between the two lesions (49% tumor volume). FIG. 6C shows mice bearing tumor xenographs on day 52 and left untreated. FIG. 6D shows mice on day 52 (39 days after treatment initiation) treated with 0.1 mg/kg/day peptide subcutaneously between the two lesiona. The tumor size was reduced throughout the 17-day examination period. These studies suggest that the peptide of amino acid sequence SEQ ID NO:49 is a potent inhibitor of leptin-dependent breast cancer growth, and unlike other chemotherapy measures, may be administered subcutaneously without any loss of the in vivo efficacy.

Example 9

In Vivo Effects in a Mouse Model of Weight Gain

To determine whether the full antagonist peptide of amino acid sequence SEQ ID NO:4 and the partial agonist/antagonist peptide of amino acid sequence SEQ ID NO:54 have the same CNS effects, growing mice were injected intraperitoneally for 11 days with both of these peptide derivatives as well as with an antibacterial peptide (SEQ ID NO:57; Cudic et al., 2002, Peptides 23:2071) as negative control at a 0.4 mg/kg/day dose. The fitted growth curve of the control peptide-treated mice closely followed the 1.3 g expected weight increase of 6.5-weeks old mice fed with 6% fat laboratory diet (FIG. 7A).

Mice treated with the antibacterial peptide gained 1.3 g that equals the 11-day expected weight gain of these animals. Intraperitoneal administration of peptide of amino acid sequence SEQ ID NO:4 induced an additional 45% weight gain by day 11 representing 2% net total body weight (tbw) increase relative to mice treated with an unrelated control peptide. In contrast, the partial agonist peptide of amino acid sequence SEQ ID NO:54 inhibited normal growth by 10%, corresponding to a 0.8% net total body weight loss.

Figure 7:
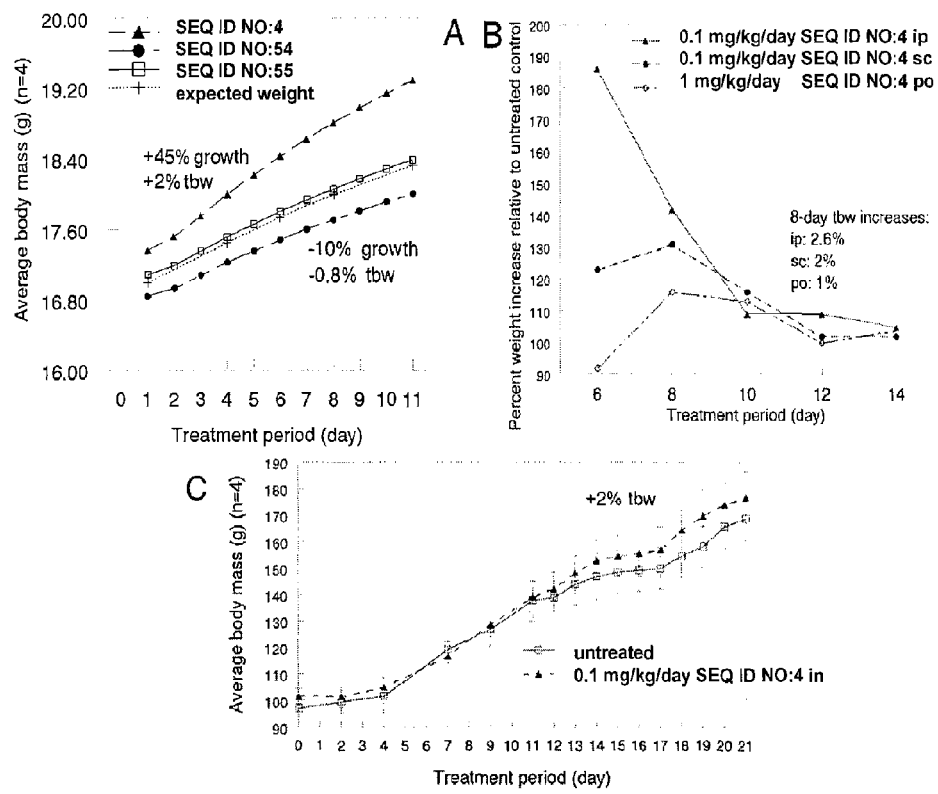
FIG. 7, comprising

While mice receiving peptide of amino acid sequence SEQ ID NO:4 gained an additional 0.6-0.7 g, mice treated with peptide of amino acid sequence SEQ ID NO:54 gained 0.1-0.2 g less than the controls indicating that at this low dose the selective antagonist did indeed act as an inhibitor of ObR functions, but also that the partial antagonist acted the opposite manner (FIG. 7A).

The therapeutic utility of full ObR antagonists was studied further by the ability of peptide of amino acid sequence SEQ ID NO:4 to increase the appetite of normal, growing mice as measured by accelerated weight gain and increased food intake upon various modes of peptide administration. Studies were run on 7-week old normal C57BL/6 mice. When added intraperitoneally, subcutaneously or orally daily, the mice gained weight, sometimes significantly, at the early-middle periods of treatment (FIG. 7B). While 0.1 mg/kg/day intraperitoneal administration immediately increased the relative body mass (compared to untreated animals), subcutaneous or oral administration was efficacious somewhat later (FIG. 7B). An optimal treatment time appeared to be 8 days, when the net body weight gains amounted to 2.6%, 2% and 1%, respectively. The increase in food intake was correlated with the additional weight gain only in week 2, when the treatment was most efficacious and only in the intraperitoneally treated group (+14%). Necropsy of the major organs showed no signs of toxicity. In control experiments, 0.1 mg/kg/day leptin added intraperitoneally, as expected, reduced normal weight gain (compared to untreated mice) by 5% at day 8. This effect was completely reversed with concomitant addition of 0.1 mg/kg/day peptide of amino acid sequence SEQ ID NO:4, the mice gaining 40% more weight than controls. The beneficial effects of all administration modes appeared to end at day 14 suggesting that the animals became resistant to ObR antagonist treatment. Interestingly, increasing subcutaneous or oral dosing (1 mg/kg/day and 10 mg/kg/day, respectively) was contra-indicated in terms of body weight increases. In addition, in a retrospective analysis of the body weights of the toxicity study, the highest level of weight gain could be documented at the lowest doses above 0.5 mg/kg bolus or 2 mg/kg/day. This situation is similar to clinical applications of leptin where emerging resistance to treatment is frequently observed.

Since leptin resistance is thought to be related, at least in part, to inefficient BBB penetration, studies were performed to determine whether resistance to treatment with the peptide of amino acid sequence SEQ ID NO:4 was also observed when the BBB did not pose a limit to CNS entry. A convenient way of studying this phenomenon is using intranasal drug delivery that bypasses BBB limits. The peptide of amino acid sequence SEQ ID NO:4 was delivered to the nasal cavity of growing male F334 rats over a 3-week period at 0.1 mg/kg/day and the weight gain was compared to animals receiving physiological salt only. Apparently the animals were stressed by the procedure because even the control rats experienced less weight gain than they were expected (72 g vs 78 g) considering their age and diet. Nevertheless, the animals treated with the peptide of amino acid sequence SEQ ID NO:4 gained on average 3.5 g more, corresponding to 2% net total body weight gain, relative to their untreated counterparts (FIG. 7C). Although the weight gain increase was maximal at day 19, extended dosing did not induce any appreciable resistance. From a general pharmacological standpoint this suggested that after a short initial treatment exogenous peripheral leptin addition might saturate BBB-resident ObRs resulting in the inability of leptin to enter the brain. In terms of cachexia control, ObR antagonists such as the peptides of amino acid sequence SEQ ID NO:4 and SEQ ID NO:49 can have significant therapeutic potential when administered in an on-off parentheral schedule or intranasally. In one aspect, the ObR antagonist studies herein significantly reduced tumor size and increased appetite, properties that can be extremely beneficial for the treatment of leptin-mediated cancer as well as cancer-related cachexia.

Example 10

Effects in a Rheumatoid Arthritis Model in the Rat

Female Wistar rats, aged 8-10 weeks, were injected subcutaneously at the base of the tail with 1 mg of heat killed *Mycobacterium tuberculosis* suspended in 100 µl of squalane. One day after the first signs of arthritis appeared (usually around 10 to 12 days later), rats were subcutaneously injected on 3 consecutive days with leptin protein (0.05 mg/kg), the peptide of amino acid sequence SEQ ID NO:49 (0.1 mg/kg) or microbial peptide of amino acid sequence SEQ ID NO:55 (0.1 mg/kg).

Figure 8:
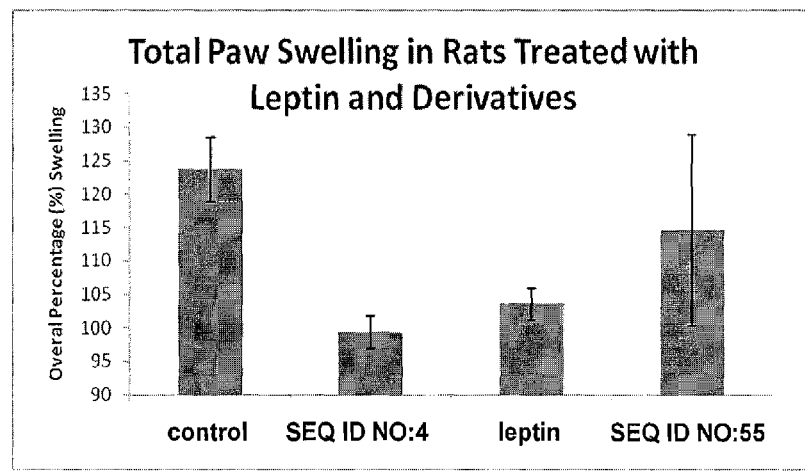
FIG. 8 shows the total paw swelling in a rat rheumatoid arthritis model, Rats were treated with leptin, the peptide of amino acids SEQ ID NO:4, or the microbial peptide of SEQ ID NO:55.
Figure 9:
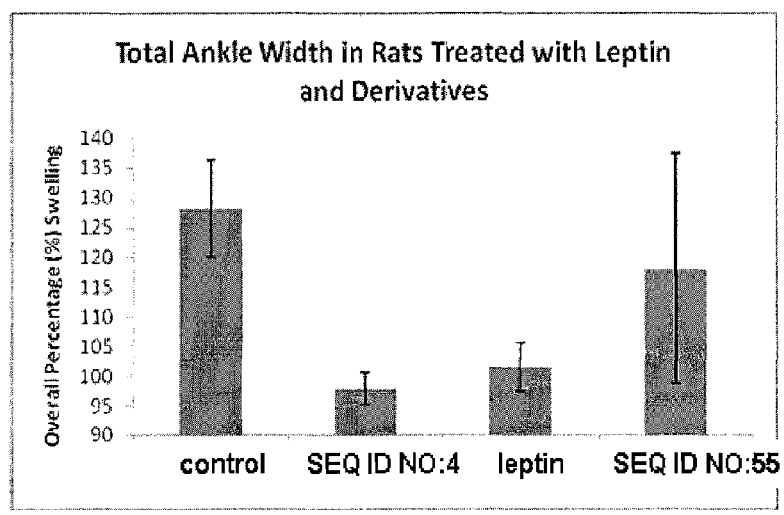
FIG. 9 shows the total ankle width in a rat rheumatoid arthritis model. Rats were treated with leptin, the peptide of amino acids SEQ ID NO:4, or the microbial peptide of SEQ ID NO:55.
Figure 10:
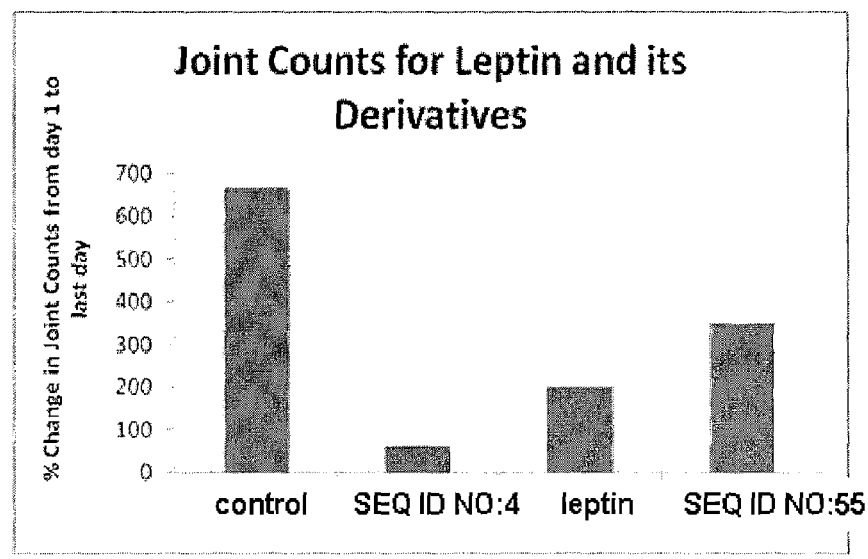
FIG. 10 shows a count of the number of arthritic joints in a rat rheumatoid arthritis model. Rats were treated with leptin, the peptide of amino acids SEQ ID NO:4, or the microbial peptide of SEQ ID NO:55.

Arthritis severity was scored daily using 5 parameters: rat weight; number of arthritic joints; and, by using digital calipers, paw thickness, paw width, and ankle width. All procedures were performed under general anesthesia with isofluorane, and analgesics (buprenorphine) were given to relieve pain. Paw thickness, paw width, and ankle width, measurements were then combined and averaged for each group to give an overall assessment of the severity of arthritis for each peptide tested. The results are shown in FIGS. 8-10.

The disclosures of each and every patent, patent application, and publication cited herein are hereby incorporated herein by reference in their entirety. One skilled in the art will readily appreciate that the present invention is well adapted to carry out the objects and obtain the ends and advantages mentioned, as well as those inherent therein. While the invention has been disclosed with reference to specific embodiments, it is apparent that other embodiments and variations of this invention may be devised by others skilled in the art without departing from the true spirit and scope used in the practice of the invention. The appended claims are intended to be construed to include all such embodiments and equivalent variations.

What is claimed:

1. A compound according to Formula (I):

$$X^1\text{-M-SEQ ID NO: 2} \tag{I}$$

or a salt thereof, wherein:
SEQ ID NO:2 represents $Xaa_1$-Glu-Nva-Val-Ala-Leu-Ser-$Xaa_2$-$Xaa_3$, wherein:
$Xaa_1$ is absent or is a hydroxylated acyclic amino acid;
$Xaa_2$ is Arg or N-MeArg;
$Xaa_3$ is an aliphatic amino acid; and,
$X^1$-M represents an optional group comprising a tagging element conjugated to the N-terminus of said amino acid sequence SEQ ID NO:2, wherein:
$X^1$ represents said tagging element, wherein said tagging element is selected from the group consisting of a transduction domain and a detection label; and,
-M- represents a single bond or an optional linking group forming a covalent linkage between said tagging element and said amino acid sequence SEQ ID NO:2.

2. The compound of claim 1, or a salt thereof, wherein -M- consists of a single bond, an amino acid or a peptide.

3. The compound of claim 1, or a salt thereof, wherein said tagging element is directly linked at its C-terminus to -M-.

4. The compound of claim 1, or a salt thereof, wherein said tagging element is a transduction domain comprising an amino acid sequence selected from the group consisting of Tyr-Gly-Arg-Lys-Lys-Arg-Arg-Gln-Arg-Arg-Arg [SEQ ID NO:10], Arg-Lys-Lys-Arg-Arg-Gln-Arg-Arg-Arg [SEQ ID NO:11], Gly-Arg-Lys-Lys-Arg-Arg-Gln-Arg-Arg-Arg-Gly-Tyr-Lys-Cys [SEQ ID NO:12], Tyr-Gly-Arg-Lys-Lys-Arg-Arg-Gln-Arg-Arg-Arg-Gly [SEQ ID NO:13], Gly-Arg-Lys-Lys-Arg-Arg-Gln-Arg-Arg-Arg-Pro-Pro-Gln-Cys [SEQ ID NO:14], Gly-Arg-Lys-Lys-Arg-Arg-Gln-Arg-Arg-Arg-Pro-Pro-Gln [SEQ ID NO:15], Tyr-Ala-Arg-Lys-Ala-Arg-Arg-Gln-Ala-Arg-Arg [SEQ ID NO:16], Tyr-Ala-Arg-Ala-Ala-Ala-Arg-Gln-Ala-Arg-Ala [SEQ ID NO:17], Tyr-Ala-Arg-Ala-Ala-Arg-Arg-Ala-Ala-Arg-Arg [SEQ ID NO:18], Tyr-Ala-Arg-Ala-Ala-Arg-Arg-Ala-Ala-Arg-Ala [SEQ ID NO:19], Arg-Gln-Ile-Lys-Ile-Trp-Phe-Gln-Asn-Arg-Arg-Met-Lys-Trp-Lys-Lys [SEQ ID NO:20], Arg-Gln-Ile-Lys-Ile-Trp-Phe-Pro-Asn-Arg-Arg-Met-Lys-Trp-Lys-Lys [SEQ ID NO:21], Lys-Lys-Trp-Lys-Met-Arg-Arg-Asn-Gln-Phe-Trp-Val-Lys-Val-Gln-Arg [SEQ ID NO:22], Arg-Arg-Trp-Arg-Arg-Trp-Trp-Arg-Arg-Trp-Trp-Arg-Arg-Trp-Arg-Arg [SEQ ID NO:23], Arg-Arg-Met-Lys-Trp-Lys-Lys [SEQ ID NO:24], Apa-Arg-Gln-Ile-Lys-Ile-Trp-Phe-Gln-Asn-Arg-Arg-Met-Lys-Trp-Lys-Lys [SEQ ID NO:25], Apa-Arg-Gln-Ile-Lys-Ile-Trp-Phe-Pro-Asn-Arg-Arg-Met-Lys-Trp-Lys-Lys [SEQ ID NO:26], Arg-Arg-Arg-Arg-Arg-Arg-Arg [SEQ ID NO:27], Arg-Arg-Arg-Arg-Arg-Arg-Arg-Arg-Arg [SEQ ID NO:28], Asp-Ala-Ala-Thr-Arg-Ser-Ala-Ala-Ser-Arg-Pro-Thr-Glu-Arg-Pro-Arg-Ala-Pro-Ala-Arg-Ser-Ala-Ser-Arg-Pro-Arg-Arg-Pro-Val-Glu [SEQ ID NO:29], Gly-Ala-Leu-Phe-Leu-Gly-Trp-Leu-Gly-Ala-Ala-Gly-Ser-Thr-Met-Gly [SEQ ID NO:30], Gly-Ala-Leu-Phe-Leu-Gly-Phe-Leu-Gly-Ala-Ala-Gly-Ser-Thr-Met-Gly-Ala-Trp-Ser-Gln-Pro-Lys-Ser-Lys-Arg-Lys-Val [SEQ ID NO:31], Met-Gly-Leu-Gly-Leu-His-Leu-Leu-Val-Leu-Ala-Ala-Ala-Leu-Gln-Gly-Ala-Trp-Ser-Gln-Pro-Lys-Lys-Lys-Arg-Lys-Val [SEQ ID NO:32], Pro-Leu-Ser-Ser-Ile-Phe-Ser-Arg-Ile-Gly-Asp-Pro [SEQ ID NO:33], Phe-Trp-Arg-Gly-Asp-Leu-Val-Phe-Asp-Phe-Gln-Val [SEQ ID NO:34], Lys-Phe-Thr-Ile-Val-Phe-Pro-His-Asn-Gln-Lys-Gly-Asn-Trp-Lys-Asn-Val-Pro-Ser-Asn-Tyr-His-Tyr-Cys-Pro [SEQ ID NO:35], Ala-Lys-Arg-Ala-Arg-Leu-Ser-Thr-Ser-Phe-Asn-Pro-Val-Tyr-Pro-Tyr-Glu-Asp-Glu-Ser [SEQ ID NO:36], Gly-Trp-Thr-Leu-Asn-Ser-Ala-Gly-Tyr-Leu-Leu-Gly-Lys-Ile-Asn-Leu-Lys-Ala-Leu-Ala-Ala-Leu-Ala-Lys-Lys-Ile-Leu [SEQ ID NO:37], Arg-Gly-Gly-Arg-Leu-Ser-Tyr-Ser-Arg-Arg-Arg-Phe-Ser-Thr-Ser-Thr-Gly-Arg [SEQ ID NO:38], Ala-Ala-Val-Ala-Leu-Leu-Pro-Ala-Val-Leu-Leu-Ala-Leu-Leu-Ala-Pro [SEQ ID NO:39], Ala-Ala-Val-Leu-Leu-Pro-Val-Leu-Leu-Ala-Ala-Pro [SEQ ID NO:40], Val-Thr-Val-Leu-Ala-Leu-Gly-Ala-Leu-Ala-Gly-Val-Gly-Val-Gly [SEQ ID NO:41], Val-Ala-Tyr-Ile-Ser-Arg-Gly-Gly-Val-Ser-Thr-Tyr-Tyr-Ser-Asp-Thr-Val-Lys-Gly-Arg-Phe-Thr-Arg-Gln-Lys-Tyr-Asn-Lys-Arg-Ala [SEQ ID NO:42], Lys-Leu-Ala-Leu-Lys-Leu-Ala-Leu-Lys-Ala-Leu-Lys-Ala-Ala-Leu-Lys-Leu-Ala [SEQ ID NO:43], Trp-Glu-Ala-Lys-Leu-Ala-Lys-Ala-Leu-Ala-Lys-Ala-Leu-Ala-Lys-His-Leu-Ala-Lys-Ala-Leu-Ala-Lys-Ala-Leu-Lys-Ala-Cys-Glu-Ala [SEQ ID NO:44], Arg-Arg-Gln-Arg-Arg-Thr-Ser-Lys-Leu-Met-Lys-Arg [SEQ ID NO:45] and Val-Asp-Lys-Gly-Ser-Tyr-Leu-Pro-Arg-Pro-Thr (NAcGal)-Pro-Pro-Arg-Pro-Ile-Tyr-Asn-Arg-Asn [SEQ ID NO:46].

5. The compound of claim 4, or a salt thereof, wherein -M- consists of an amino acid or peptide.

6. The compound of claim 4, or a salt thereof, wherein -M- consists of a single bond.

7. The compound of claim 1, or a salt thereof, wherein $Xaa_1$ is absent.

8. The compound of claim 1, or a salt thereof, wherein $Xaa_1$ is a hydroxylated acyclic amino acid selected from the group consisting of serine, (D)-serine, threonine, (D)-threonine, (L)-allo-threonine, (D)-allo-threonine, (L)-isoserine, (D)-isoserine, (L)-β-homoserine, (D)-β-homoserine, (L)-homoserine, and (D)-homoserine.

9. The compound of claim 8, or a salt thereof, wherein $Xaa_1$ is (D)-serine.

10. The compound of claim 8, or a salt thereof, wherein $Xaa_1$ is threonine.

11. The compound of claim 1, or a salt thereof, wherein $Xaa_2$ is Arg.

12. The compound of claim 1, or a salt thereof, wherein $Xaa_2$ is N-MeArg.

13. The compound of claim 1, or a salt thereof, wherein $Xaa_3$ is an aliphatic amino acid selected from the group consisting of bAla, $bAlaNH_2$, Acp and $AcpNH_2$.

14. The compound of claim 1, or a salt thereof, selected from the group consisting of the peptide of amino acid sequence Thr-Glu-Nva-Val-Ala-Leu-Ser-Arg-Acp [SEQ ID NO:3], the peptide of amino acid sequence Thr-Glu-Nva-Val-Ala-Leu-Ser-Arg-$AcpNH_2$ [SEQ ID NO:4], the peptide of amino acid sequence (D)-Ser-Glu-Nva-Val-Ala-Leu-Ser-N-MeArg-bAla [SEQ ID NO:5], the peptide of amino acid sequence (D)-Ser-Glu-Nva-Val-Ala-Leu-Ser-N-MeArg-$bAlaNH_2$ [SEQ ID NO:6], the peptide of amino acid sequence alloThr-Glu-Nva-Val-Ala-Leu-Ser-Arg-$AcpNH_2$ [SEQ ID NO:49], the peptide of amino acid sequence Thr-Glu-Nva-Val-Ala-Leu-Ser-Arg-$NvaNH_2$ [SEQ ID NO:50], the peptide of amino acid sequence Glu-Nva-Val-Ala-Leu-Ser-Arg-$AcpNH_2$ [SEQ ID NO:51] and the peptide of amino acid sequence (D)-Ser-Glu-Nva-Val-Ala-Leu-Ser-Arg-$AcpNH_2$ [SEQ ID NO:52].

15. A pharmaceutical composition comprising a compound according to Formula (I):

$$X^1\text{-M-SEQ ID NO: 2} \quad (I)$$

or a salt thereof, wherein:
SEQ ID NO:2 represents $Xaa_1$-Glu-Nva-Val-Ala-Leu-Ser-$Xaa_2$-$Xaa_3$, wherein:
$Xaa_1$ is absent or is a hydroxylated acyclic amino acid;
$Xaa_2$ is Arg or N-MeArg;
$Xaa_3$ is an aliphatic amino acid; and,
$X^1$-M represents an optional group comprising a tagging element conjugated to the N-terminus of said amino acid sequence SEQ ID NO:2, wherein:
$X^1$ represents said tagging element, wherein said tagging element is selected from the group consisting of a transduction domain and a detection label;
-M- represents a single bond or an optional linking group forming a covalent linkage between said tagging element and said amino acid sequence SEQ ID NO:2;
and a pharmaceutically acceptable carrier.

16. The pharmaceutical composition of claim 15, wherein said compound is selected from the group consisting of the peptide of amino acid sequence Thr-Glu-Nva-Val-Ala-Leu-Ser-Arg-Acp [SEQ ID NO:3], the peptide of amino acid sequence Thr-Glu-Nva-Val-Ala-Leu-Ser-Arg-$AcpNH_2$ [SEQ ID NO:4], the peptide of amino acid sequence (D)-Ser-Glu-Nva-Val-Ala-Leu-Ser-N-MeArg-bAla [SEQ ID NO:5], the peptide of amino acid sequence (D)-Ser-Glu-Nva-Val-Ala-Leu-Ser-N-MeArg-$bAlaNH_2$ [SEQ ID NO:6], the peptide of amino acid sequence alloThr-Glu-Nva-Val-Ala-Leu-Ser-Arg-$AcpNH_2$ [SEQ ID NO:49], the peptide of amino acid sequence Thr-Glu-Nva-Val-Ala-Leu-Ser-Arg-$NvaNH_2$ [SEQ ID NO:50], the peptide of amino acid sequence Glu-Nva-Val-Ala-Leu-Ser-Arg-$AcpNH_2$ [SEQ ID NO:51] and the peptide of amino acid sequence (D)-Ser-Glu-Nva-Val-Ala-Leu-Ser-Arg-$AcpNH_2$ [SEQ ID NO:52], and salts thereof.

17. The compound according to claim 1 which is the peptide of the amino acid sequence alloThr-Glu-Nva-Val-Ala-Leu-Ser-Arg-$AcpNH_2$ [SEQ ID NO:49], or salt thereof.

18. The pharmaceutical composition of claim 15, wherein the compound is the peptide of the amino acid sequence alloThr-Glu-Nva-Val-Ala-Leu-Ser-Arg-$AcpNH_2$ [SEQ ID NO:49], or salt thereof.

19. A compound according to the formula:

$X^1$-M-SEQ ID NO:47 or a salt thereof, wherein:
SEQ ID NO:47 represents the amino acid sequence Thr-Glu-Nva-Nva-Ala-Leu-Ser-Arg-$NvaNH_2$;
$X^1$-M represents an optional group comprising a tagging element conjugated to the N-terminus of said amino acid sequence SEQ ID NO:47, wherein:
$X^1$ represents said tagging element, wherein said tagging element is selected from the group consisting of a transduction domain and a detection label; and,
-M- represents a single bond or an optional linking group forming a covalent linkage between said tagging element and said amino acid sequence SEQ ID NO:47.

20. The compound according to claim 19 which is the peptide of the amino acid sequence Thr-Glu-Nva-Nva-Ala-Leu-Ser-Arg-$NvaNH_2$ (SEQ ID NO:47), or salt thereof.

21. A pharmaceutical composition comprising a compound according to claim 19, and a pharmaceutically acceptable carrier.

22. The pharmaceutical composition of claim 21, wherein the compound is the peptide of the amino acid sequence Thr-Glu-Nva-Nva-Ala-Leu-Ser-Arg-$NvaNH_2$ (SEQ ID NO:47), or salt thereof.

* * * * *

SEQUENCE LISTING

```
<160> NUMBER OF SEQ ID NOS: 58

<210> SEQ ID NO 1
<211> LENGTH: 146
<212> TYPE: PRT
<213> ORGANISM: Homo sapiens

<400> SEQUENCE: 1

Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ala
            20                  25                  30

Lys Gln Arg Val Thr Gly Leu Asp Phe Ile Pro Gly Leu His Pro Ile
        35                  40                  45

Leu Ser Leu Ser Lys Met Asp Gln Thr Leu Ala Val Tyr Gln Gln Val
    50                  55                  60

Leu Thr Ser Leu Pro Ser Gln Asn Val Leu Gln Ile Ala Asn Asp Leu
65                  70                  75                  80

Glu Asn Leu Arg Asp Leu Leu His Leu Leu Ala Phe Ser Lys Ser Cys
                85                  90                  95
```

```
Ser Leu Pro Gln Thr Ser Gly Leu Gln Lys Pro Glu Ser Leu Asp Gly
            100                 105                 110

Val Leu Glu Ala Ser Leu Tyr Ser Thr Glu Val Val Ala Leu Ser Arg
        115                 120                 125

Leu Gln Gly Ser Leu Gln Asp Ile Leu Gln Gln Leu Asp Val Ser Pro
    130                 135                 140

Glu Cys
145

<210> SEQ ID NO 2
<211> LENGTH: 9
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: zero amino acid or hydroxylated amino acid
<220> FEATURE:
<221> NAME/KEY: MOD_RES
<222> LOCATION: (3)..(3)
<223> OTHER INFORMATION: Nva
<220> FEATURE:
<221> NAME/KEY: MOD_RES
<222> LOCATION: (8)..(8)
<223> OTHER INFORMATION: arginine or N-methyl arginine
<220> FEATURE:
<221> NAME/KEY: MOD_RES
<222> LOCATION: (9)..(9)
<223> OTHER INFORMATION: aliphatic amino acid

<400> SEQUENCE: 2

Xaa Glu Xaa Val Ala Leu Ser Xaa Xaa
1               5

<210> SEQ ID NO 3
<211> LENGTH: 9
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (3)..(3)
<223> OTHER INFORMATION: Nva
<220> FEATURE:
<221> NAME/KEY: MOD_RES
<222> LOCATION: (9)..(9)
<223> OTHER INFORMATION: Acp

<400> SEQUENCE: 3

Thr Glu Xaa Val Ala Leu Ser Arg Xaa
1               5

<210> SEQ ID NO 4
<211> LENGTH: 9
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (3)..(3)
<223> OTHER INFORMATION: Nva
<220> FEATURE:
<221> NAME/KEY: MOD_RES
<222> LOCATION: (9)..(9)
<223> OTHER INFORMATION: 6-aminocaproamide
```

```
<220> FEATURE:
<221> NAME/KEY: MOD_RES
<222> LOCATION: (9)..(9)
<223> OTHER INFORMATION: 6-aminocapramide

<400> SEQUENCE: 4

Thr Glu Xaa Val Ala Leu Ser Arg Xaa
1               5

<210> SEQ ID NO 5
<211> LENGTH: 9
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: (D)-serine
<220> FEATURE:
<221> NAME/KEY: MOD_RES
<222> LOCATION: (3)..(3)
<223> OTHER INFORMATION: Nva
<220> FEATURE:
<221> NAME/KEY: MOD_RES
<222> LOCATION: (8)..(8)
<223> OTHER INFORMATION: N-methyl-arginine
<220> FEATURE:
<221> NAME/KEY: MOD_RES
<222> LOCATION: (9)..(9)
<223> OTHER INFORMATION: bAla

<400> SEQUENCE: 5

Xaa Glu Xaa Val Ala Leu Ser Xaa Xaa
1               5

<210> SEQ ID NO 6
<211> LENGTH: 9
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: D-serine
<220> FEATURE:
<221> NAME/KEY: MOD_RES
<222> LOCATION: (3)..(3)
<223> OTHER INFORMATION: Nva
<220> FEATURE:
<221> NAME/KEY: MOD_RES
<222> LOCATION: (8)..(8)
<223> OTHER INFORMATION: N-methyl-arginine
<220> FEATURE:
<221> NAME/KEY: MOD_RES
<222> LOCATION: (9)..(9)
<223> OTHER INFORMATION: beta-aminopropionamide

<400> SEQUENCE: 6

Xaa Glu Xaa Val Ala Leu Ser Xaa Xaa
1               5

<210> SEQ ID NO 7
<211> LENGTH: 41
<212> TYPE: PRT
<213> ORGANISM: Artificial Sequence
<220> FEATURE:
<223> OTHER INFORMATION: chemicaly synthesized
<220> FEATURE:
<221> NAME/KEY: MOD_RES
<222> LOCATION: (1)..(1)
<223> OTHER INFORMATION: 1-cyclohexane-carboxylic acid
```

```
<220> FEATURE:
<221> NAME/KEY: MOD_RES
<222> LOCATION: (21)..(21)
<223> OTHER INFORMATION: Dbu
<220> FEATURE:
<221> NAME/KEY: MOD_RES
<222> LOCATION: (41)..(41)
<223> OTHER INFORMATION: 1-cyclohexane-carboxylic acid

<400> SEQUENCE: 7

Xaa Arg Pro Asp Lys Pro Arg Pro Tyr Leu Pro Arg Pro Arg Pro Pro
1               5                   10                  15

Arg Pro Val Arg Xaa Arg Val Pro Arg Pro Arg Pro Arg Pro Pro Leu
            20                  25                  30

Tyr Pro Arg Pro Lys Asp Pro Arg Xaa
        35                  40

<210> SEQ ID NO 8
<211> LENGTH: 12
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: 3,5-diiodotyrosine
<220> FEATURE:
<221> NAME/KEY: MOD_RES
<222> LOCATION: (2)..(2)
<223> OTHER INFORMATION: O-(beta-glucosyl)-serine
<220> FEATURE:
<221> NAME/KEY: MOD_RES
<222> LOCATION: (12)..(12)
<223> OTHER INFORMATION: N2(3)-acetyl-diaminopopionic acid
<220> FEATURE:
<221> NAME/KEY: MOD_RES
<222> LOCATION: (12)..(12)
<223> OTHER INFORMATION: N2(3)-acetyl-diaminopropionic acid

<400> SEQUENCE: 8

Xaa Xaa Thr Glu Val Val Ala Leu Ser Arg Leu Xaa
1               5                   10

<210> SEQ ID NO 9
<211> LENGTH: 9
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: N-acetyl-threonine
<220> FEATURE:
<221> NAME/KEY: MOD_RES
<222> LOCATION: (3)..(3)
<223> OTHER INFORMATION: Nva
<220> FEATURE:
<221> NAME/KEY: MOD_RES
<222> LOCATION: (9)..(9)
<223> OTHER INFORMATION: 6-aminocaproamide
<220> FEATURE:
<221> NAME/KEY: MOD_RES
<222> LOCATION: (9)..(9)
<223> OTHER INFORMATION: 6-aminocapramide

<400> SEQUENCE: 9

Xaa Glu Xaa Val Ala Leu Ser Arg Xaa
1               5
```

<210> SEQ ID NO 10
<211> LENGTH: 11
<212> TYPE: PRT
<213> ORGANISM: Artificial Sequence
<220> FEATURE:
<223> OTHER INFORMATION: chemically synthesized

<400> SEQUENCE: 10

Tyr Gly Arg Lys Lys Arg Arg Gln Arg Arg Arg
1               5                   10

<210> SEQ ID NO 11
<211> LENGTH: 9
<212> TYPE: PRT
<213> ORGANISM: Artificial Sequence
<220> FEATURE:
<223> OTHER INFORMATION: chemically synthesized

<400> SEQUENCE: 11

Arg Lys Lys Arg Arg Gln Arg Arg Arg
1               5

<210> SEQ ID NO 12
<211> LENGTH: 14
<212> TYPE: PRT
<213> ORGANISM: Artificial Sequence
<220> FEATURE:
<223> OTHER INFORMATION: chemically synthesized

<400> SEQUENCE: 12

Gly Arg Lys Lys Arg Arg Gln Arg Arg Arg Gly Tyr Lys Cys
1               5                   10

<210> SEQ ID NO 13
<211> LENGTH: 12
<212> TYPE: PRT
<213> ORGANISM: Artificial Sequence
<220> FEATURE:
<223> OTHER INFORMATION: chemically synthesized

<400> SEQUENCE: 13

Tyr Gly Arg Lys Lys Arg Arg Gln Arg Arg Gly
1               5                   10

<210> SEQ ID NO 14
<211> LENGTH: 14
<212> TYPE: PRT
<213> ORGANISM: Artificial Sequence
<220> FEATURE:
<223> OTHER INFORMATION: chemically synthesized

<400> SEQUENCE: 14

Gly Arg Lys Lys Arg Arg Gln Arg Arg Arg Pro Pro Gln Cys
1               5                   10

<210> SEQ ID NO 15
<211> LENGTH: 13
<212> TYPE: PRT
<213> ORGANISM: Artificial Sequence
<220> FEATURE:
<223> OTHER INFORMATION: chemically synthesized

<400> SEQUENCE: 15

Gly Arg Lys Lys Arg Arg Gln Arg Arg Arg Pro Pro Gln
1               5                   10

<210> SEQ ID NO 16

```
<211> LENGTH: 11
<212> TYPE: PRT
<213> ORGANISM: Artificial Sequence
<220> FEATURE:
<223> OTHER INFORMATION: chemically synthesized

<400> SEQUENCE: 16

Tyr Ala Arg Lys Ala Arg Arg Gln Ala Arg Arg
1               5                   10

<210> SEQ ID NO 17
<211> LENGTH: 11
<212> TYPE: PRT
<213> ORGANISM: Artificial Sequence
<220> FEATURE:
<223> OTHER INFORMATION: chemically synthesized

<400> SEQUENCE: 17

Tyr Ala Arg Ala Ala Ala Arg Gln Ala Arg Ala
1               5                   10

<210> SEQ ID NO 18
<211> LENGTH: 11
<212> TYPE: PRT
<213> ORGANISM: Artificial Sequence
<220> FEATURE:
<223> OTHER INFORMATION: chemically synthesized

<400> SEQUENCE: 18

Tyr Ala Arg Ala Ala Arg Arg Ala Ala Arg Arg
1               5                   10

<210> SEQ ID NO 19
<211> LENGTH: 11
<212> TYPE: PRT
<213> ORGANISM: Artificial Sequence
<220> FEATURE:
<223> OTHER INFORMATION: chemically synthesized

<400> SEQUENCE: 19

Tyr Ala Arg Ala Ala Arg Arg Ala Ala Arg Ala
1               5                   10

<210> SEQ ID NO 20
<211> LENGTH: 16
<212> TYPE: PRT
<213> ORGANISM: Artificial Sequence
<220> FEATURE:
<223> OTHER INFORMATION: chemically synthesized

<400> SEQUENCE: 20

Arg Gln Ile Lys Ile Trp Phe Gln Asn Arg Arg Met Lys Trp Lys Lys
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: chemically synthesized

<400> SEQUENCE: 21

Arg Gln Ile Lys Ile Trp Phe Pro Asn Arg Arg Met Lys Trp Lys Lys
1               5                   10                  15

<210> SEQ ID NO 22
<211> LENGTH: 16
```

```
<212> TYPE: PRT
<213> ORGANISM: Artificial Sequence
<220> FEATURE:
<223> OTHER INFORMATION: chemically synthesized

<400> SEQUENCE: 22

Lys Lys Trp Lys Met Arg Arg Asn Gln Phe Trp Val Lys Val Gln Arg
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: chemically synthesized

<400> SEQUENCE: 23

Arg Arg Trp Arg Arg Trp Trp Arg Arg Trp Trp Arg Arg Trp Arg Arg
1               5                   10                  15

<210> SEQ ID NO 24
<211> LENGTH: 7
<212> TYPE: PRT
<213> ORGANISM: Artificial Sequence
<220> FEATURE:
<223> OTHER INFORMATION: chemically synthesized

<400> SEQUENCE: 24

Arg Arg Met Lys Trp Lys Lys
1               5

<210> SEQ ID NO 25
<211> LENGTH: 17
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: amino pentanoic acid

<400> SEQUENCE: 25

Xaa Arg Gln Ile Lys Ile Trp Phe Gln Asn Arg Arg Met Lys Trp Lys
1               5                   10                  15

Lys

<210> SEQ ID NO 26
<211> LENGTH: 17
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: aminopentanoic acid

<400> SEQUENCE: 26

Xaa Arg Gln Ile Lys Ile Trp Phe Pro Asn Arg Arg Met Lys Trp Lys
1               5                   10                  15

Lys

<210> SEQ ID NO 27
<211> LENGTH: 7
<212> TYPE: PRT
<213> ORGANISM: Artificial Sequence
```

```
<220> FEATURE:
<223> OTHER INFORMATION: chemically synthesized

<400> SEQUENCE: 27

Arg Arg Arg Arg Arg Arg Arg
1               5

<210> SEQ ID NO 28
<211> LENGTH: 9
<212> TYPE: PRT
<213> ORGANISM: Artificial Sequence
<220> FEATURE:
<223> OTHER INFORMATION: chemically synthesized

<400> SEQUENCE: 28

Arg Arg Arg Arg Arg Arg Arg Arg Arg
1               5

<210> SEQ ID NO 29
<211> LENGTH: 30
<212> TYPE: PRT
<213> ORGANISM: Artificial Sequence
<220> FEATURE:
<223> OTHER INFORMATION: chemically synthesized

<400> SEQUENCE: 29

Asp Ala Ala Thr Arg Ser Ala Ala Ser Arg Pro Thr Glu Arg Pro Arg
1               5                   10                  15

Ala Pro Ala Arg Ser Ala Ser Arg Pro Arg Arg Pro Val Glu
            20                  25                  30

<210> SEQ ID NO 30
<211> LENGTH: 16
<212> TYPE: PRT
<213> ORGANISM: Artificial Sequence
<220> FEATURE:
<223> OTHER INFORMATION: chemically synthesized

<400> SEQUENCE: 30

Gly Ala Leu Phe Leu Gly Trp Leu Gly Ala Ala Gly Ser Thr Met Gly
1               5                   10                  15

<210> SEQ ID NO 31
<211> LENGTH: 27
<212> TYPE: PRT
<213> ORGANISM: Artificial Sequence
<220> FEATURE:
<223> OTHER INFORMATION: chemically synthesized

<400> SEQUENCE: 31

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 32
<211> LENGTH: 27
<212> TYPE: PRT
<213> ORGANISM: Artificial Sequence
<220> FEATURE:
<223> OTHER INFORMATION: chemically synthesized

<400> SEQUENCE: 32

Met Gly Leu Gly Leu His Leu Leu Val Leu Ala Ala Ala Leu Gln Gly
1               5                   10                  15
```

```
Ala Trp Ser Gln Pro Lys Lys Lys Arg Lys Val
            20                  25

<210> SEQ ID NO 33
<211> LENGTH: 12
<212> TYPE: PRT
<213> ORGANISM: Artificial Sequence
<220> FEATURE:
<223> OTHER INFORMATION: chemically synthesized

<400> SEQUENCE: 33

Pro Leu Ser Ser Ile Phe Ser Arg Ile Gly Asp Pro
1               5                   10

<210> SEQ ID NO 34
<211> LENGTH: 12
<212> TYPE: PRT
<213> ORGANISM: Artificial Sequence
<220> FEATURE:
<223> OTHER INFORMATION: chemically synthesized

<400> SEQUENCE: 34

Phe Trp Arg Gly Asp Leu Val Phe Asp Phe Gln Val
1               5                   10

<210> SEQ ID NO 35
<211> LENGTH: 25
<212> TYPE: PRT
<213> ORGANISM: Artificial Sequence
<220> FEATURE:
<223> OTHER INFORMATION: chemically synthesized

<400> SEQUENCE: 35

Lys Phe Thr Ile Val Phe Pro His Asn Gln Lys Gly Asn Trp Lys Asn
1               5                   10                  15

Val Pro Ser Asn Tyr His Tyr Cys Pro
            20                  25

<210> SEQ ID NO 36
<211> LENGTH: 20
<212> TYPE: PRT
<213> ORGANISM: Artificial Sequence
<220> FEATURE:
<223> OTHER INFORMATION: chemically synthesized

<400> SEQUENCE: 36

Ala Lys Arg Ala Arg Leu Ser Thr Ser Phe Asn Pro Val Tyr Pro Tyr
1               5                   10                  15

Glu Asp Glu Ser
            20

<210> SEQ ID NO 37
<211> LENGTH: 27
<212> TYPE: PRT
<213> ORGANISM: Artificial Sequence
<220> FEATURE:
<223> OTHER INFORMATION: chemically synthesized

<400> SEQUENCE: 37

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 38
```

```
<211> LENGTH: 18
<212> TYPE: PRT
<213> ORGANISM: Artificial Sequence
<220> FEATURE:
<223> OTHER INFORMATION: chemically synthesized

<400> SEQUENCE: 38

Arg Gly Gly Arg Leu Ser Tyr Ser Arg Arg Arg Phe Ser Thr Ser Thr
1               5                   10                  15

Gly Arg

<210> SEQ ID NO 39
<211> LENGTH: 16
<212> TYPE: PRT
<213> ORGANISM: Artificial Sequence
<220> FEATURE:
<223> OTHER INFORMATION: chemically synthesized

<400> SEQUENCE: 39

Ala Ala Val Ala Leu Leu Pro Ala Val Leu Leu Ala Leu Leu Ala Pro
1               5                   10                  15

<210> SEQ ID NO 40
<211> LENGTH: 12
<212> TYPE: PRT
<213> ORGANISM: Artificial Sequence
<220> FEATURE:
<223> OTHER INFORMATION: chemically synthesized

<400> SEQUENCE: 40

Ala Ala Val Leu Leu Pro Val Leu Leu Ala Ala Pro
1               5                   10

<210> SEQ ID NO 41
<211> LENGTH: 15
<212> TYPE: PRT
<213> ORGANISM: Artificial Sequence
<220> FEATURE:
<223> OTHER INFORMATION: chemically synthesized

<400> SEQUENCE: 41

Val Thr Val Leu Ala Leu Gly Ala Leu Ala Gly Val Gly Val Gly
1               5                   10                  15

<210> SEQ ID NO 42
<211> LENGTH: 30
<212> TYPE: PRT
<213> ORGANISM: Artificial Sequence
<220> FEATURE:
<223> OTHER INFORMATION: chemically synthesized

<400> SEQUENCE: 42

Val Ala Tyr Ile Ser Arg Gly Gly Val Ser Thr Tyr Tyr Ser Asp Thr
1               5                   10                  15

Val Lys Gly Arg Phe Thr Arg Gln Lys Tyr Asn Lys Arg Ala
            20                  25                  30

<210> SEQ ID NO 43
<211> LENGTH: 18
<212> TYPE: PRT
<213> ORGANISM: Artificial Sequence
<220> FEATURE:
<223> OTHER INFORMATION: chemically synthesized

<400> SEQUENCE: 43

Lys Leu Ala Leu Lys Leu Ala Leu Lys Ala Leu Lys Ala Ala Leu Lys
```

```
1               5                   10                  15
Leu Ala

<210> SEQ ID NO 44
<211> LENGTH: 30
<212> TYPE: PRT
<213> ORGANISM: Artificial Sequence
<220> FEATURE:
<223> OTHER INFORMATION: chemically synthesized

<400> SEQUENCE: 44

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 45
<211> LENGTH: 12
<212> TYPE: PRT
<213> ORGANISM: Artificial Sequence
<220> FEATURE:
<223> OTHER INFORMATION: chemically synthesized

<400> SEQUENCE: 45

Arg Arg Gln Arg Arg Thr Ser Lys Leu Met Lys Arg
1               5                   10

<210> SEQ ID NO 46
<211> LENGTH: 20
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (11)..(11)
<223> OTHER INFORMATION: O-(N-acetylgalactosyl)-threonine
<220> FEATURE:
<221> NAME/KEY: MOD_RES
<222> LOCATION: (11)..(11)
<223> OTHER INFORMATION: O-(N-acetylgalactosaminyl)-threonine

<400> SEQUENCE: 46

Val Asp Lys Gly Ser Tyr Leu Pro Arg Pro Xaa Pro Pro Arg Pro Ile
1               5                   10                  15

Tyr Asn Arg Asn
            20

<210> SEQ ID NO 47
<211> LENGTH: 9
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (3)..(3)
<223> OTHER INFORMATION: Nva
<220> FEATURE:
<221> NAME/KEY: MOD_RES
<222> LOCATION: (4)..(4)
<223> OTHER INFORMATION: Nva
<220> FEATURE:
<221> NAME/KEY: MOD_RES
<222> LOCATION: (9)..(9)
<223> OTHER INFORMATION: norvalinamide

<400> SEQUENCE: 47
```

Thr Glu Xaa Xaa Ala Leu Ser Arg Xaa
1               5

<210> SEQ ID NO 48
<211> LENGTH: 9
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: N-acetyl-threonine
<220> FEATURE:
<221> NAME/KEY: MOD_RES
<222> LOCATION: (3)..(3)
<223> OTHER INFORMATION: Nva
<220> FEATURE:
<221> NAME/KEY: MOD_RES
<222> LOCATION: (4)..(4)
<223> OTHER INFORMATION: Nva
<220> FEATURE:
<221> NAME/KEY: MOD_RES
<222> LOCATION: (9)..(9)
<223> OTHER INFORMATION: norvalinamide

<400> SEQUENCE: 48

Xaa Glu Xaa Xaa Ala Leu Ser Arg Xaa
1               5

<210> SEQ ID NO 49
<211> LENGTH: 9
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: allo-threonine
<220> FEATURE:
<221> NAME/KEY: MOD_RES
<222> LOCATION: (3)..(3)
<223> OTHER INFORMATION: Nva
<220> FEATURE:
<221> NAME/KEY: MOD_RES
<222> LOCATION: (9)..(9)
<223> OTHER INFORMATION: 6-aminocaproamide
<220> FEATURE:
<221> NAME/KEY: MOD_RES
<222> LOCATION: (9)..(9)
<223> OTHER INFORMATION: 6-aminocapramide

<400> SEQUENCE: 49

Xaa Glu Xaa Val Ala Leu Ser Arg Xaa
1               5

<210> SEQ ID NO 50
<211> LENGTH: 9
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (3)..(3)
<223> OTHER INFORMATION: Nva
<220> FEATURE:
<221> NAME/KEY: MOD_RES
<222> LOCATION: (9)..(9)
<223> OTHER INFORMATION: norvalinamide

<400> SEQUENCE: 50

```
Thr Glu Xaa Val Ala Leu Ser Arg Xaa
1               5
```

<210> SEQ ID NO 51
<211> LENGTH: 8
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: Nva
<220> FEATURE:
<221> NAME/KEY: MOD_RES
<222> LOCATION: (8)..(8)
<223> OTHER INFORMATION: 6-aminocaproamide
<220> FEATURE:
<221> NAME/KEY: MOD_RES
<222> LOCATION: (8)..(8)
<223> OTHER INFORMATION: 6-aminocapramide

<400> SEQUENCE: 51

```
Glu Xaa Val Ala Leu Ser Arg Xaa
1               5
```

<210> SEQ ID NO 52
<211> LENGTH: 9
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: D-serine
<220> FEATURE:
<221> NAME/KEY: MOD_RES
<222> LOCATION: (3)..(3)
<223> OTHER INFORMATION: Nva
<220> FEATURE:
<221> NAME/KEY: MOD_RES
<222> LOCATION: (9)..(9)
<223> OTHER INFORMATION: 6-aminocaproamide
<220> FEATURE:
<221> NAME/KEY: MOD_RES
<222> LOCATION: (9)..(9)
<223> OTHER INFORMATION: 6-aminocapramide

<400> SEQUENCE: 52

```
Xaa Glu Xaa Val Ala Leu Ser Arg Xaa
1               5
```

<210> SEQ ID NO 53
<211> LENGTH: 9
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: 4-hydroxyproline
<220> FEATURE:
<221> NAME/KEY: MOD_RES
<222> LOCATION: (3)..(3)
<223> OTHER INFORMATION: Nva
<220> FEATURE:
<221> NAME/KEY: MOD_RES
<222> LOCATION: (9)..(9)
<223> OTHER INFORMATION: 6-aminocaproamide
<220> FEATURE:
<221> NAME/KEY: MOD_RES
<222> LOCATION: (9)..(9)

<223> OTHER INFORMATION: 6-aminocapramide

<400> SEQUENCE: 53

Xaa Glu Xaa Val Ala Leu Ser Arg Xaa
1               5

<210> SEQ ID NO 54
<211> LENGTH: 10
<212> TYPE: PRT
<213> ORGANISM: Artificial Sequence
<220> FEATURE:
<223> OTHER INFORMATION: chemicaly synthesized
<220> FEATURE:
<221> NAME/KEY: MOD_RES
<222> LOCATION: (1)..(1)
<223> OTHER INFORMATION: O-(alpha-N-acetylgalactosaminyl)-threonine
<220> FEATURE:
<221> NAME/KEY: MOD_RES
<222> LOCATION: (3)..(3)
<223> OTHER INFORMATION: Nva
<220> FEATURE:
<221> NAME/KEY: MOD_RES
<222> LOCATION: (4)..(4)
<223> OTHER INFORMATION: Nva
<220> FEATURE:
<221> NAME/KEY: MOD_RES
<222> LOCATION: (10)..(10)
<223> OTHER INFORMATION: 6-aminocapramide

<400> SEQUENCE: 54

Xaa Glu Xaa Xaa Val Ala Leu Ser Arg Xaa
1               5                   10

<210> SEQ ID NO 55
<211> LENGTH: 20
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: 1-cyclohexane-carboxylic acid

<400> SEQUENCE: 55

Xaa Arg Pro Asp Lys Pro Arg Pro Tyr Leu Pro Arg Pro Arg Pro Pro
1               5                   10                  15

Arg Pro Val Arg
            20

<210> SEQ ID NO 56
<211> LENGTH: 3800
<212> TYPE: DNA
<213> ORGANISM: Homo sapiens

<400> SEQUENCE: 56
ggcacgagcc ggtctggctt gggcaggctg cccgggccgt ggcaggaagc cggaagcagc      60
cgcggcccca gttcgggaga catggcgggc gttaaagctc tcgtggcatt atccttcagt     120
ggggctattg gactgacttt tcttatgctg ggatgtgcct tagaggatta tgggtgtact     180
tctctgaagt aagatgattt gtcaaaaatt ctgtgtggtt tgttacatt gggaatttat      240 ttatgtgata actgcgttta acttgtcata tccaattact ccttggagat ttaagttgtc     300
ttgcatgcca ccaaattcaa cctatgacta cttccttttg cctgctggac tctcaaagaa     360
tacttcaaat tcgaatggac attatgagac agctgttgaa cctaagttta attcaagtgg     420
tactcacttt tctaacttat ccaaaacaac tttccactgt tgctttcgga gtgagcaaga     480

```
tagaaactgc tccttatgtg cagacaacat tgaaggaaag acatttgttt caacagtaaa      540
ttctttagtt tttcaacaaa tagatgcaaa ctggaacata cagtgctggc taaaaggaga      600
cttaaaatta ttcatctgtt atgtggagtc attatttaag aatctattca ggaattataa      660
ctataaggtc catcttttat atgttctgcc tgaagtgtta aagattcac ctctggttcc       720 ccaaaaggc agttttcaga tggttcactg caattgcagt gttcatgaat gttgtgaatg       780
tcttgtgcct gtgccaacag ccaaactcaa cgacactctc cttatgtgtt tgaaaatcac      840
atctggtgga gtaattttcc agtcacctct aatgtcagtt cagcccataa atatggtgaa      900
gcctgatcca ccattaggtt tgcatatgga aatcacagat gatggtaatt taaagatttc      960
ttggtccagc ccaccattgg taccatttcc acttcaatat caagtgaaat attcagagaa     1020
ttctacaaca gttatcagag aagctgacaa gattgtctca gctacatccc tgctagtaga     1080
cagtatactt cctgggtctt cgtatgaggt tcaggtgagg ggcaagagac tggatggccc     1140
aggaatctgg agtgactgga gtactcctcg tgtctttacc acacaagatg tcatatactt     1200
tccacctaaa attctgacaa gtgttgggtc taatgtttct tttcactgca tctataagaa     1260
ggaaaacaag attgttccct caaaagagat tgtttggtgg atgaatttag ctgagaaaat     1320
tcctcaaagc cagtatgatg ttgtgagtga tcatgttagc aaagttactt ttttcaatct     1380
gaatgaaacc aaacctcgag gaaagtttac ctatgatgca gtgtactgct gcaatgaaca     1440
tgaatgccat catcgctatg ctgaattata tgtgattgat gtcaatatca atatctcatg     1500
tgaaactgat gggtacttaa ctaaaatgac ttgcagatgg tcaaccagta caatccagtc     1560
acttgcggaa agcactttgc aattgaggta tcataggagc agcctttact gttctgatat     1620
tccatctatt catcccatat ctgagcccaa agattgctat ttgcagagtg atggtttta      1680 tgaatgcatt ttccagccaa tcttcctatt atctggctac acaatgtgga ttaggatcaa     1740
tcactctcta ggttcacttg actctccacc aacatgtgtc cttcctgatt ctgtggtgaa     1800
gccactgcct ccatccagtg tgaaagcaga aattactata aacattggat tattgaaaat     1860
atcttgggaa aagccagtct ttccagagaa taaccttcaa ttccagattc gctatggttt     1920
aagtggaaaa aagtacaat ggaagatgta tgaggtttat gatgcaaaat caaaatctgt      1980
cagtctccca gttccagact tgtgtgcagt ctatgctgtt caggtgcgct gtaagaggct     2040
agatggactg ggatattgga gtaattggag caatccagcc tacacagttg tcatggatat     2100
aaaagttcct atgagaggac ctgaattttg gagaataatt aatggagata ctatgaaaaa     2160
ggagaaaaat gtcactttac tttggaagcc cctgatgaaa aatgactcat gtgcagtgt      2220 tcagagatat gtgataaacc atcatacttc ctgcaatgga acatggtcag aagatgtggg     2280
aaatcacacg aaattcactt tcctgtggac agagcaagca catactgtta cggttctggc     2340
catcaattca attggtgctt ctgttgcaaa ttttaattta accttttcat ggcctatgag     2400
caaagtaaat atcgtgcagt cactcagtgc ttatcccttta acagcagtt gtgtgattgt     2460 ttcctggata ctatcaccca gtgattacaa gctaatgtat tttattattg agtggaaaaa     2520
tcttaatgaa gatggtgaaa taaaatggct tagaatctct tcatctgtta agaagtatta     2580
tatccatgat cattttatcc ccattgagaa gtaccagttc agtctttacc caatatttat     2640
ggaaggagtg ggaaaaccaa agataattaa tagtttcact caagatgata ttgaaaaaca     2700
ccagagtgat gcaggtttat atgtaattgt gccagtaatt atttcctctt ccatcttatt     2760
gcttggaaca ttattaatat cacaccaaag aatgaaaaag ctattttggg aagatgttcc     2820
```

```
gaaccccaag aattgttcct gggcacaagg acttaatttt cagaagccag aaacgtttga    2880
gcatcttttt atcaagcata cagcatcagt gacatgtggt cctcttcttt tggagcctga    2940
aacaatttca gaagatatca gtgttgatac atcatggaaa aataaagatg agatgatgcc    3000
aacaactgtg gtctctctac tttcaacaac agatcttgaa aagggttctg tttgtattag    3060
tgaccagttc aacagtgtta acttctctga ggctgagggt actgaggtaa cctatgaggc    3120
cgaaagccag agacaaccct tgttaaaata cgccacgctg atcagcaact ctaaaccaag    3180
tgaaactggt gaagaacaag ggcttataaa tagttcagtc accaagtgct tctctagcaa    3240
aaattctccg ttgaaggatt cttttctctaa tagctcatgg gagatagagg cccaggcatt    3300
ttttatatta tcagatcagc atcccaacat aatttcacca cacctcacat tctcagaagg    3360
attggatgaa ctttttgaaat tggagggaaa tttccctgaa gaaataatg ataaaaagtc    3420 tatctattat ttaggggtca cctcaatcaa aaagagagag agtggtgtgc ttttgactga    3480
caagtcaagg gtatcgtgcc cattcccagc cccctgttta ttcacggaca tcagagttct    3540
ccaggacagt tgctcacact tgtagaaaaa taatatcaac ttaggaactt ctagtaagaa    3600
gactttgtca tcttacatgc ctcaattcca aacttgttct actcagactc ataagatcat    3660
ggaaaacaag atgtgtgacc taactgtgta atttcactga agaaaccttc agatttgtgt    3720
tataatgggt aatataaagt gtaatagatt atagttgtgg gtgggagaga gaaaagaaac    3780
cagagtccaa atttgaaaat                                                3800

<210> SEQ ID NO 57
<211> LENGTH: 41
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: 1-cyclohexane-carboxylic acid
<220> FEATURE:
<221> NAME/KEY: MOD_RES
<222> LOCATION: (19)..(19)
<223> OTHER INFORMATION: N-methyl-arginine
<220> FEATURE:
<221> NAME/KEY: MOD_RES
<222> LOCATION: (21)..(21)
<223> OTHER INFORMATION: Dbu
<220> FEATURE:
<221> NAME/KEY: MOD_RES
<222> LOCATION: (23)..(23)
<223> OTHER INFORMATION: N-methyl-arginine
<220> FEATURE:
<221> NAME/KEY: MOD_RES
<222> LOCATION: (41)..(41)
<223> OTHER INFORMATION: 1-cyclohexane-carboxylic acid

<400> SEQUENCE: 57

Xaa Asp Lys Gly Ser Tyr Leu Pro Arg Pro Thr Pro Arg Pro Ile
1               5                   10                  15

Tyr Asn Xaa Asn Xaa Asn Xaa Asn Tyr Ile Pro Arg Pro Pro Thr Pro
            20                  25                  30

Arg Pro Leu Tyr Ser Gly Lys Asp Xaa
35                  40

<210> SEQ ID NO 58
<211> LENGTH: 10
<212> TYPE: PRT
<213> ORGANISM: Artificial Sequence
```

```
<220> FEATURE:
<223> OTHER INFORMATION: chemically synthesized
<220> FEATURE:
<221> NAME/KEY: MOD_RES
<222> LOCATION: (10)..(10)
<223> OTHER INFORMATION: leucinamide

<400> SEQUENCE: 58

Ser Thr Glu Val Val Ala Leu Ser Arg Xaa
 1               5                  10
```